US010550421B2

(12) United States Patent
Flor et al.

(10) Patent No.: US 10,550,421 B2
(45) Date of Patent: *Feb. 4, 2020

(54) OLIGONUCLEOTIDE-MEDIATED QUANTITATIVE MULTIPLEXED IMMUNOASSAYS

(71) Applicant: The University of Chicago, Chicago, IL (US)

(72) Inventors: Amy Flor, Chicago, IL (US); Ryan Duggan, Chicago, IL (US); Stephen Kron, Chicago, IL (US)

(73) Assignee: The University of Chicago, Chicago, IL (US)

( * ) Notice: Subject to any disclaimer, the term of this patent is extended or adjusted under 35 U.S.C. 154(b) by 131 days.

This patent is subject to a terminal disclaimer.

(21) Appl. No.: 15/606,045

(22) Filed: May 26, 2017

(65) Prior Publication Data

US 2017/0268036 A1    Sep. 21, 2017

Related U.S. Application Data

(63) Continuation of application No. 14/408,065, filed as application No. PCT/US2013/045872 on Jun. 14, 2013, now Pat. No. 9,663,818.
(Continued)

(51) Int. Cl.
*C12Q 1/6804* (2018.01)
*C12Q 1/6811* (2018.01)
(Continued)

(52) U.S. Cl.
CPC .......... *C12Q 1/6804* (2013.01); *C12Q 1/6811* (2013.01); *G01N 15/14* (2013.01);
(Continued)

(58) Field of Classification Search
CPC .... C12Q 1/6804; C12Q 1/6811; G01N 15/14; G01N 21/6486; G01N 33/54326;
(Continued)

(56) References Cited

U.S. PATENT DOCUMENTS 5,654,413 A    8/1997  Brenner ......................... 506/41
7,226,737 B2   6/2007  Pancoska et al. ........... 435/6.14
(Continued)

FOREIGN PATENT DOCUMENTS

WO    WO 9926067     5/1999
WO    WO 03042695    5/2003
(Continued)

OTHER PUBLICATIONS

Abdelrahman, A. I. et al. Metal-containing polystyrene beads as standards for mass cytometry. *Journal of Analytical Atomic Spectrometry* 25:260 (2010).
(Continued)

*Primary Examiner* — Gailene Gabel
(74) *Attorney, Agent, or Firm* — Norton Rose Fulbright US LLP

(57) ABSTRACT

Methods and compositions for quantitative immunoassays are provided, in which ligand-conjugated probes are used to label samples and ligand-surfaced microspheres are used as quantitative reference standards. Certain embodiments provide a method of quantitative flow cytometry where ligands are oligonucleotides, and a sample comprising one or more cells is contacted with a hybridized antibody::fluorophore labeled targeting construct to label the cells, and the labeled cells are analyzed. In some embodiments, a population of quantitative labeled oligospheres labeled with the same fluorescent label as the cells is analyzed using the flow cytometer and used to create a quantitative standard curve of cytometer intensity versus molecules fluorescent label per
(Continued)

oligosphere event. A standard curve trendline is established and used to determine the molecules of fluorescent label per cellular event for the antigen-positive cell populations. Based on molecules of fluorescent label per cell, the amount of Antibody Binding per Cell (ABC) is quantified.

18 Claims, 29 Drawing Sheets

Specification includes a Sequence Listing.

Related U.S. Application Data

(60) Provisional application No. 61/660,261, filed on Jun. 15, 2012.

(51) Int. Cl.

| | | |
|---|---|---|
| *G01N 15/14* | (2006.01) | |
| *G01N 33/543* | (2006.01) | |
| *G01N 33/569* | (2006.01) | |
| *G01N 21/64* | (2006.01) | |
| *G01N 33/68* | (2006.01) | |
| G01N 15/10 | (2006.01) | |
| G01N 15/00 | (2006.01) | |

(52) U.S. Cl.
CPC ... *G01N 21/6486* (2013.01); *G01N 33/54326* (2013.01); *G01N 33/54333* (2013.01); *G01N 33/56966* (2013.01); *G01N 33/56972* (2013.01); *G01N 33/6854* (2013.01); G01N 2015/008 (2013.01); G01N 2015/0065 (2013.01); G01N 2015/1006 (2013.01); G01N 2015/1402 (2013.01); G01N 2458/10 (2013.01)

(58) Field of Classification Search
CPC ....... G01N 33/54333; G01N 33/56966; G01N 33/56972; G01N 33/6854; G01N 2015/0065; G01N 2015/008; G01N 2015/1006; G01N 2015/1402; G01N 2458/10

See application file for complete search history.

(56) References Cited

U.S. PATENT DOCUMENTS

| | | | |
|---|---|---|---|
| 7,563,584 B2 | 7/2009 | Perez et al. ................... 435/7.2 | |
| 9,663,818 B2* | 5/2017 | Flor ................. G01N 33/56966 | |
| 2005/0191625 A1 | 9/2005 | Kobler et al. ................ 435/6.18 | |
| 2007/0037254 A1 | 2/2007 | Chisholm et al. ............ 435/69.1 | |
| 2007/0161043 A1 | 7/2007 | Nie et al. ........................ 435/7.1 | |
| 2010/0184101 A1 | 7/2010 | Buffiere et al. ............... 435/7.25 | |
| 2010/0285594 A1 | 11/2010 | Purvis, Jr. ........................ 436/10 | |
| 2013/0123121 A1* | 5/2013 | Schwartz ............. C12Q 1/6834 506/9 | |

FOREIGN PATENT DOCUMENTS

| | | |
|---|---|---|
| WO | WO 2005040429 | 8/2005 |
| WO | WO 2007024840 | 3/2007 |
| WO | WO 2008060713 | 4/2009 |
| WO | WO 2012071428 | 5/2012 |

OTHER PUBLICATIONS

Bailey et al., "DNA-Encoded Antibody Libraries: A Unified Platform for Multiplexed Cell Sorting and Detection of Genes and Proteins," *Journal of the American Chemical Society* 129:1959-1967, 2007.

Bendall et al., "Single-Cell Mass Cytometry of Differential Immune and Drug Responses Across a Human Hematopoietic Continuum," *Science* 332(6030):687-696, 2011.

Feldkamp et al., "CANADA: Designing nucleic acid sequences for nanobiotechnology applications," *Journal of Computational Chemistry* 31(3):660-663, 2010.

Feldkamp et al., "DNASequenceGenerator: A Program for the Construction of DNA Sequences," *DNA Computing* 2340:23-32, 2002.

Feldkamp et al., "Microarray-Based in vitro Evaluation of DNA Oligomer Libraries Designed in silico," *ChemPhysChem* 5(3):367-372, 2004.

International Search Report and Written Opinion issued in PCT/US2013/045872, dated Nov. 22, 2013.

Lim, S. H., Bestvater, F., Buchy, P., Mardy, S. & Yu, A. D. C. Quantitative analysis of nucleic acid hybridization on magnetic particles and quantum dot-based probes. *Sensors* 9:5590-5599 (2009).

Rossmann, E. D., Lenkei, R., Lundin, J., Mellstedt, H. & Österborg, A. Performance of calibration standards for antigen quantitation with flow cytometry in chronic lymphocytic leukemia. *Cytom. Part B—Clin. Cytom.* 72:450-457 (2007).

Smith, R. A. & Giorgio, T. D. Quantitative measurement of multifunctional quantum dot binding to cellular targets using flow cytometry. *Cytometry.* 75A:465-474 (2009).

Wang, L., Gaigalas, A. K. & Yan, M. Quantitative fluorescence measurements with multicolor flow cytometry. *Methods Mol. Biol.* 699:53-65 (2011).

Wu, Y. et al. The development of quantum dot calibration beads and quantitative multicolor bioassays in flow cytometry and microscopy. *Anal. Biochem.* 364:180-192 (2007).

\* cited by examiner

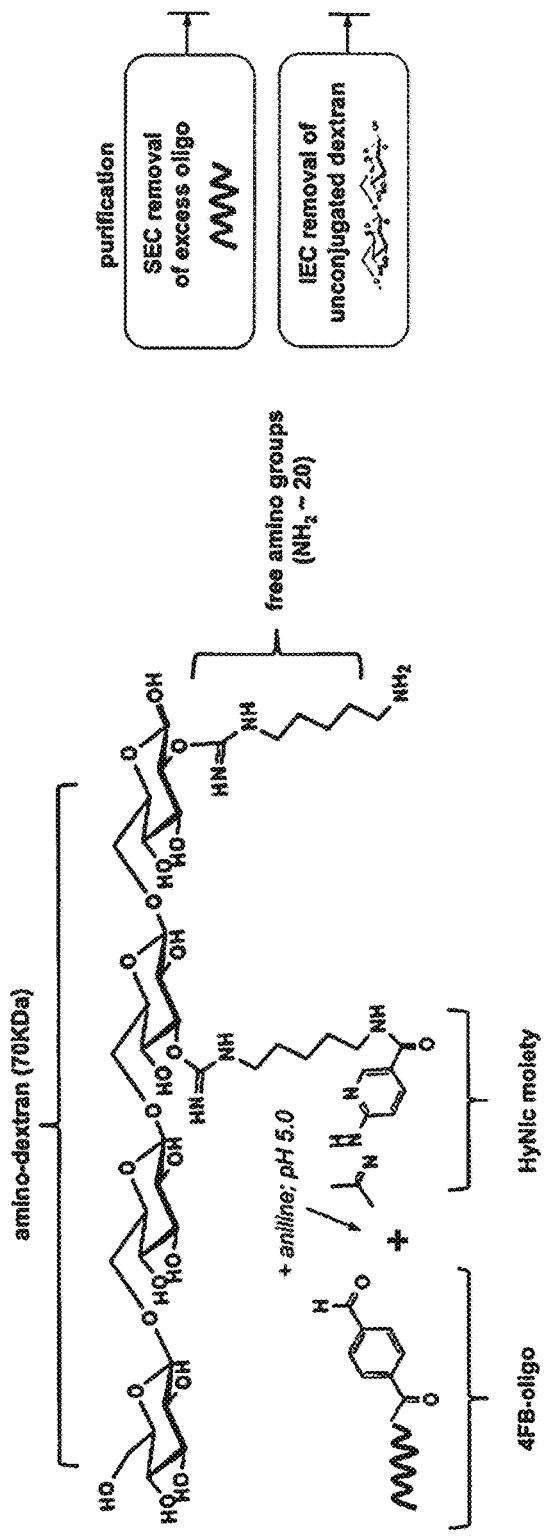
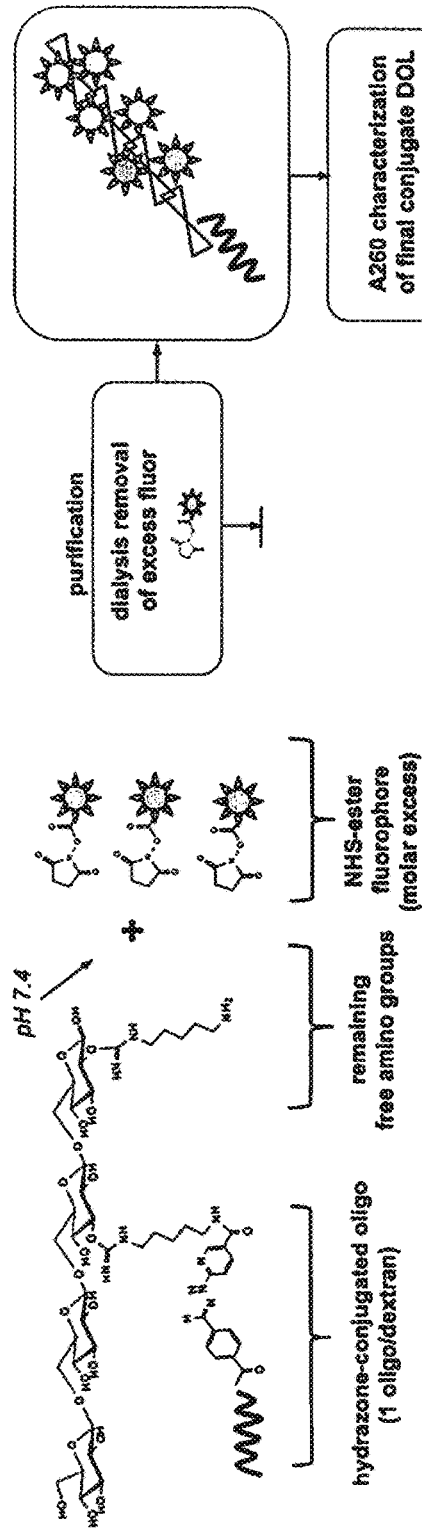
FIG. 1B

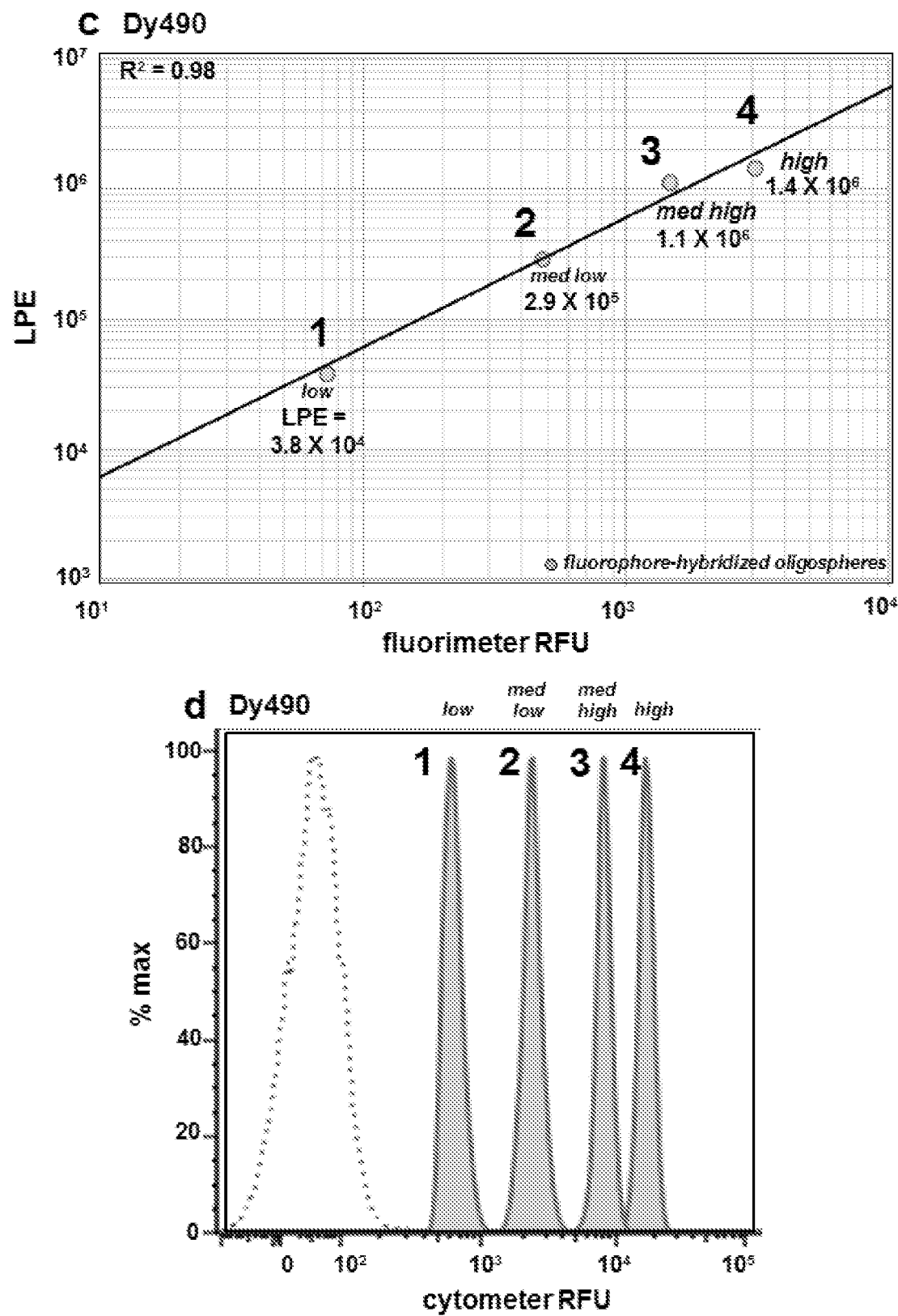
FIG. 5C-D

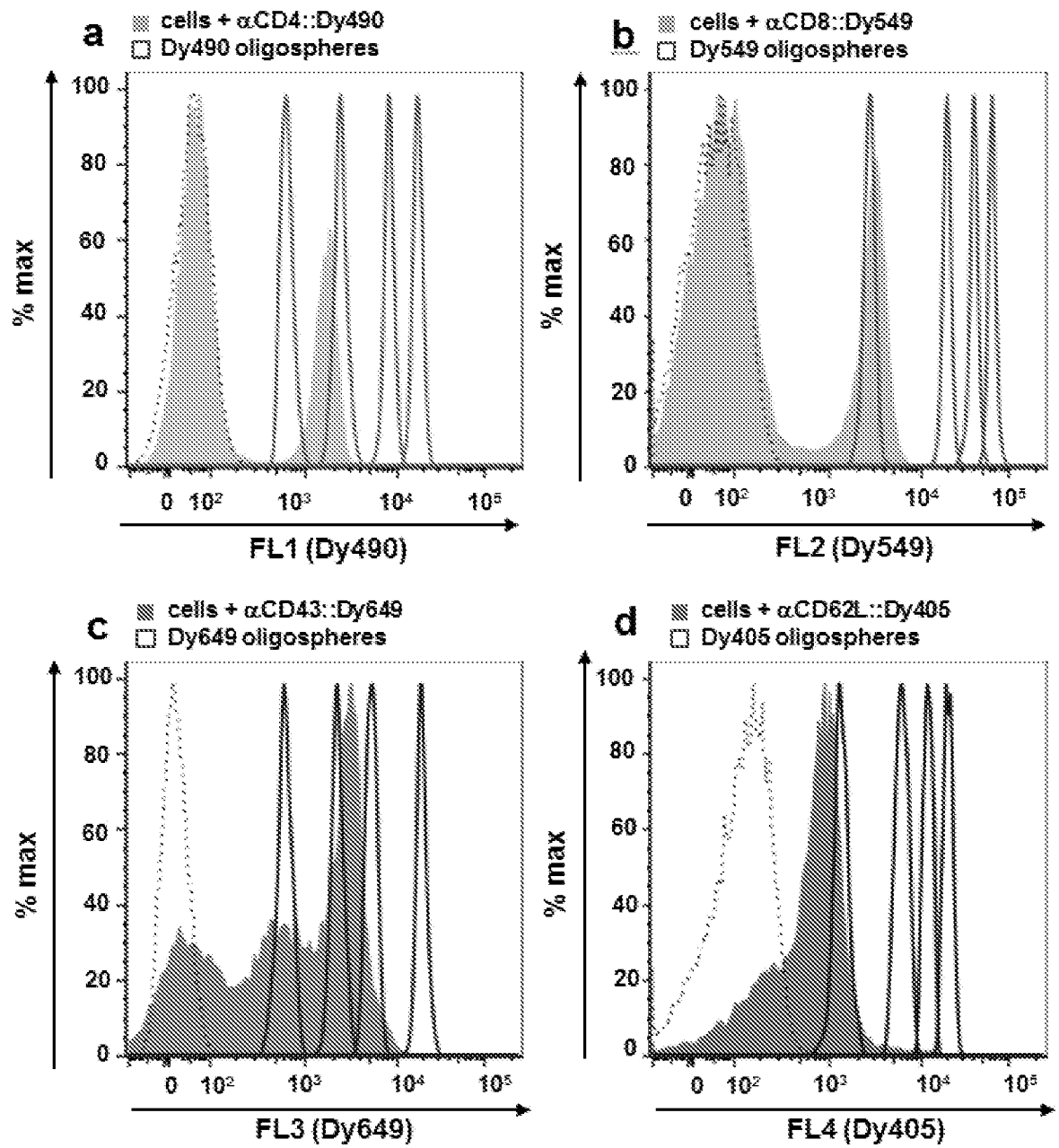
FIG. 6A-D

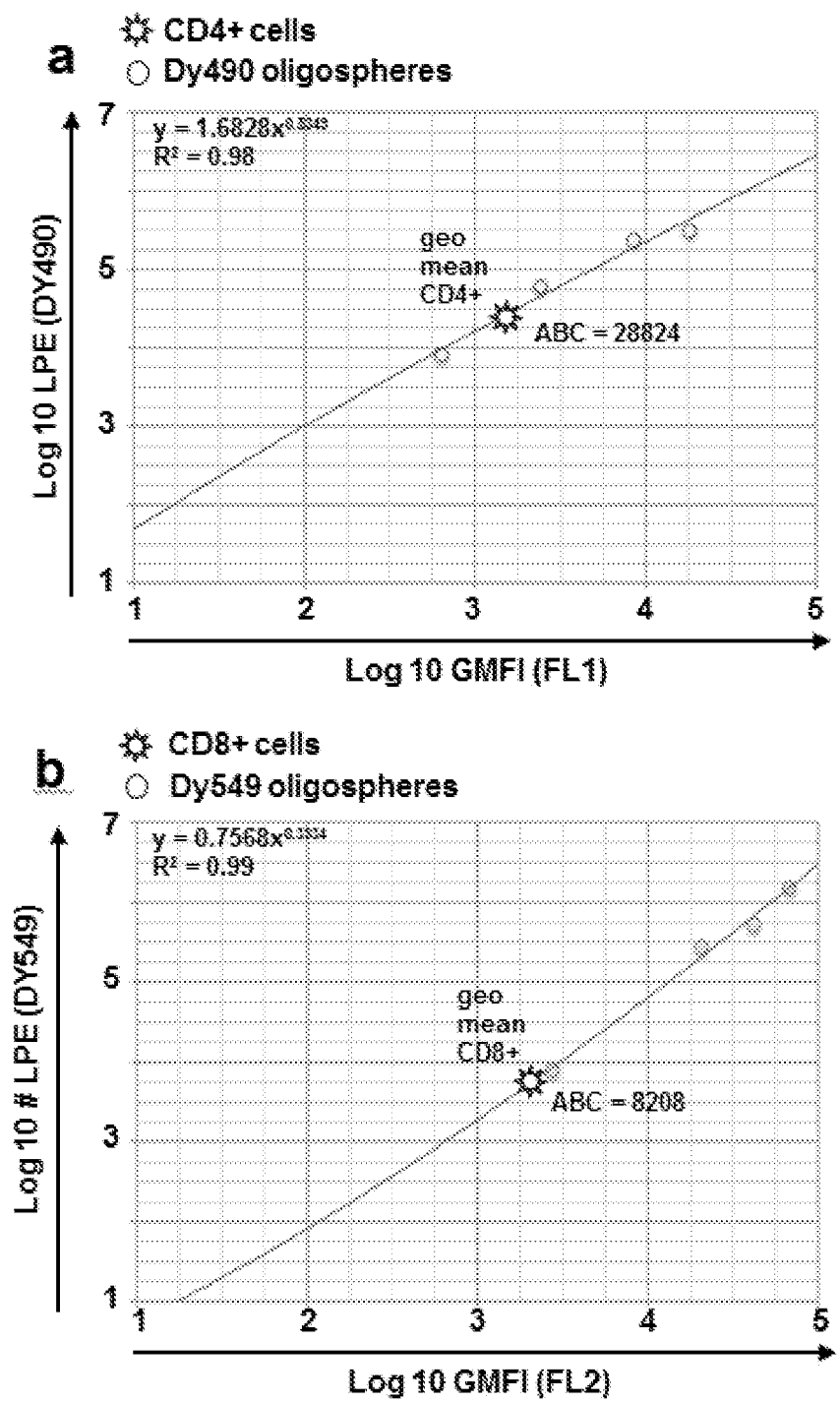
FIG 7A-B

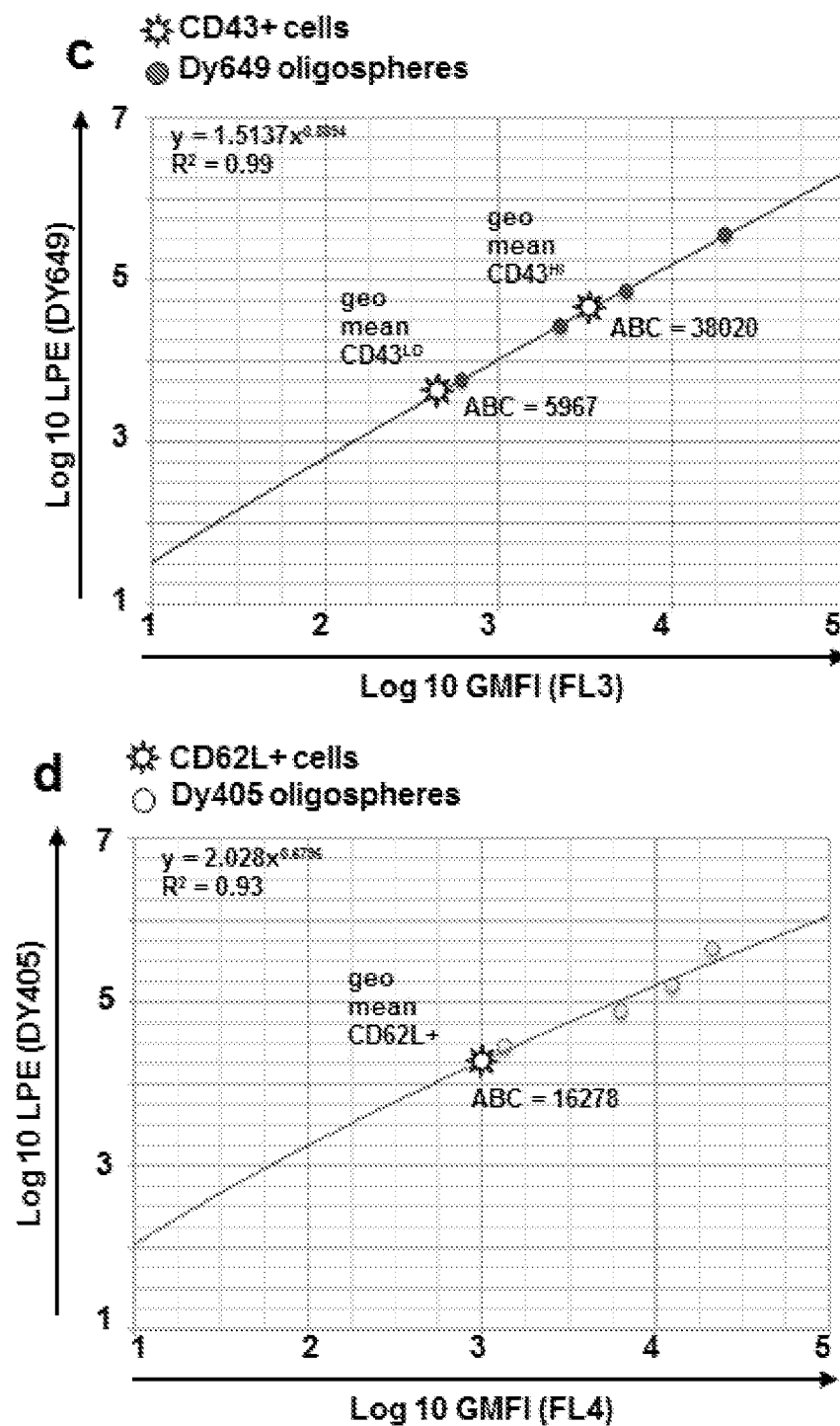
FIG. 7C-D

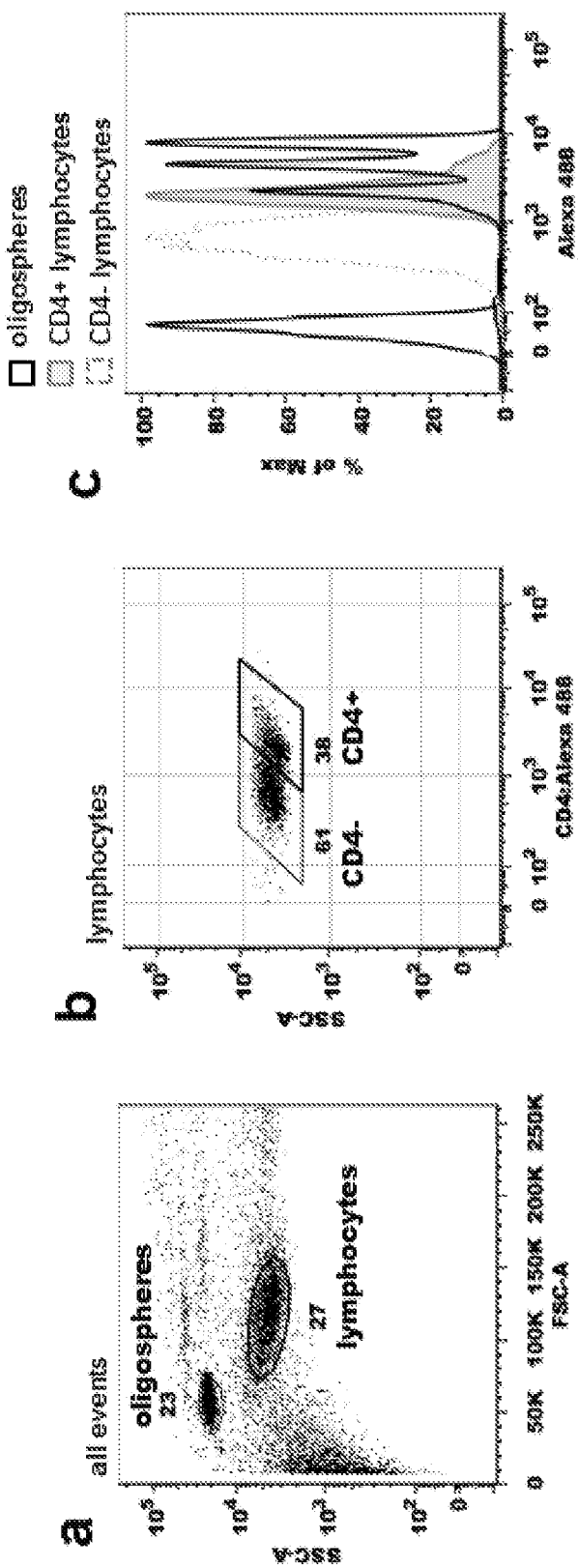
FIG. 9A-C

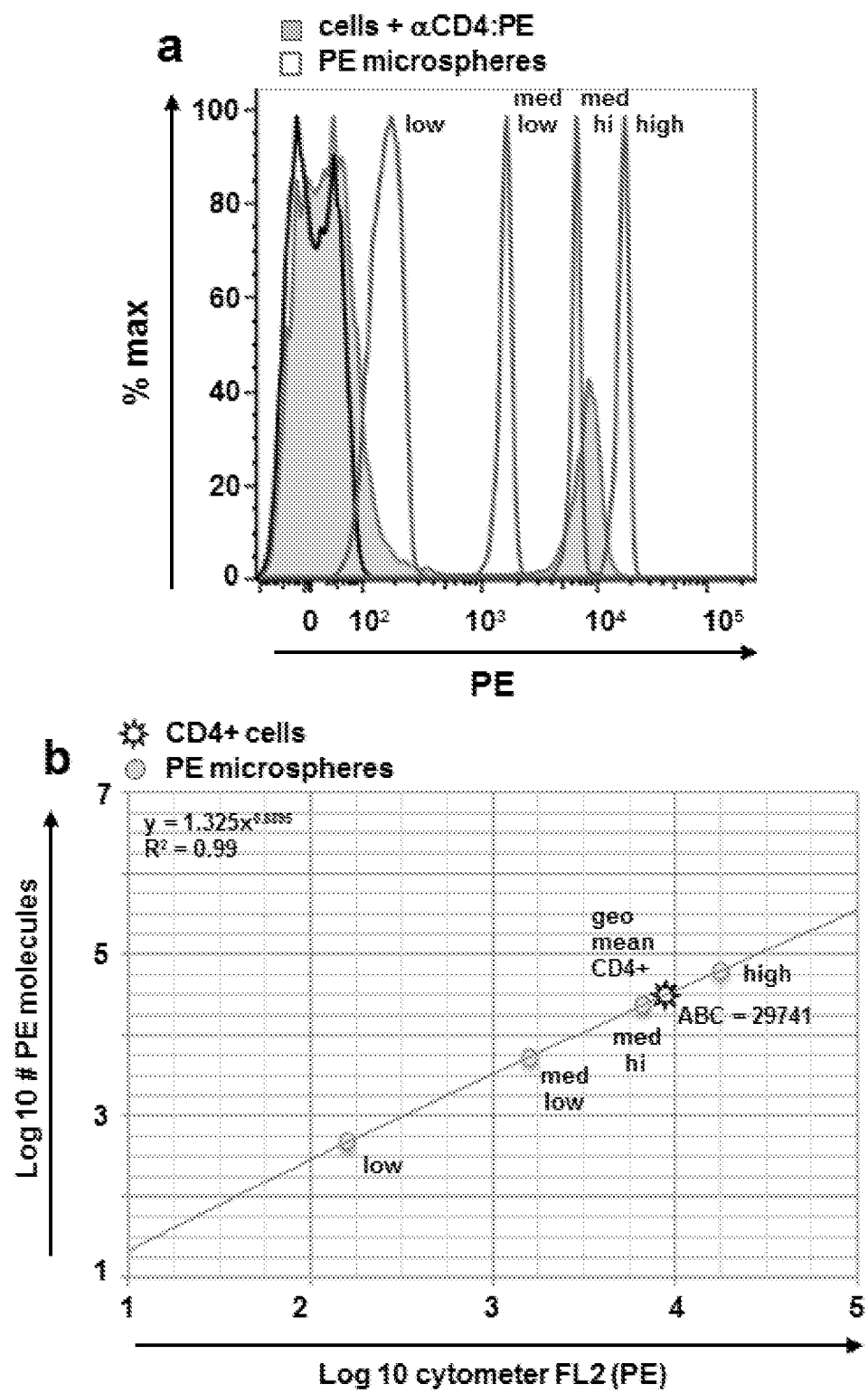
FIG. 10A-B

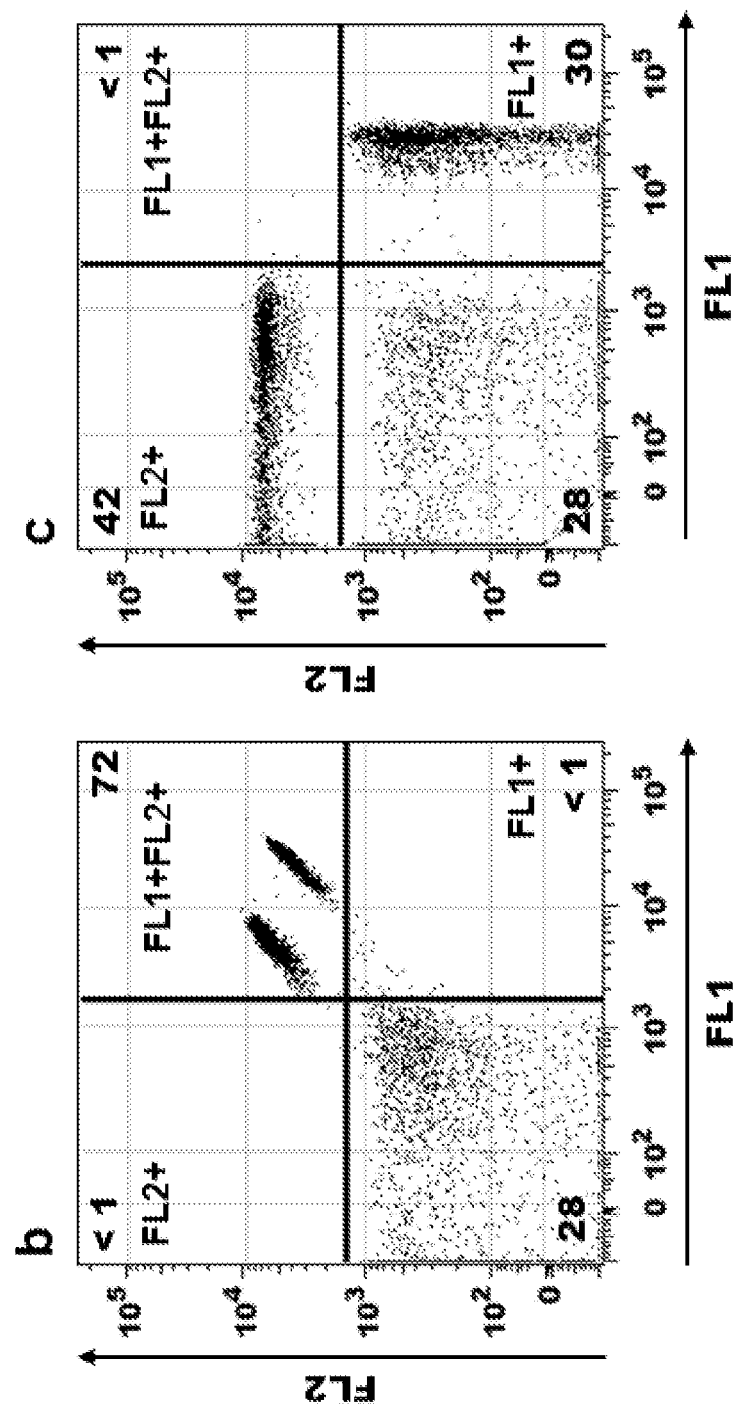
FIG. 12B-C

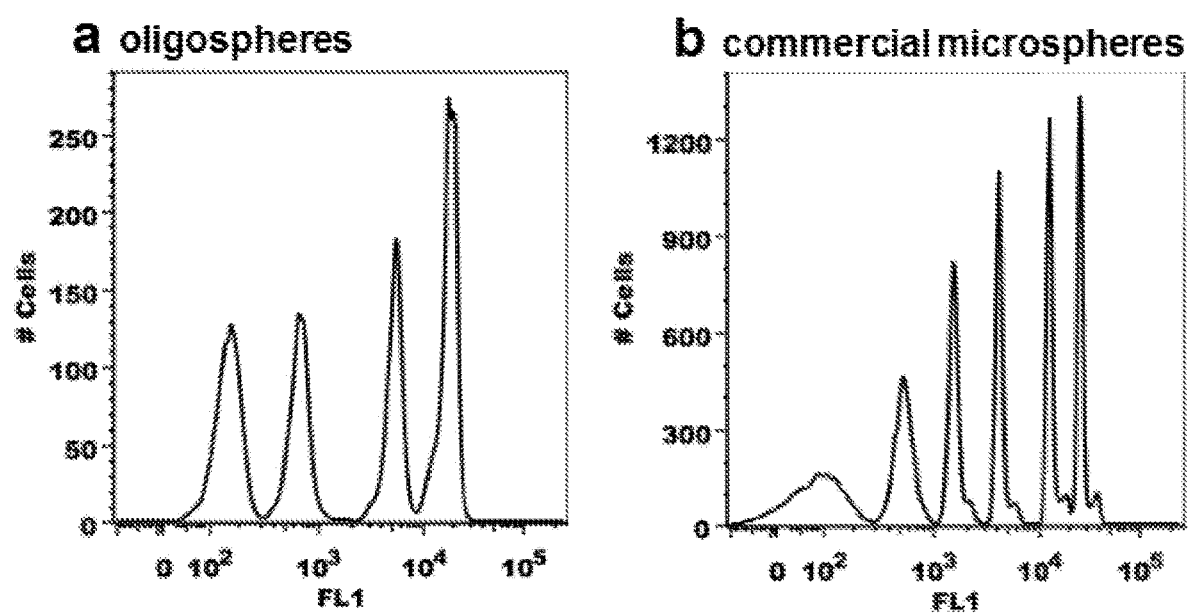
FIG. 14A-B

OLIGONUCLEOTIDE-MEDIATED QUANTITATIVE MULTIPLEXED IMMUNOASSAYS

CROSS-REFERENCE TO RELATED APPLICATIONS

This application is a continuation of U.S. patent application Ser. No. 14/408,065 filed Dec. 15, 2014, which is a national phase application under 35 U.S.C. § 371 of International Application No. PCT/US2013/045872, filed Jun. 14, 2013, which claims the benefit of priority to U.S. Provisional Patent Application Ser. No. 61/660,261, filed Jun. 15, 2012. The entire contents of each of the above-referenced disclosures are specifically incorporated herein by reference without disclaimer.

BACKGROUND

1. Field of the Invention

The present invention relates generally to the fields of immunology, molecular biology, and cellular biology. More particularly, it relates to quantitative multiplexed cellular analysis using flow cytometry, microscopy, and/or fluorimetry.

2. Description of Related Art

Multiplexed target labeling and analysis are principal strategies applied in molecular biology research. In general, surface or intracellular antigens indicative of cell status are detected by multiplexed labeling with targeting reagents (e.g., antibodies), followed by visualization of the targeting reagents by specific labeling probes (e.g., fluorophores). In some instances, targets in solution are analyzed using a similar approach. The sample is analyzed by flow cytometry, microscopy, fluorimetry, or other instrumentation equipped to measure labeling probe signal.

Multiplexed targeting assays have been facilitated in the last several decades by an increasing variety of commercially available antibodies biochemically conjugated to labeling reagents. Fluorescent reagents are the most common type of label used in the laboratory, although other labels may be utilized for specific applications (enzymes, radioisotopes, heavy metals, etc). Despite the growing availability of directly-labeled targeting reagents, the majority of reagents are only available conjugated to a limited number of labels, often in the same standard fluorophore such as FITC. This is particularly true of reagents targeting novel or niche markers.

A variety of parameters must be considered in order to determine an optimal multiplexed detection strategy, including cell type(s), target densities, labeling reagent characteristics, and instrument specifications. Limitations placed on label-target choice by commercial availability, coupled with reliance on qualitative analysis parameters, can cause variation in results and subsequent interpretation of data across experiments, researchers, and laboratories.

The prevalence of qualitative, rather than quantitative, analysis in many immunoassays is a result of several factors. Qualitative analysis is almost universally practiced with flow cytometric and microscopy assays, due to the nature of instrumentation, which are configured to provide a measure of adjustable, relative intensity, rather than units of absolute intensity. While some quantitative technologies exist, such as dyed fluorescent microspheres, at present these technologies require an additional investment of cost and preparation time that may deter many researchers, and even when utilized may not produce reliable and accurate quantitative measures. Although immunoanalysis procedures are, by and large, executed by researchers with considerable experience and expertise, there is no question that a streamlined method of accurate, quantitative analysis would represent a significant asset to the field—notably, for flow cytometric applications which are particularly subject to variation and error incurred by the qualitative approach.

As existing technologies are often time-consuming, cumbersome, and inaccurate, it is understandable that the quantitative analysis endeavor is not usually pursued by the research laboratory.

SUMMARY OF THE INVENTION

Various embodiments address challenges presented by conventional qualitative immunoassay methods by utilizing DNA-directed assembly or other means by which complementary ligands pair to form a one-to-one complex for quantitative target labeling. In certain embodiments, antibodies are used as the targeting reagent, and oligonucleotides are used as the ligand. Antibody:oligonucleotide targeting constructs are hybridized to complementary oligonucleotide:label constructs to create a labeled targeting hybrid. The hybrid is then used to label antigens and provide a signal for analysis. Alternatively, targeting constructs are first applied to a sample and then the labeling construct is applied, providing a signal for analysis. Labeled quantitative oligospheres are added to the analysis and used to convert relative units of signal intensity provided by the label to absolute measures of Label Per Event (LPE). In certain embodiments, an event may comprise a single cell, a volume of solution, a concentration or volume of analyte, or a unit of surface area.

LPE is then used to quantify the number of targeting reagent molecules within a sample based on known label-target ratio, which is established during ligation of targeting construct to labeling construct. In certain embodiments in which the targeting reagent is an antibody, and the sample comprises a cellular preparation, the quantitative measure is noted as Antibodies Bound per Cell (ABC).

As used herein, a ligand-surfaced microsphere refers to a microsphere to which a ligand is conjugated. Non-limiting examples of ligands may include oligonucleotides, peptides, or haptens. Specifically, an "oligosphere" refers to a microsphere to which oligonucleotides are conjugated for surface ligation.

Several techniques are known for conjugating ligands to microspheres. The ligand-microsphere conjugation procedure may involve modification of amine, carboxyl, hydroxyl or other reactive groups on oligonucleotides and microsphere surfaces in order to incorporate linker moieties for subsequent conjugation reaction. Linker chemistry may include HyNic/4FB (hydrazone), (strept)avidin/biotin, phosphoramidite, octadinyl dU, and other chemistries. Alternatively, the microspheres may be pre-manufactured to present surface reactive groups to which reactive-group bearing oligo may be conjugated (e.g., amino- or streptavidin-modified microspheres). In certain aspects, a linker sequence is placed between the microsphere and the operative region of the oligonucleotide. Such linkers may, for example, facilitate conjugation to the microsphere and/or reduce steric hindrance of the oligonucleotide.

Microspheres are generally spherical particles with diameters in the micrometer range (i.e., 1 μm to 1,000 μm). For flow cytometer applications, oligospheres with diameters between about 1-10 μm, 3-8 μm, or 3-6 μm, are preferred.

Microspheres may be made from various materials including, polymers (e.g., polyethylene or polystyrene), glass, or ceramic.

In certain aspects, the microspheres are magnetic. As used herein, "magnetic" includes paramagnetic and super paramagnetic. The microspheres may also be encoded. The size of the microspheres in a subpopulation may also be used to distinguish one subpopulation from another. Another method of encoding microspheres is to incorporate a magnetically responsive substance, such as $Fe_3O_4$, into the structure. Paramagnetic and superparamagnetic microspheres have negligible magnetism in the absence of a magnetic field, but application of a magnetic field induces alignment of the magnetic domains in the microspheres, resulting in attraction of the microspheres to the field source. Combining fluorescent dyes, microsphere size, and/or magnetically responsive substances into the microspheres can further increase the number of different subpopulations of ligand-conjugated microspheres that can be created.

As used herein a "labeled oligosphere" refers to an oligosphere and a labeling construct, in which the respective oligonucleotides have annealed to form a hybrid. As discussed, labeling constructs contain a labeling moiety and are designed to hybridize to the oligonucleotide sequences on the oligospheres. A number of techniques are known for attaching labeling moieties to nucleic acids. These techniques include the use of a dextran scaffold bearing oligonucleotides and fluorophores, as well as the direct conjugation of the fluorophore conjugated to the oligonucleotide.

Compositions comprising a population of quantitative labeled oligospheres prepared according to the methods disclosed herein also are provided.

As used herein a "targeting oligosphere" refers to an oligosphere and a targeting construct to which the respective oligonucleotides have annealed to form a hybrid.

Certain embodiments provide a method of preparing a population of quantitative labeled oligospheres comprising: (a) separately combining at least 2, 3, 4, 5, 6, 7, 8, 9, 10, 11, or 12 or more subpopulations of oligospheres with at least 2, 3, 4, 5, 6, 7, 8, 9, 10, 11, or 12 or more different concentrations of labeling constructs under conditions suitable for the hybridization of the oligospheres to the probes to obtain at least 2, 3, 4, 5, 6, 7, 8, 9, 10, 11, or 12 or more subpopulations of labeled oligospheres; and (b) combining the subpopulations of labeled oligospheres to obtain a titrated population of quantitative oligospheres bearing known numbers of labeling molecules at discrete and increasing saturations, providing a standard curve against which an unknown sample can be evaluated. The titrated population of labeled oligospheres will, therefore, comprise at least 2, 3, 4, 5, 6, 7, 8, 9, 10, 11, or 12 or more subpopulations of labeled oligospheres having different amounts of labeling moiety. In some embodiments, at most or at least 2, 3, 4, 5, 6, 7, 8, 9, 10, 11, or 12 or more subpopulations of oligospheres (or any range derivable therein) are combined with at least or at most 2, 3, 4, 5, 6, 7, 8, 9, 10, 11, or 12 or more different concentrations of labeling construct (or any range derivable therein) under conditions suitable for the hybridization of the oligospheres to the labeling construct to obtain at least or at most 2, 3, 4, 5, 6, 7, 8, 9, 10, 11, or 12 or more subpopulations of labeled oligospheres (or any range derivable therein). As used herein "quantitative oligospheres" means a population of labeled oligospheres containing at least two different subpopulations of labeled oligospheres, as described herein.

Methods of preparing a population of quantitative oligospheres may further comprise individually analyzing the subpopulations of quantitative oligospheres by flow cytometry prior to combining the subpopulations of quantitative oligospheres to obtain the titrated population of quantitative oligospheres. This analysis may comprise analyzing one or more parameters including, but not limited to, peak intensity, bandwidth, or peak separation of the subpopulations of the labeled oligospheres. In embodiments where encoded microspheres are used, parameters relating to the encoding moieties (e.g., internal fluorescent dyes) may also be analyzed. In certain aspects relating to flow cytometry, the labeled oligospheres are gated on singlets and then the singlets are visualized as histograms. The histograms of the subpopulations of labeled oligospheres may be overlayed.

Methods of preparing a population of labeled oligospheres may further comprise quantifying a Label-signal Per oligosphere Event (LPE) using a microplate fluorimeter to measure sample intensity versus a standard curve. In some embodiments, the label-signal is a fluorescent signal, and intensity is converted to LPE using a linear trendline equation provided by a fluorescent standard curve. In certain aspects, methods of preparing a population of labeled oligospheres may further comprise determining the number of labeled oligospheres in a sample using a handheld particle counter or other counting devices known to those in the art.

The ligand-conjugated microspheres and antibody:ligand targeting constructs disclosed herein may be used in numerous applications including, for example, Quantitative Flow Cytometry (QFC), spectral compensation for polychromatic flow cytometry, reference standards for Quality Control (QC) of cytometric instrumentation (i.e. alignment or calibration), single cell mass cytometry (CyTOF), microscopy, and Enzyme-Linked ImmunoSorbent Assays (ELISA). Microscopy applications include, for example, singleplex or multiplex Quantitative ImmunoCytoChemistry (Q-ICC) or ImmunoHistoChemistry (Q-IHC).

A variety of labeling moieties may be employed in the methods and compositions disclosed herein. Non-limiting examples of labeling moieties include biofluors (e.g., phycoerythrin (PE), allophycocyanin (APC), small molecule fluorophores (FITC, Alexa dyes, DyLight dyes, eFluor dyes, etc.), fluorescent proteins (GFP, CFP, YFP, mCherry, dsRed, etc.), or quantum dots. For CyTOF applications heavy metal or isotope labeling moieties are preferred. For ELISA or ICC/IHC, enzymatic labeling moieties may be used (e.g., horseradish peroxidase, alkaline phosphatase, etc), followed by a tertiary detection reagent (e.g., fluorescent, colorimetric, or luminescent enzyme substrate). In some embodiments, radioisotopes may be used as a label.

Non-limiting examples of fluorophores include Alexa Fluor (e.g. Alexa Fluor 488, 532, or 647), BODIPY® (e.g. BODIPY®-630/650, -650/665, -FL, R6G, -TMR, or -TRX) CyDye™ (e.g. Cy2™, Cy3™, or Cy5™), DyLight™ (e.g. Dy490, Dy549, Dy649, and Dy405), acridine orange, coumarin, cyanine, fluorescein, resorufin, and rhodamine dyes. Other non-limiting examples of fluorescent dyes include an orange fluorescent squarine dye such as 2,4-Bis [3,5-dimethyl-2-pyrrolyl] cyclobutenediylium-1,3-diololate, a red fluorescent squarine dye such as 2,4-Bis [1,3,3-trimethyl-2-indolinylidenemethyl] cyclobutenediylium-1,3-dioxolate, or an infrared dye such as 2,4 Bis [3,3-dimethyl-2-(1H-benz [e]indolinylidenemethyl)] cyclobutenediylium-1,3-dioxolate. Further examples of fluorescent dyes include quantum dots, AMCA, Cascade Blue®, 6-FAM™, HEX™, 6-JOE, Oregon Green®, Pacific Blue™, REG, Rhodamine Green™, Rhodamine Red™, ROX™, TAMRA™, TET™, Tetramethylrhodamine (TMR), or Texas Red®. Fluorophores may include phycobilliproteins including, but not limited to, phycoerythrin (PE) and allophycocyanin (APC), or tandem-dye preparations of phycobiliproteins (e.g. PE-Cy5 or APC-Cy7).

The sequences of the oligonucleotides used in the in the methods and compositions disclosed herein are not limited to any particular sequence. Those of ordinary skill in the art will be able to determine appropriate sequences based on the assay conditions, particularly hybridization conditions and the potential for undesirable cross-hybridization with other probes or sequences in the sample. It is generally desirable to use oligonucleotides that have low reactivity with unmatched oligo sequences, high melting temperature, and stable and robust hybridization activity. It may also be desirable to use oligonucleotides that form hairpin structures. Preferably, oligos will not hybridize to other nucleic acids in the sample during a reaction. The proper selection of non-cross hybridizing sequences is useful in assays, particularly assays in a highly parallel hybridization environment, that require stringent non-cross hybridizing behavior. In certain embodiments, the sequences are between 6 to 60, 8 to 50, 10 to 40, 10 to 20, 12 to 24, or 20 to 30 nucleotides in length. Non-limiting examples of such sequences include the sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, and their respective complementary sequences. The oligonucleotides may comprise natural bases (A, T/U, G, and C) and/or non-natural bases (e.g., peptide nucleic acids (PNAs), locked nucleic acids (LNAs), iso-nucleotides).

Other embodiments provide an interchangeable labeling system comprising: (a) an antibody:oligonucleotide targeting construct comprising an antibody region and a first universal nucleic acid region; and (b) a plurality of different labeling constructs comprising a label and a second universal nucleic acid region that is complementary to the first universal nucleic acid region, wherein each of the plurality of different labeling constructs has a different label, but comprises the same second universal nucleic acid region.

Further embodiments provide an antibody:oligonucleotide targeting construct comprising a first oligonucleotide, an oligosphere conjugated to a second oligonucleotide comprising a sequence identical to the sequence of the first oligonucleotide, and a labeling construct comprising a third sequence that is complementary to the first and the second oligonucleotides. In some embodiments, the first oligonucleotide comprises a sequence selected from the group consisting of the sequence of, or a sequence complementary to the sequence of, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, the second oligonucleotide comprises a sequence selected from the group consisting of the sequence of, or a sequence complementary to the sequence of, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

Other embodiments provide a composition comprising a titrated population of labeled oligospheres, wherein the titrated population of labeled oligospheres comprises at least 2, 3, 4, 5, 6, 7, 8, 9, 10, 11, or 12 subpopulations of labeled oligospheres, wherein each of the subpopulations of labeled oligospheres is hybridized to a different amount of labeling construct.

Certain embodiments provide a method of quantitative flow cytometry comprising: (a) contacting a sample comprising one or more cells with a labeled targeting hybrid under conditions suitable for binding of the labeled targeting hybrid construct to an antigen on the cells; (b) analyzing the cells bound to a labeled targeting hybrid in the sample using a flow cytometer; (c) analyzing a population of quantitative labeled oligospheres, wherein the population of quantitative labeled oligospheres is labeled with the same fluorescent label as the labeled targeting hybrid construct; (d) determining a median, mean, or Geometric Mean Fluorescent Intensity (GMFI) for each population of quantitative labeled oligospheres; (e) creating a standard curve for quantitation of labeled targeting hybrid by plotting GMFI vs known molecules of label per microsphere event (LPE or FPE), LPE or FPE having been previously quantified fluorometrically; (f) determining the LPE or FPE for one or more cell populations which bind the labeled targeting hybrid's targeting moiety from the median, mean or GMFI of cellular event(s); (g) using the LPE or FPE to quantify the amount of labeled targeting hybrid per cell (i.e., ABC).

In certain aspects, the population of quantitative labeled oligospheres and the cells bound to the labeled targeting hybrid are combined in the sample prior to analyzing the mixed population of quantitative labeled oligospheres and cells bound to the labeled targeting hybrid in the flow cytometer. In some aspects, the population of quantitative labeled oligospheres are analyzed in the flow cytometer before or after the cells bound to the labeled targeting hybrid are analyzed in the flow cytometer. In other aspects, cells bound to an unhybridized targeting construct and unhybridized oligospheres bearing increasing titrations of free oligonucleotide are combined in the presence of an excess of labeling construct comprising a complementary oligonucleotide to the targeting construct and hybridization is allowed to proceed, followed by flow cytometric analysis of the mixed sample of cells bound to new labeled targeting hybrid and oligospheres.

In one embodiment, a method of quantitative flow cytometry is provided comprising: (a) contacting a sample comprising one or more cells with a labeled targeting hybrid under conditions suitable for binding of the labeled targeting hybrid construct to an antigen on the cells; (b) contacting the sample with a population of quantitative oligospheres wherein the population of quantitative oligospheres is labeled with the same labeling moiety as the labeled targeting hybrid; (c) analyzing a population of quantitative labeled oligospheres and the cells bound to the labeled targeting hybrid in the sample in a cytometer; (d) determining a median, mean, or Geometric Mean Fluorescent Intensity (GMFI) for each population of quantitative labeled oligospheres; (e) creating a standard curve for quantitation of labeled targeting hybrid by plotting GMFI vs known molecules of label per microsphere event (LPE or FPE), the LPE or FPE having been previously quantified fluorometrically; (f) determining the LPE or FPE for one or more cell populations which bind the labeled targeting hybrid's targeting moiety from the median, mean or GMFI of cellular event(s); and (g) using the LPE or FPE to quantify the amount of labeled targeting hybrid per cell (i.e., ABC).

In another embodiment, a method of quantitative flow cytometry is provided comprising: (a) contacting a sample comprising one or more cells with an unlabeled targeting construct under conditions suitable for binding of the targeting construct to an antigen on the cells; (b) contacting the sample with a population of unlabeled oligospheres; (c) contacting the mixed sample of cells and oligospheres with sufficient labeling construct to hybridize to oligospheres and targeting constructs, thereby creating quantitative oligospheres labeled with the same labeling moiety as the targeting construct bound to antigen on the cells; (d) analyzing a population of quantitative labeled oligospheres and labeled cells in the sample in a cytometer; (e) determining a median, mean, or Geometric Mean Fluorescent Intensity (GMFI) for each population of quantitative labeled oligospheres; (f) creating a standard curve for quantitation of labeled targeting hybrid by plotting GMFI vs known molecules of label per microsphere event (LPE or FPE), LPE or FPE having been previously quantified fluorometrically; (g) determining the LPE or FPE for one or more cell populations which bind the labeled targeting hybrid's targeting moiety from the median, mean or GMFI of cellular event(s); (g) using the LPE or FPE to quantify the amount of labeled targeting hybrid per cell (i.e., ABC).

Another embodiment provides a method of flow cytometric spectral compensation comprising: (a) analyzing at least two populations of quantitative labeled oligospheres in the flow cytometer bearing a single label in each population; (b) obtaining cytometric data in at least two cytometric detector channels for all labeled oligospheres being analyzed; (c) utilizing cytometric data acquisition and/or analysis software to determine spectral compensation parameters using labeled oligosphere data; and (d) applying compensation parameters to cells labeled with at least two label-target hybrids bearing the same labels as the labeled oligospheres used to determine compensation parameters.

Other embodiments provide a method of calibration of cytometric instrumentation comprising: (a) analyzing at least one population of quantitative labeled oligospheres in a flow cytometer; (b) obtaining cytometric data in at least one cytometric detector channel; (c) utilizing known degree-of-labeling data of quantitative oligospheres to evaluate sensitivity and resolution of the instrument; and (d) performing calibration and alignment procedures based on observed signaling of labeled oligospheres.

A further embodiment provides a method of quantitative immunocytochemistry comprising: (a) contacting a sample comprising one or more cells with a labeled targeting hybrid under conditions suitable for binding of the labeled targeting hybrid to a cellular target; (b) contacting the labeled cell sample with a population of quantitative labeled oligospheres bearing the same label as the labeled targeting hybrids applied to the cells; (c) analyzing the sample using a microscope equipped with an appropriate fluorescent filter to observe the fluorescent signal of the labeled cells and microspheres, using a camera and imaging software to obtain representative images of the sample; (d) utilizing image-analysis software to create a signal-to-noise threshold and intensity standard curve using fluorescent oligospheres; (e) utilizing the signal intensity data provided by the labeled oligospheres to quantitate signal intensity of labeled cells; and (f) converting cell signal intensity units to hybrid-per-cell units by (signal intensity/label-target DOL).

One embodiment provides a method of quantitative immunocytochemistry comprising: (a) contacting a sample comprising one or more cells with at least a first and a second labeled targeting hybrid under conditions suitable for binding of the hybrid to a cellular target; (b) contacting the labeled cell sample with a population of at least a first and a second population of quantitative labeled oligospheres bearing the same label as the labeled targeting hybrids applied to the cells; (c) analyzing the sample using a microscope equipped with an appropriate fluorescent filter to observe the fluorescent signal of the labeled cells and microspheres, using a camera and imaging software to obtain representative images of the sample; (d) utilizing image-analysis software to create a signal-to-noise threshold and intensity standard curve using fluorescent oligospheres; (e) utilizing the signal intensity data provided by the labeled oligospheres to quantitate signal intensity of labeled cells; and (f) converting cell signal intensity units to hybrid-per-cell units for each label-target hybrid applied by (signal intensity/label-target DOL).

Another embodiment provides a method of quantitative immunocytochemistry comprising: (a) contacting a sample comprising a tissue sample with a labeled targeting hybrid under conditions suitable for binding of the hybrid to a target on or within the tissue; (b) contacting the labeled tissue sample with a population of quantitative labeled oligospheres bearing the same label as the labeled targeting hybrids applied to the tissue; (c) analyzing the sample using a microscope equipped with an appropriate fluorescent filter to observe the fluorescent signal of the labeled tissue and microspheres, using a camera and imaging software to obtain representative images of the sample; (d) utilizing image-analysis software to create a signal-to-noise threshold and intensity standard curve using fluorescent oligospheres; (c) utilizing the signal intensity data provided by the labeled oligospheres to quantitate signal intensity of labeled tissue; (f) converting tissue signal intensity units to hybrid-per-area units by (signal intensity/label-target DOL).

In one embodiment, there is provided a method of quantitative immunohistochemistry comprising: (a) contacting a sample comprising a tissue sample with at least a first and a second labeled targeting hybrid under conditions suitable for binding of the hybrid to a target on or within the tissue; (b) contacting the labeled tissue sample with a population of at least a first and a second population of quantitative labeled oligospheres bearing the same label as the labeled targeting hybrids applied to the tissue; (c) analyzing the sample using a microscope equipped with an appropriate fluorescent filter to observe the fluorescent signal of the labeled cells and microspheres, using a camera and imaging software to obtain representative images of the sample; (d) utilizing image-analysis software to create a signal-to-noise threshold and intensity standard curve using fluorescent oligospheres; (c) utilizing the signal intensity data provided by the labeled oligospheres to quantitate signal intensity of labeled tissue; (f) converting tissue signal intensity units to hybrid-per-area units for each label-target hybrid applied by (signal intensity/label-target Label Per Event (LPE)). The microscope may be, for example, a conventional inverted fluorescent microscope, a high-content scanning microscope, or a cytometric microscope.

Other embodiments provide methods of quantitative Enzyme-Linked ImmunoSorbent Assay (ELISA) comprising: (a) contacting a sample with a labeled targeting hybrid in a microplate under conditions suitable for binding of the hybrid to a target presented by the sample; (b) introducing quantitative labeled oligospheres to the microplate; (c) analyzing the microplate using a fluorimeter, luminometer, or spectrophotometer to determine labeling intensity of the sample and the oligospheres; and (d) utilizing the signal intensity data provided by the labeled oligospheres to convert sample labeling intensity to known number of targets per cell based on oligosphere Label Per Event (LPE). The method may further comprise applying a detection reagent to the samples to visualize the label. The detection reagent may be, for example, a fluorescent, luminescent, or colorimetric enzymatic substrate.

In other aspects, the targeting agent may be attached to the microsphere. For example, one embodiment provides a method of quantitative microsphere-based targeting assay comprising: (a) contacting a population of unlabeled oligospheres with increasing titrations of a labeling construct; (b) introducing quantitative targeting oligospheres to a sample under conditions suitable for binding of the labeling construct to a target on or within the sample; (c) applying a detection reagent to all samples to visualize the binding of the target to the oligospheres; (d) analyzing the oligospheres using a cytometer or particle analyzer; (e) analyzing a population of quantitative oligospheres using the cytometer or particle analyzer; and (e) utilizing the signal intensity data provided by the quantitative oligospheres to convert intensity of labeled targeting oligospheres to known number of targets per sphere. The detection reagent may comprise, for example, a fluorescent antibody reactive with the target, or a first antibody reactive with the target and a fluorescent second antibody reactive with the first antibody.

The method may be multiplexed by using additional (e.g., 2, 3, 4, 5, 6, 7, 8, 9, 10, 11, 12, 15, 20, 25 or more) labeled targeting hybrids and labeled oligospheres. For example, the method of quantitative flow cytometry may comprise: (a) contacting the sample with at least a first and a second labeled targeting hybrid, wherein the first labeled targeting hybrid comprises an antibody and a fluorescent label that differ from the antibody and the fluorescent label of the second labeled targeting hybrid, under conditions suitable for binding of the first and the second labeled targeting hybrid to their respective binding sites on the cells; (b) analyzing the cells bound to labeled targeting hybrid in the sample in the flow cytometer; (c) analyzing at least a first and a second population of quantitative oligospheres, wherein the fluorescent labels of the first and the second populations of quantitative oligospheres differ from each other, but are the same as the fluorescent label of either the first or the second labeled targeting hybrid, in a flow cytometer; (d) determining the Geometric Mean Fluorescent Intensity (GMFI) versus LPE trendline from the GMFIs of at least two different populations of quantitative oligospheres; (e) determining the LPE for the one or more cell populations bound to either the first or the second labeled targeting hybrid from the GMFI versus LPE trendlines; and (f) quantifying the amount of the first or the second labeled targeting hybrid bound per cell. In some embodiments, the first or the second labeled targeting hybrid comprise an antibody:oligonucleotide targeting construct, and bind an antigen on the cells.

Any of the compositions disclosed herein may be provided in a kit. In certain embodiments, the kit comprises a composition comprising a titrated population of labeled oligospheres, wherein the titrated population of labeled oligospheres comprises at least 2, 3, 4, 5, 6, 7, 8, 9, 10, 11, or 12 subpopulations of labeled oligospheres, wherein each of the subpopulations of labeled oligospheres is hybridized to a different amount of labeling construct. In certain aspects, the titrated population of labeled oligospheres are combined in a single container in the kit. In other aspects, the subpopulations are provided of labeled oligospheres are provided in separate containers in the kit. In some embodiments, the kit comprises an antibody:oligonucleotide targeting construct and/or a labeling construct.

The sample may be any sample that is suspected of containing an analyte of interest. In certain aspects the sample may be obtained from a subject who is being screened for the presence or absence of an antigen of interest. In another aspect, the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan. In certain embodiments, the sample is a blood sample. The blood sample may be a whole blood sample or it may be separated into various blood components. In certain embodiments, the sample is from the buffy coat.

The samples may contain cells that express antigens recognized by one or more antibody:ligand targeting constructs. In certain embodiments, the cells are immune cells. The immune cells may be myeloid cells, such as monocytes, macrophages, and dendritic cells (DC), or lymphoid cells, such as T cells, NK cells, B cells, and lymphoid DC. In other embodiments the cells are cancer cells.

The antibody in the antibody:ligand targeting construct may comprise an antibody that specifically binds to any antigen of interest. In certain embodiments, the antigen of interest is an antigen that is characteristic of immune cells or cancer cells. Non-limiting examples of antigens characteristic of immune cells are CD4, CD8, CD28, CD43, CD56, and CD62L. In particular embodiments, combinations of antibody:ligand targeting constructs are employed. For example, in one aspect a first antibody:oligonucleotide targeting construct comprises an antibody that binds to CD4 and the second antibody:oligo targeting construct comprises an antibody that binds to CD8. Additional antibody:ligand targeting constructs may be employed, such as at least a third and a fourth different antibody:ligand targeting construct under conditions suitable for binding of the third and the fourth antibody:ligand targeting constructs to their respective antigens on the cells. Thus, for example, the first antibody:oligonucleotide targeting construct comprises an antibody that binds to CD4, the second antibody:oligonucleotide targeting construct comprises an antibody that binds to CD8, the third antibody:oligonucleotide targeting construct comprises an antibody that binds to CD43, and the fourth antibody:oligonucleotide targeting construct comprises an antibody that binds to CD62L.

As used herein, the term "bioconjugate" means a construct in which at least one biomolecule is attached to another moiety. In certain embodiments, bioconjugates may be proteins attached to ligands, including oligonucleotides. In other embodiments, bioconjugates may be ligands attached to a labeling moiety. Attachment may occur by any of the linker chemistries discussed herein. Bioconjugates include, for example, targeting constructs and labeling constructs.

As used herein, the term "targeting construct" means a construct in which a targeting moiety is attached to a ligand. In certain embodiments, the targeting construct is an antibody attached to an oligonucleotide. In other embodiments, the targeting construct is a non-antibody protein with the desired affinity for a particular binding target attached to an oligonucleotide. As used herein, an "[X]:[Y] targeting construct" refers to a targeting construct in which a targeting moiety of type [X] is attached to a ligand of type [Y].

As used herein, the term "labeling construct" means a construct in which a labeling moiety is attached to a ligand. In certain embodiments, the labeling construct is a small molecule fluorophore attached to an oligonucleotide, optionally via a dextran or other scaffold. In other embodiments, the labeling construct is a radionucleotide attached to an oligonucleotide, optionally via a dextran or other scaffold. As used herein, an "[U]:[V] labeling construct" refers to a labeling construct in which a labeling moiety of type [U] is attached to an oligonucleotide of type [V]. Where [V] is stated as oligonucleotide, any sequence of oligonucleotide is contemplated.

As used herein, the term "labeled targeting hybrid" means a targeting construct and a labeling construct, in which the ligands are oligonucleotides, and in which the respective oligonucleotides have annealed to form a hybrid. In certain embodiments, this is an antibody:oligonucleotide targeting construct hybridized to a complementary oligo:fluorophore labeling construct. As used herein, an "[M]::[N] labeled targeting hybrid" refers to a labeled targeting hybrid in which a targeting construct containing a targeting moiety of type [M] is hybridized to a labeling construct containing a labeling moiety of type [N]. As used herein, the term "antibody" is intended to refer broadly to any immunologic binding agent, such as IgY, IgG, IgM, IgA, IgD and IgE, and includes monoclonal antibodies, polyclonal antibodies, antibody fragments (Fab', Fab, F(ab')$_2$, single domain antibodies (DABs), Fv, scFv (single chain Fv), and the like, and chimeric antibodies.

Any of the methods disclosed herein may be automated in whole or in part. In some embodiments, computer executable instructions or a computer readable medium comprising computer executable instructions, are provided for carrying out the steps of the methods disclosed herein. In certain aspects, the computer executable instructions comprise all or part of one or more of the algorithms in FIGS. 11A-11B.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1C. (FIG. 1A) shows the antibody-oligonucleotide conjugation by HyNic-4FB chemistry: (i) Succinimidyl-6-hydrazinonicotinamide acetone hydrazone (S-HyNic) is added to purified antibody (Ig), allowing succinimydyl groups to react with free amino sites on lysine groups at the antibody hinge region to form Ig-HyNic (iii). Similarly, succinimidyl-4-formylbenzamide (S-4FB) reacts with amino-modified oligonucleotide (ii) resulting in 4FB-oligo (iv). The HyNic- and 4FB-modified biomolecules are then combined in the presence of aniline, which catalyzes the HyNic-4FB reaction, resulting in formation of a covalent hydrazone bond (v) and a stable antibody-oligonucleotide bioconjugate. (FIG. 1B) shows a scheme for the preparation of an oligo:fluorophore labeling construct. To prepare a 1:1 oligo:dextran conjugate (i), a 70 kDa amino-dextran bearing approximately 20 amino groups per dextran is first reacted with an amount of S-HyNic sufficient to create 3-4 HyNic moieties per dextran, leaving >10 amino groups available for downstream NHS-fluorophore labeling. In order to limit the final average oligo-per-dextran to <1, a stoichiometrically-limiting amount of 4FB-modified oligonucleotide is then added to the HyNic-dextran, in a pH 5.0 buffer containing 10% aniline catalyst (v/v). Following the 4FB/HyNic reaction, the oligo-conjugated amino-dextran is purified first by size exclusion chromatography (SEC) to remove excess oligo, and then by ion exchange column (IEC) to remove unconjugated dextran. To the amino-dextran-oligo is then added a molar excess of NHS-ester fluorophore (ii). Excess fluorophore is removed by dialysis, and the final oligo-dextran-fluorophore product is characterized by A260 assay to confirm oligo-dextran ratio and fluorophore degree of labeling (DOL). (FIG. 1C) illustrates multiplexed cell labeling using labeled targeting hybrids. Antibody:oligonucleotide targeting constructs are briefly hybridized in solution to complementary fluorophore:oligonucleotide labeling constructs (i) to form individual antibody::fluorophore labeled targeting hybrids (ii). The labeled targeting hybrids may then be used to label cells for a single antigen, or as shown here, combined and used for multiplexed cell labeling (iii).

(FIG. 2A) To determine optimal oligo/oligo ratio for hybridization of labeled targeting hybrids, a titration of oligo:fluorophore labeling construct was performed by adding 0.5-10 molar equivalents of oligo-1':Dy490 labeling construct to a fixed amount (6 pmol) of antibody:oligo targeting construct, αCD4:oligo-1, in a small volume of Phosphate Buffered Saline (PBS). The labeled targeting hybrids were then added to viable splenocytes to label CD4 antigen, and the labeled cells were analyzed by flow cytometry. Results showed the population of CD4+ cells to be similar for all titrations; however, nonspecific background caused by addition of excess fluorophore increased above 1.0 oligo/oligo equivalents. A titration of 0.5 molar equivalents oligo:fluorophore labeling construct was used for subsequent assays. (FIG. 2B) Hybridization was conducted either in solution, by combining antibody:oligo and oligo:fluor in a small volume of PBS and then using the construct to label cells, or in situ by first cell-labeling with antibody:oligo and then introducing oligo:fluors for hybridization. Results showed very similar positive labeling percentages for hybridization in solution (dark green histogram) vs in situ (light green tinted histogram). Unstained cells are shown as a background control. (FIG. 2C) Blocking hybridization using an unmatched oligo sequence (blue histogram) was successful, an indication that antigen labeling is highly specific using hybridized labeling constructs (green histogram). Blocking was conducted using a 5-fold molar excess of oligo:fluor as shown in panel (A). The blocking oligo did not prevent nonspecific binding of the oligo:fluor, as evidenced by similar levels of dye background. (FIG. 2D) Time and temperature conditions for hybridization were investigated, using 15-60 minute hybridization at 4° C. (blue histograms), 24° C. (gray histograms), or 37° C. (pink histograms). Results indicate that hybridization occurs with little variation over this range of time and temperature conditions. (FIG. 2E) Adjusting signal intensity by increasing fluorophore degree of labeling (DOL) from 3-15 fluors per oligo:fluorophore labeling construct shows optimal signal to background at DOL~7, with decreasing positive peak resolution at DOL<7 and marked decreased in median fluorescence intensity (GMFI) at DOL>10, most likely due to fluorescence self-quenching.

(FIG. 3B) Multiplexed cell labeling data. 2-color dot plots depict multi-antigen labeling data for cells stained with four antibody::fluorophore labeled targeting hybrids as previously described. The staining distributions seen here provide evidence that the system is specific and sensitive, allowing for accurate gating and analysis of immune cell phenotypes. (I) CD4+ and CD8+ T-cell populations within the gated lymphocyte population were clearly defined. (ii) The majority (~74%) of lymphocytes are CD43+, and nearly all CD4+ cells were CD43+. Two CD43high populations were evident, either CD4− (34%) or CD4+ (7%). (iii) Most lymphocytes were CD62L+ (~75%). (iv) Gating of CD4+ lymphocytes and display of CD4+/CD43 vs CD4+/CD62L distribution reveals that 30% of CD4+ T-lymphocytes were CD4+/CD43+/CD62L−, while 64% were triple-positive for all 3 antigens. Only a small minority of CD4+ cells were negative for CD43 (6%) or were double-negative for CD43 and CD62L (2%). (v) A defined population of CD8+/CD43+ cells was visible, as well as a CD8− population of CD43+ lymphocytes, either CD43low (29%) or CD43high (15%). (vi) A distinct population of CD8+/CD62L+ cells are visible (26%). (vii) Most CD43+ lymphocytes are CD62L+; a distinct population of CD43high CD62L+ cells was evident (33%). (viii) Gating of CD8+ lymphocytes and display of CD4+/CD43 vs CD4+/CD62L distribution reveals that the majority (93%) of CD8+ lymphocytes were CD43+/CD62L+.

(FIG. 4A) Schematic showing interchangeable hybridization principle. Antibody:oligo targeting construct (Ig:oligo-A) can be hybridized to any oligo-A':fluorophore labeling construct, resulting in antibody::fluorophore labeled targeting hybrid in a variety of spectra. (FIG. 4B) Universal-oligo constructs were used to label cells for control antigen CD4 in four distinct spectra. Results show that labeling percentages were very similar across fluorescent channels for both antigens, indicating that antibodies can be effectively labeled in a variety of spectra using the universal-oligo approach. (FIG. 4C) CD4:oligonucleotide and CD8:oligonucleotide targeting constructs were combined for double-staining of cells in two fluorophore combinations: (i) xCD4::Dy490+xCD8::Dy649; (ii) xCD4::Dy405+xCD8::Dy549. In order to block oligo-mediated exchange of oligo:fluorophores when constructs were mixed, an excess of unmodified oligo-A was added to each construct immediately following hybridization in solution. While exchange was observed to be low (~1%) without blocking oligo at typical staining conditions (data not shown), with the addition of blocking oligo the exchange dropped to a negligible ~0.5%.

FIG. 5A-5D. Preparation and analysis of quantitative oligospheres. (FIG. 5A) Method I, parallel labeling of quantitative oligospheres alongside cells. First, oligonucleotide-saturated microspheres (μ) are hybridized to discrete, known amounts of complementary oligo:fluorophore labeling construct at increasing titrations (1-4). Amount of oligo-fluorophore label per microsphere event (LPE) is separately confirmed by fluorimetry. The labeled oligospheres are then added to cells which have been labeled with antibody-fluorophore targeting hybrids. The labeled oligospheres and cells are then cytometrically analyzed. (FIG. 5B) Method II, combined labeling of quantitative oligospheres in solution with cells. First, oligonucleotides are conjugated to microspheres (μ) at increasing, known surface saturations (1-4). The oligospheres are added to cells which have been incubated with antibody-oligo targeting constructs. The combined oligospheres and cells are then labeled in solution followed by cytometric analysis. (FIG. 5C) Fluorometric analysis of four oligosphere populations hybridized with increasing titrations of labeling construct (1-4, labeled low-high) as in FIG. 5A. Labeling construct Per oligosphere Event (LPE) is determined by measuring oligosphere fluorescence for a sample of oligospheres vs a standard curve of labeling construct in solution (not shown). The oligospheres are then counted (not shown). LPE=[(mol labeling construct per sample×6E23 molecules per mol)/number oligospheres per sample]. (FIG. 5D) Cytometric analysis of four oligospheres populations shown in FIG. 5C, 1-4, labeled low-high (solid filled histograms). Increasing LPE translates to increasing fluorescence when cytometer fluorescence data are visualized by analysis software. Oligosphere singlets were gated (not shown) and data histograms were overlaid with a histogram showing unlabeled microsphere signal (autofluorescence, dashed open histogram).

FIGS. 6A-6D. Multiplexed Quantitative Flow Cytometry. Viable murine splenocytes (filled histograms) were probed using four distinct labeling hybrids: anti-CD4::Dy490 (FIG. 6A), anti-CD8::Dy549 (FIG. 6B), anti-CD43::Dy649 (FIG. 6C), and anti-CD62L::Dy405 (FIG. 6D). Quantitative fluorophore-hybridized oligospheres (open histograms) were labeled and analyzed with cells to quantify multiple surface antigens.

FIGS. 7A-7D. ABC Calculations. Geometric Mean Fluorescence Intensities (GMFIs) were determined for quantitative oligospheres (circles) in each fluorescent channel using cytometric data analysis software. Log 10 GMFIs were plotted vs log known fluorescent Label Per oligosphere Event (LPE), which were previously determined fluorimetrically (not shown). Cellular populations of interest (stars) were gated and GMFIs were determined using cytometric data analysis software. Antibody Binding per Cell (ABC) A 1:1 label:antibody ratio is assumed in this system; therefore, LPE=ABC, and thus ABC can then be determined from GMFI using the equations shown. Cellular data points shown represent geometric mean ABC for populations of interest (CD4+, CD8+, CD43$^{LO}$, CD43$^{HI}$, CD62L+).

FIGS. 9A-9C. Oligospheres and Cells Labeled in Combination. Quantitative oligospheres (open histograms) and cells (filled histograms) were labeled in combination as shown in FIG. 5B. Results show that labeling in combination is feasible and produces distinctly labeled cellular and oligosphere populations. (FIG. 9A) Distinct populations of oligospheres and lymphocytes shown in a FSC vs SSC scatter plot. (FIG. 9B) Fluorescent (Alexa Fluor 488) lymphocytes displaying CD4– and CD4+ populations. (FIG. 9C) Histogram overlay of oligosphere (black) and cellular (gray) data.

FIGS. 10A-10B. Quantitation of ABC$_{CD4}$ Using Commercial Reagents. Commercial quantitative fluorescent microspheres (BD QuantiBrite PE) were used to quantify ABC$_{CD4}$ using similar methodology and the same monoclonal antibody (GK1.5) used for ABC$_{CD4}$ quantitation using novel quantitative oligospheres. (FIG. 10A) Commercial microspheres and anti-CD4:PE stained cells were cytometrically analyzed to obtain GMFI data. (FIG. 10B) Microsphere Log 10 GMFI plotted vs Log 10 PE molecules per microsphere (lot-specific data provided by manufacturer). The equation generated by the microsphere standard curve was then used to quantify mean CD4+ according to the manufacturer protocol. ABC$_{CD4}$ data were very similar for commercial vs novel method (29741 vs 28824 CD4 antibody per cell).

(FIG. 11A) Flowchart for Algorithm I (calculation of standard curve from oligosphere data). (FIG. 11B) Flowchart for Algorithm II (calculation of Antibody Binding per Cell, ABC).

FIGS. 12A-12C. Spectral Compensation. Fluorophore-hybridized oligospheres were used to spectrally separate two adjacent fluorescent channels (FL1, FL2) using a conventional cytometer (BD LSRII) and commonly used analysis software (FlowJo). (FIG. 12A) Oligospheres are recognized by FlowJo Compensation Wizard software function, which auto-gated the oligospheres for singlets, FL1/FL2 positive and FL1/FL2 negative populations according to common methodology. The Compensation Wizard created a compensation correction matrix (not shown) which was then applied to correct the mixed two-color oligosphere sample shown below. (FIG. 12B) Uncompensated mixed sample of FL1+ or FL2+ oligospheres. Uncompensated data indicate 2 populations of FL1+ FL2+ oligospheres rather than separate, single-fluorophore spheres. (FIG. 12C). Compensated mixed sample of FL1+ or FL2+ oligospheres. The compensated data correctly show two separate, single-fluorophore oligosphere populations (either FL1+ or FL2+, not FL1+ FL2+).

FIGS. 14A-14B. Cytometer Calibration. Fluorophore-hybridized oligospheres of a single color and multiple intensities (FIG. 14A) were compared to commercial fluorescent microspheres (FIG. 14B) in terms of fluorescent peak resolution and distribution to evaluate whether oligospheres may be used for instrument calibration. Oligosphere peaks were well distributed, but resolution was somewhat lower than commercialized microspheres. As noted in FIG. 13, the inventors plan to improve resolution for oligospheres in the future by utilizing alternative amino-functionalized microspheres as a starting point, that may improve resolution of resulting fluorescent signals.

DESCRIPTION OF ILLUSTRATIVE EMBODIMENTS

Figure 1A:
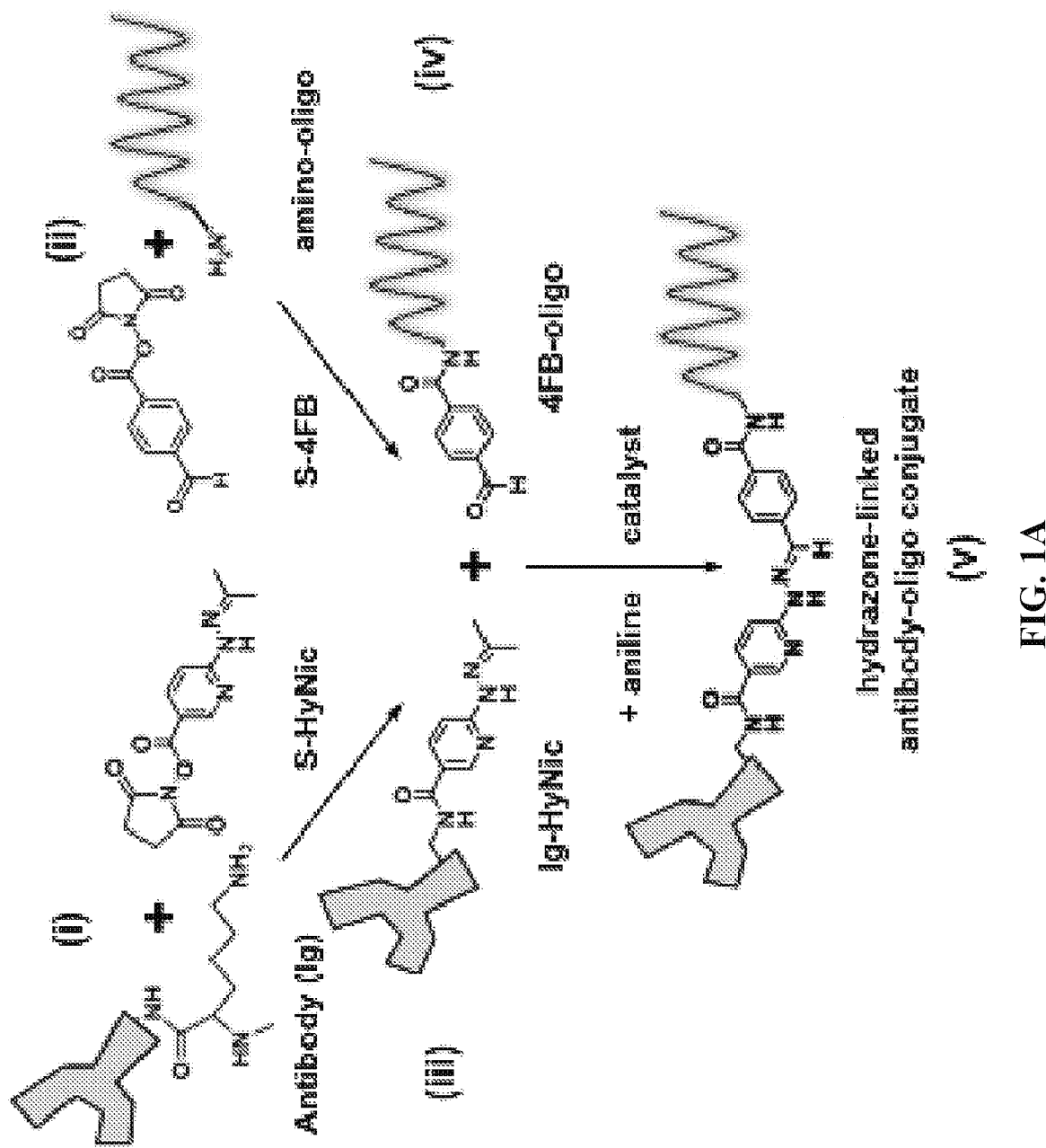

Methods and composition for quantitative flow cytometry and quantitative CyTOF are provided herein. Particular embodiments utilize a DNA-directed assembly strategy for cellular labeling. In certain aspects, antibody:oligonucleotide targeting constructs are hybridized to complementary oligonucleotide:fluorophores labeling constructs in solution to create a labeled targeting hybrid. The antibody::fluorophore labeled targeting hybrid is then used to label cellular antigens. Fluorophore-hybridized oligospheres utilizing the same fluorophore used to label the hybridized antibody:: fluorophore labeled targeting hybrid are added to the cytometric analysis in order to convert relative units of fluorescence to quantitative measures of Label Per Event (LPE). LPE is then used to calculate the number of Antibodies Bound per Cell (ABC) based on the known label-target ratio established during the construct ligation step.

A. Flow Cytometry

Various embodiments described herein provide a quantitative approach to flow cytometry. Flow cytometry is an optical technique that analyzes particles in a fluid mixture based on the particles' optical characteristics using an instrument known as a flow cytometer. Flow cytometers hydrodynamically focus a fluid suspension of particles into a thin stream so that the particles flow down the stream in substantially single file and pass through an examination zone. A focused light beam, such as a laser beam illuminates the particles as they flow through the examination zone. Optical detectors within the flow cytometer measure certain characteristics of the light as it interacts with the particles. Commonly used flow cytometers can measure forward light scatter (generally correlated with the refractive index and size of the particle being illuminated), side light scatter (generally correlated with the particle's internal complexity and granularity), and particle fluorescence at one or more wavelengths.

The types of "particles" that may be analyzed by a flow cytometer include cells as well as man-made microspheres or beads. Fluorescent microspheres for use as calibrants for semi-quantitative flow cytometry are generally known in the art and may be obtained from manufacturers such as Becton Dickinson (BD), Spherotech, and Bangs Laboratories. Protein-binding microspheres may also be analyzed via flow cytometry and are available from manufacturers such as Life Technologies (Invitrogen) and EMD-Millipore (Luminex).

Conventional methods of multiplexed flow cytometry are invaluable to clinical and research laboratories, and are used for a wide range of applications from studies of cellular biology to disease diagnosis. However, due to existing constraints placed by conventional methods and reagents, flow cytometry has almost universally been practiced using subjective analysis parameters. The quantitative approach to flow cytometry described herein provide researchers more flexibility in experimental design and a streamlined approach to quantitation; thus, this is an important development in the field that addresses many of the current challenges to conventional flow cytometry.

B. Single-Cell Mass Cytometry

Embodiments described herein may also be used to provide a quantitative approach to single-cell mass cytometry (CyTOF). CyTOF is another platform that can be used to simultaneously analyze multiple parameters of individual cells in a sample (Bendall et al., Science, 332:687-696 (2011)). The work flow is comparable to that of fluorescence flow cytometery. In general, antibodies labeled with heavy metals or transition element isotopes are used to bind target epitopes on or within cells. The antibody-bound cells are then vaporized, such as by spraying single-cell droplets into an inductively coupled argon plasma at approximately 5500 K. Vaporization induces ionization of the cells atomic constituents. The elemental ions are then sampled by a Time-Of-Flight (TOF) mass spectrometer and quantified. The signal for each metal/isotope that labeled a particular cell are thereby detected.

C. Antibody:Oligonucleotide Targeting Constructs

As discussed above, labeled antibodies are employed in both flow cytometry and CyTOF platforms. Although there are a variety of commercially available antibodies biochemically conjugated to fluorochromes, the majority of clones are only available in a limited number of colors, often in the same standard fluorochrome such as fluorescein. The interchangeable "Mix and Match" hybridization strategy of the antibody:oligonucleotide targeting constructs disclosed herein, offers a significant improvement over existing methods. In particular, antibody:ligand targeting constructs facilitate greater interchangeability than afforded using direct antibody-fluorophore conjugates, and provide a more convenient solution for multiplexed labeling that indirect labeling techniques based on biotin-streptavidin chemistry.

Antibodies are glycoproteins belonging to the immunoglobulin superfamily. Antibodies typically are made of two large heavy chains and two small light chains. There are several different types of antibody heavy chains, and several different kinds of antibodies, which are grouped into different isotypes (IgA, IgD, IgE, IgG and IgM in mammals) based on which heavy chain they possess. Though the general structure of all antibodies is very similar, a small region known as the hypervariable region at the tip of the protein is extremely variable. This allows for enormous diversity of antibodies to recognize a wide variety of antigens.

The antibody portion of the antibody:ligand targeting construct may comprise any immunologic binding agent, such as IgG, IgM, IgA, IgD and IgE or Fab', Fab, F(ab')$_2$, single domain antibodies (DABs), Fv, and scFv (single chain Fv) fragments thereof. In certain aspects the antibody is a monoclonal antibody. Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells. Following immunization, somatic cells with the potential for producing antibodies, specifically B lymphocytes (B cells), are selected for use in the MAb generating protocol. These cells may be obtained from biopsies spleens, tonsils or lymph nodes, or from a peripheral blood sample. The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like. Fragments of monoclonal antibodies can be obtained by enzymatic digestion, cleavage, or chemical reduction of monoclonal antibodies. Alternatively, monoclonal antibody fragments may be synthesized using an automated peptide synthesizer or produced recombinantly.

The antibody may be conjugated to a ligand using a variety of techniques. One approach is the use of HyNic-4FB. Briefly, succinimidyl-6-hydrazinonicotinamide acetone hydrazone (S-HyNic) is added to purified antibody, converting free amino groups on lysines near the antibody hinge region to HyNic moieties. Similarly, succinimidyl-4-formylbenzamide (S-4FB) added to amino-modified oligo converts amino groups to 4-FB moieties. When combined in the presence of aniline catalyst, the HyNic and 4-FB sites on modified biomolecules react to produce a stable, covalent hydrazone bond and forming the antibody:oligo conjugate. Following purification using a nickel column, this process results in >95% yield of antibody:oligo conjugate.

The antibody may alternatively be conjugated to a ligand according to a variety of bioconjugation techniques known to those in the art. These include modification of amine, carbonyl, hydroxyl, sulfhydryl, or other available groups on biomolecules to incorporate linker moieties, with subsequent reaction of the linker moieties to form a conjugate. Linker pairs may include (strept)avidin-biotin, azide-acrylamide, thiol-maleimide, and others (Hermanson, Bioconjugate Techniques, Academic Press 1996). However, modification and linkage of biomolecules may affect biological activity of either the antibody and/or the oligonucleotide, so milder reactions proceeding at neutral pH, temperature and salt conditions (e.g., hydrazone chemistry) are preferable to reactions requiring harsh conjugation conditions (e.g., sulfhydryl reduction followed by thiol-maleimide modification).

Herein, a ligand generally comprises an oligonucleotide linked to an antibody, although alternative ligands (e.g. peptides or haptens) may be used. Oligonucleotides conjugated to the antibodies are designed to hybridize to complementary, labeled oligonucleotides. As used herein, "hybridization," "hybridizes" or "capable of hybridizing" is understood to mean the forming of a double- or occasionally triple-stranded molecules, or a molecule with partial double or triple stranded nature. The term "anneal" as used herein is synonymous with "hybridize." An important parameter for describing oligonucleotides and their interaction with complementary sequences is the so-called $T_m$, the temperature at which 50% of the nucleic acid duplex formed by hybridization of complementary sequences is dissociated. The $T_m$ varies according to a number of sequence dependent properties including the hydrogen bonding energies of the canonical pairs A/U-T and G-C (often measured as the GC percentage or base composition), the stacking free energy and, to a lesser extent, nearest neighbor interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature.

In multiplex assays, problems in hybridization occur when the hybrids are allowed to form under hybridization conditions that include a single hybridization temperature that is not optimal for correct hybridization of all oligonucleotide sequences of a set. Mismatch hybridization of non-complementary probes can occur, forming duplexes with measurable mismatch stability. Mismatching of duplexes in a particular set of oligonucleotides can occur under hybridization conditions where the mismatch results in a decrease in duplex stability that results in a higher Tm than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Accordingly, methods of Tm normalization have been employed in an effort to maintain equivalent hybridization stringency between nucleic acids having disparate Tms. Some of these methods include the use of non-natural nucleic acid backbones (LNA for example) or the use of hairpin probes.

Typically, it will be desirable that the oligonucleotides conjugated to the antibody are not cross-reactive with other nucleic acids that may be present in a sample. And, in multiplexed application, it will also be desirable that an oligonucleotide conjugated to one antibody is not cross-reactive with the labeled oligonucleotide probe for another antibody:oligonucleotide conjugate. There are a number of different approaches for selecting complementary oligonucleotide sequences for use in multiplexed hybridization assays. The selection of sequences that can be used as zip codes or tags in an addressable array has been described in the patent literature in an approach taken by Brenner and co-workers (U.S. Pat. No. 5,654,413, incorporated herein by reference). In addition, U.S. Pat. No. 7,226,737, incorporated herein by reference, describes a set of 210 non-cross hybridizing tags and anti-tags. U.S. Published Application No. 2005/0191625, incorporated herein by reference, discloses a family of 1168 tag sequences with a demonstrated ability to correctly hybridize to their complementary sequences with minimal cross hybridization.

The nucleic acids disclosed herein may be prepared by any technique known to one of ordinary skill in the art, such as for example, chemical synthesis, enzymatic production, or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by U.S. Pat. No. 5,705,629, incorporated herein by reference. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as Polymerase Chain Reaction (PCR) (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001).

The oligonucleotides may include nucleotide isomers or base analogs. A nucleic acid sequence may comprise, or be composed entirely of, an analog of a naturally occurring nucleotide. Nucleotide analogs are well known in the art. A non-limiting example is a "Peptide Nucleic Acid," also known as a "PNA," "peptide-based nucleic acid analog," or "PENAM," described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. PNAs generally have enhanced sequence specificity, binding properties, and resistance to enzymatic degradation in comparison to molecules such as DNA and RNA (Egholm et al., 1993; PCT/EP/01219). Another non-limiting example is a Locked Nucleic Acid or "LNA." An LNA monomer is a bi-cyclic compound that is structurally similar to RNA nucleosides. LNAs have a furanose conformation that is restricted by a methylene linker that connects the 2'-O position to the 4'-C position. Yet another non-limiting example is a "polyether nucleic acid," described in U.S. Pat. No. 5,908,845, incorporated herein by reference. In a polyether nucleic acid, one or more nucleobases are linked to chiral carbon atoms in a polyether backbone.

D. Oligospheres

Methods described herein can be applied to create quantitative ligand-surfaced microspheres using any type of ligand (e.g. oligospheres, peptides, haptens). However, various embodiments disclosed herein use oligospheres as quantitative reference standards. Oligospheres comprise microspheres conjugated to oligonucleotides. In some embodiments, the oligonucleotides will be conjugated substantially uniformly to the entire surface of the oligosphere (as in FIG. 5A). In other embodiments, the oligonucleotides will be conjugated at increasing titrations to the surface of the oligosphere (as in FIG. 5B).

The oligonucleotides may be conjugated to the microspheres according to a variety of techniques known to those in the art. Similar to antibody-oligo conjugation, the oligonucleotide-microsphere conjugation procedure may involve modification of amine, carboxyl, hydroxyl or other reactive groups on oligonucleotides and microsphere surfaces in order to incorporate linker moieties for subsequent conjugation reactions; linker chemistry may include HyNic/4FB (hydrazone), (strept)avidin/biotin, phosphoramidite, octadinyl dU, and other chemistries. Alternatively, the microspheres may be pre-manufactured to present surface reactive groups to which reactive-group bearing oligo may be conjugated (e.g., amino- or streptavidin-modified microspheres). Typically, the oligonucleotides will be conjugated substantially uniformly to the entire surface of the oligosphere. In certain aspects, a non-reactive spacer sequence is placed between the microsphere and the region of the oligonucleotide that is complementary to the probe. Such non-reactive spacers may, for example, facilitate conjugation to the microsphere and/or reduce steric hindrance of the oligonucleotide. Examples of non-reactive spacers include Poly Ethylene Glycols (PEGs) or oligonucleotide domains designed for minimal cross-reactivity (e.g. poly-Thymine, "PolyT").

Figure 5A:
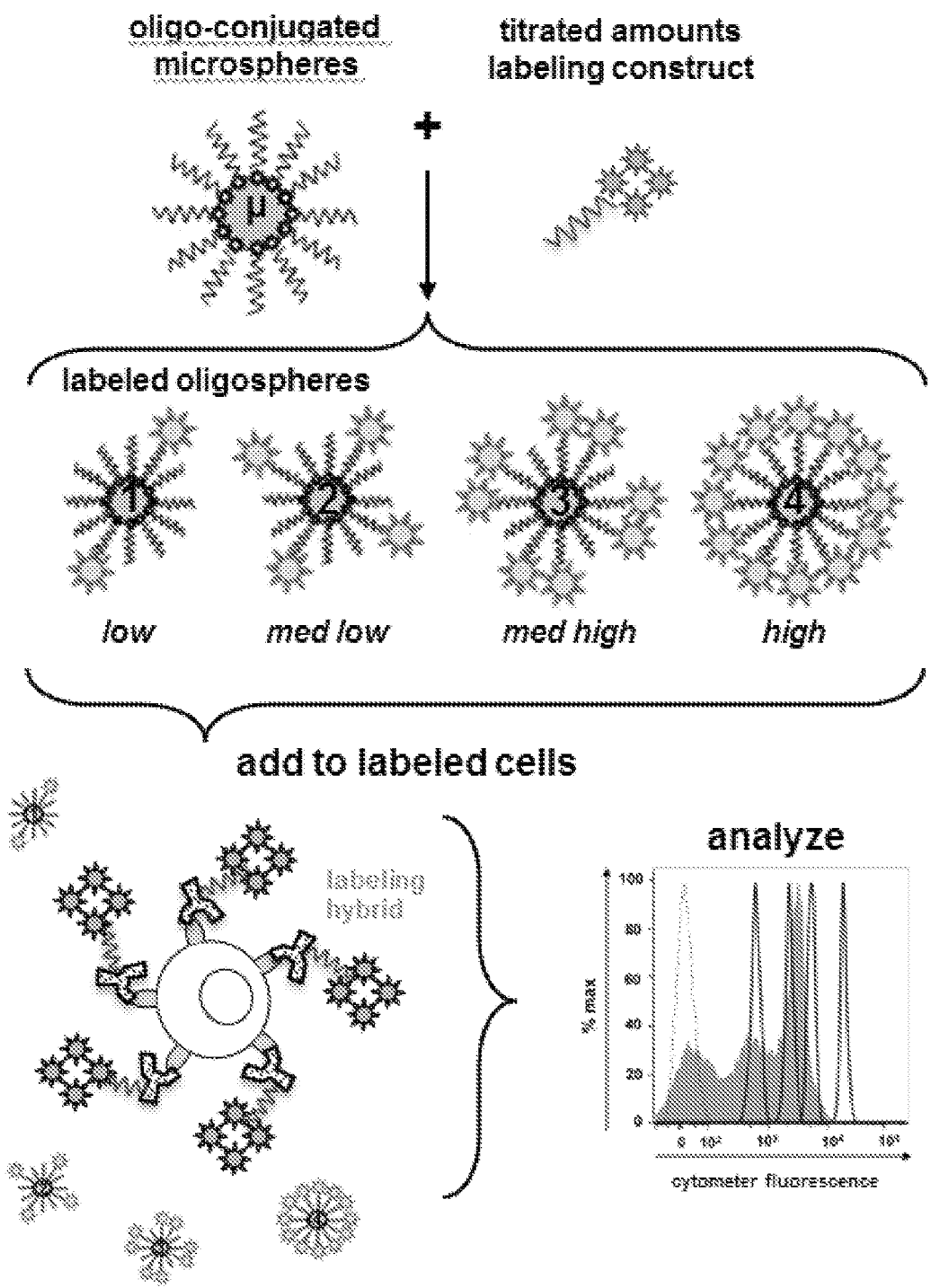
Figure 5B:
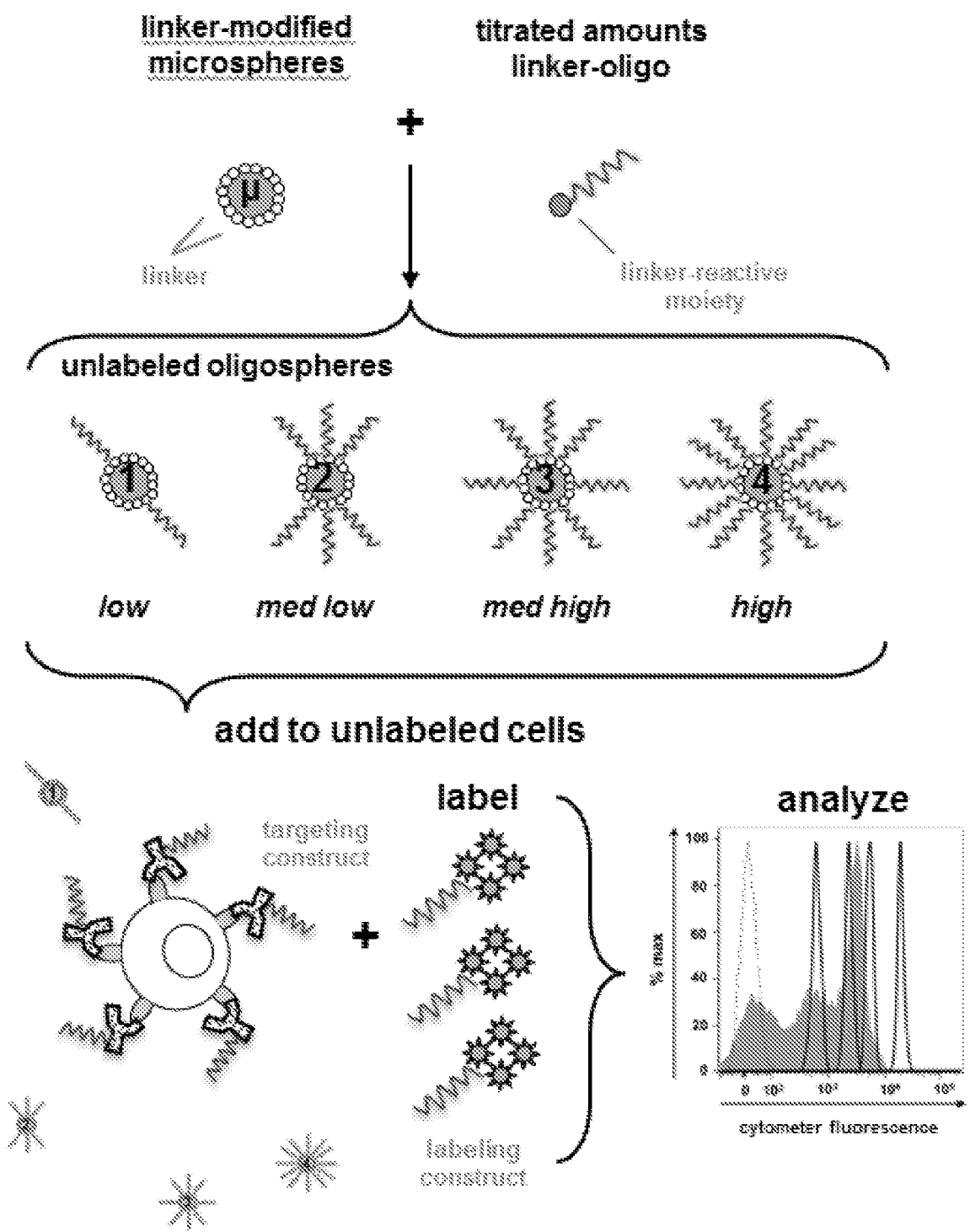

In certain embodiments, the oligospheres are hybridized to the same labeled oligonucleotide probe that is used to hybridize to the antibody:oligonucleotide targeting construct. Thus, the oligospheres and the cells in the assay are labeled with the same label. FIGS. 5A-5B illustrate two methods for preparation of a titrated population of quantitative oligospheres. As shown in FIG. 5A, oligonucleotides are conjugated to microspheres at surface saturation. A complementary oligo:fluorophore labeling construct is then added at increasing levels of titration, creating populations of fluorescent microspheres of increasing signal intensity. Following oligo:fluorophore hybridization, remaining (free) surface oligonucleotide may be passivated by the addition of unmodified complementary oligonucleotide to reduce non-specific reactivity of free oligo (data not shown). The populations of fluorophore-hybridized microspheres are then mixed, and can then be added to cells stained with antibody::fluorophore labeled targeting hybrid. As shown in FIG. 5B, oligonucleotides are conjugated to microspheres at increasing surface saturations, but are not yet labeled with complementary oligo:fluorophore. They are first combined with cells bearing targeting construct (i.e. antibody:oligo). Complementary oligo:fluorophore labeling construct is then added in sufficient amount to label both cells and oligospheres.

Using either preparation method allows the mixed sample of cells and quantitative oligospheres to be analyzed by flow cytometry, with the oligospheres providing an internal standard curve for quantitation of cellular ABC. Accordingly, the oligosphere data can be immediately and easily used for straightforward ABC calculation as described herein.

E. Analysis of Cells

Flow cytometry and CyTOF are valuable tools for study of cells. In particular, multiplexed cellular phenotyping is a principal strategy applied in immunology research. Surface antigens indicative of immune cell status are detected by multiplexed antibody labeling, the sample is analyzed by flow cytometry or CyTOF, and phenotypic subset identification is conducted. Using data analysis software, subsets are gated for inclusion in or exclusion from further analysis.

Various embodiments disclosed herein, address various challenges presented by conventional fluorescence flow cytometric methods by utilizing a DNA-Directed Assembly (DDA) strategy for cellular labeling. Antibody:oligonucleotide targeting constructs are hybridized to complementary oligo:fluorophore labeling constructs in solution to create a labeled targeting hybrid. The antibody::fluorophore labeled targeting hybrid is then used to probe cellular antigens. Fluorophore-hybridized microspheres added to the cytometric analysis are used to convert relative units of fluorescence to quantitative measures of Labeling construct Per Event (LPE). LPE is then used to calculate the number of Antibodies Bound per Cell (ABC). This approach can also be adapted to CyTOF analysis by replacing the fluorophore with a metal/isotope label.

Antibody:oligonucleotide targeting constructs comprising antibodies specific to various immune cell surface antigens can be used in multiplexed cellular phenotyping. Peripheral Blood Mononuclear Cells (PBMC) are comprised of cells of myeloid and lymphoid lineages. Myeloid cells include monocytes, macrophages, and dendritic cells. Lymphoid cells include T cells, NK cells, B cells, and lymphoid dendritic cells. The expression patterns of surface antigens in different immune cell types are known to those in the art. A description of some of these expression patterns is provided below.

Natural Killer cells (NK cells) are a type of cytotoxic lymphocyte. NK cells are activated in response to interferons or macrophage-derived cytokines, and they play a major role in the rejection of tumors and cells infected by viruses. NK cells are characterized by their lack of the T cell receptor (CD3) and their expression of CD56 on their surface. Accordingly, these characteristics may be used to separate NK cells from other cell types.

T cells play a role in cell-mediated immunity. One way in which T cells can be distinguished from other lymphocytes, such as B cells and NK cells, is by the presence on their cell surface of the T cell receptor. Activation of CD8+ T cells and CD4+ T cells occurs through the engagement of both the T cell receptor and CD28 on the T cell by the Major Histocompatibility Complex (MHC) peptide and B7 family members on an antigen presenting cell. Activation-associated surface antigen CD43 is expressed at distinct low and high levels, and lymphocyte homing molecule CD62L is expressed at a range of levels as it is degraded upon cellular activation. Monocytes also express CD4, but they can be distinguished from CD4+ lymphocytes, because monocytes also express CD14 on their surface.

In some aspects of the invention, the cells are mammalian cells, including cultured mammalian cells (e.g., murine or human tumor, stem, or immortalized cell lines), cells derived from laboratory rodents, or cells derived from human patient samples such as whole blood, fine-needle cellular aspirates, or biopsy tissue. In certain embodiments, the cell sample is derived from an environmental sample such as a water, soil, or air. In other embodiments, the sample is from a plant, bacteria, virus, fungi, protozoan, or metazoan.

F. Kits

The present invention also provides kits. Any of the components disclosed herein may be combined in a kit. In certain embodiments the kits comprise one or more of an targeting construct, a labeling construct, and/or ligand-surfaced microspheres.

In certain embodiments, the kit comprises a composition comprising a titrated population of labeled oligospheres, wherein the titrated population of labeled oligospheres comprises at least 2, 3, 4, 5, 6, 7, 8, 9, 10, 11, or 12 subpopulations of labeled oligospheres, wherein each of the subpopulations of labeled oligospheres is hybridized to a different amount of labeling construct. In certain aspects, the titrated population of labeled oligospheres are combined in a single container in the kit. In other aspects, the subpopulations are provided of labeled oligospheres are provided in separate containers in the kit. In some embodiments, the kit comprises an antibody:oligonucleotide targeting construct and/or a fluorophore:oligonucleotide labeling construct. In certain embodiments, the oligonucleotide in the fluorophore:oligonucleotide labeling construct is complementary to the oligonucleotides on the oligosphere and the antibody:oligonucleotide targeting construct.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the oligosphere subpopulations in a series are combined in a single container. In other embodiments, some or all of the oligosphere subpopulations in a series are provided in separate containers.

The kits of the present invention also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Selection of oligonucleotide sequences, antibodies, and fluorophores

Oligonucleotide sequences are shown in Table 1. Oligo pairs 1/1', 2/2', 3/3', and 4/4' were designed and validated by Feldkamp et al [7] to have low reactivity with unmatched oligo sequences, high melting temperature, stable and robust hybridization activity, and desirable hairpin formation characteristics (i.e., retain hairpins at higher temperatures, reducing oligo crosstalk between unmatched sequences). Oligo crosstalk was tested for pairs 1-4 by staining cells with a matrix of matched and unmatched antibody:oligo::oligo:fluor pairs, and observed undesirable crosstalk to be <2% in all cases. This has implications for multiplexed cell labeling (i.e., any number of antibody:oligos can be mixed together with oligo:fluors in solution without assay interference by crosstalk via oligo exchange).

TABLE 1

Oligonucleotide Sequences

| Oligo | Sequence | Bases | Tm (° C.) |
|---|---|---|---|
| oligo-1 | CCTGCGTCGTTTAAGGAAGTAC | 22 | 62.2 |
| oligo-1' | GTACTTCCTTAAACGACGCAGG | 22 | 62.2 |
| oligo-2 | GGTCCGGTCATAAAGCGATAAG | 22 | 62.2 |
| oligo-2' | CTTATCGCTTTATGACCGGACC | 22 | 62.2 |
| oligo-3 | GCTGACATAGAGTGCGATAC | 20 | 62.2 |
| oligo-3' | GTATCGCACTCTATGTCAGC | 20 | 62.2 |
| oligo-4 | TGTGCTCGTCTCTGCATACT | 20 | 63.5 |
| oligo-4' | AGTATGCAGAGACGAGCACA | 20 | 63.5 |
| oligo-A | GGAAGCGGTGCTATCCATCT | 20 | 71.1 |
| oligo-A' | AGATGGATAGCACCGCTTCC | 20 | 71.1 | oligo-1 (SEQ ID NO: 1), oligo-1' (SEQ ID NO: 2), oligo-2 (SEQ ID NO: 3), oligo-2' (SEQ ID NO: 4), oligo-3 (SEQ ID NO: 5), oligo-3' (SEQ ID NO: 6), oligo-4 (SEQ ID NO: 7), oligo-4' (SEQ ID NO: 8), oligo-A (SEQ ID NO: 9), oligo-A' (SEQ ID NO: 10)

In addition to oligo pairs 1/1'-4/4', novel oligo pair A/A' was designed to have similar desirable qualities to the Feldkamp oligos using CANADA DNA sequence generating software (Feldkamp, et al., 2002; Feldkamp, et al., 2010) to simulate hybridization, melting and folding activity. Oligo-A/A' was used as a "universal" oligo sequence (see discussion following).

Antibodies were selected targeting commonly-probed T-cell markers CD4 and CD8, as well as activation-associated surface antigen CD43, which is expressed at distinct low and high levels, and lymphocyte homing molecule CD62L, which expresses at a range of levels as it is degraded upon cellular activation. Antibody clones were chosen based on previously validated activity for αCD4 (clone GK1.5), αCD8 (2.43.1), αCD43 (S7) and αCD62L (MEL-14) (activity confirmed by personal communication). As a panel, these four antibody targets allow for phenotypic delineation of several subsets of murine T-lymphocytes. Antibody-oligo conjugates are listed in Table 2.

TABLE 2

Oligonucleotide conjugates

| Ig:oligo conjugate | Clone | Oligos per Ig | Conjugate | DOL |
|---|---|---|---|---|
| αCD4:oligo-1 | GK1.5 | 2.1 | oligo-1':Dy490 | 4.7 |
| αCD8:oligo-2 | 2.43.1 | 2.4 | oligo-2':Dy549 | 6.4 |
| αCD43:oligo-3 | S7 | 3.1 | oligo-3':Dy649 | 8.1 |
| αCD62L:oligo-4 | MEL-14 | 2.6 | oligo-4':Dy405 | 10.4 |
| αCD4:oligo-A | GK1.5 | 4.6 | oligo-A':Dy490 | 7.6 |
| αCD8:oligo-A | 2.43.1 | 2.8 | oligo-A':Dy549 | 6.5 |

Oligo:fluorophores labeling constructs used for this study are also described in Table 2. DyLight fluorophores were chosen due to their suitability for 4-laser flow cytometry, relatively narrow excitation/emission spectra which reduces or eliminates the need for spectral compensation of multiplexed staining data, and availability in NHS-ester modified format for conjugation to oligo-dextran scaffolds (see below).

2. Oligonucleotide Conjugate Preparation

Antibody:oligonucleotides targeting constructs were prepared as shown in FIG. 1A. Briefly, succinimidyl-6-hydrazinonicotinamide acetone hydrazone (S-HyNic) was added to purified antibody, converting free amino groups on lysines near the antibody hinge region to HyNic moieties. Similarly, succinimidyl-4-formylbenzamide (S-4FB) was added to amino-modified oligo converts amino groups to 4FB moieties. When combined in the presence of aniline catalyst, the HyNic and 4-FB sites on modified biomolecules react to produce a stable, covalent hydrazone bond and forming the antibody:oligo conjugate. Following purification using a nickel column, this process resulted in >95% yield of antibody:oligo targeting constructs.

The preparation of oligo:fluorophore labeling constructs is shown in FIG. 1B. Amino-dextran bearing ~20 amino groups per dextran was first HyNic-modified using a limited amount of S-HyNic to result in 3-4 HyNic moieties per dextran. To the HyNic-amino-dextran was added a stoichiometrically limiting amount of 4-FB-oligo such that the number of oligos per dextran in the final product was limited to ≤1, an important factor necessary to restrict oligo hybridization at a 1:1 ratio of antibody:oligo targeting construct to oligo:fluor labeling construct. Multiple-oligo hybridization would result in more than one antibody per dextran conjugate, which could produce unwanted double-hybridization and aggregation of conjugates.

Following oligo-coupling to the dextran scaffold, free amino groups on the dextran remain available for reaction with NHS ester fluorophore (here, NHS-DyLight fluors were used). A molar excess of NHS-fluor was added to oligo-dextran, allowed to react and the final conjugate was characterized after desalting by dialysis. Characterization by A260 assay allowed calculation of fluorophore Degree Of Labeling (DOL) of the conjugate. Oligo:fluorophore labeling constructs having DOL from approximately 3-15 fluors per dextran were prepared, with a final conjugate yield of 15-20%.

Figure 1C:
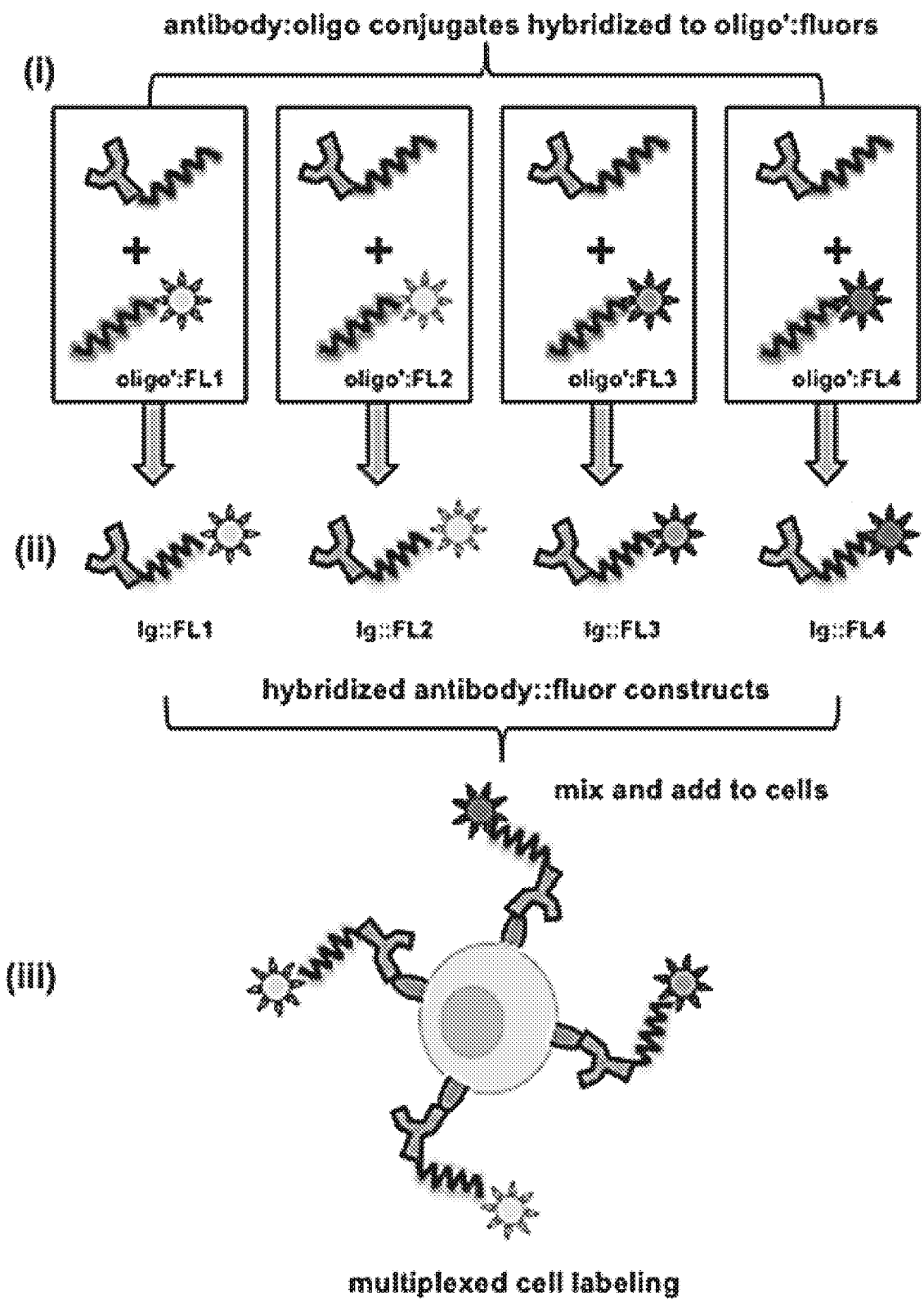

Oligo-conjugates were utilized for cellular antigen labeling as illustrated in FIG. 1C. First, antibody:oligo targeting constructs were hybridized to complementary oligo:fluorophore labeling constructs briefly in solution. The prepared antibody::fluorophore labeled targeting hybrid was then used to label cells in the manner of a conventionally prepared antibody-fluorophore conjugate. Hybridized labeling constructs can be used to label cells for a single antigen, or (as shown in the figure), combined into a labeling cocktail for multiplexed cell labeling.

3. Optimization of Hybridization and Cell Labeling Conditions

A model system including freshly prepared normal B6 murine splenocytes, commonly used control and validation T-cell marker antibody CD4, and DyLight 490 (Dy490) fluorophore was used to determine optimal assay conditions for labeling-construct hybridization and viable cell staining Antibodies and dextran-coupled fluorophores were oligo-modified as previously described. Cells were stained with antibody::fluorophore labeled targeting hybrids in a conventional manner (e.g., added to Fc receptor-blocked cells for 30 minutes at 4° C.), washed and analyzed by flow cytometry; CD4 staining was visualized for the gated lymphocyte population.

Figure 2A:
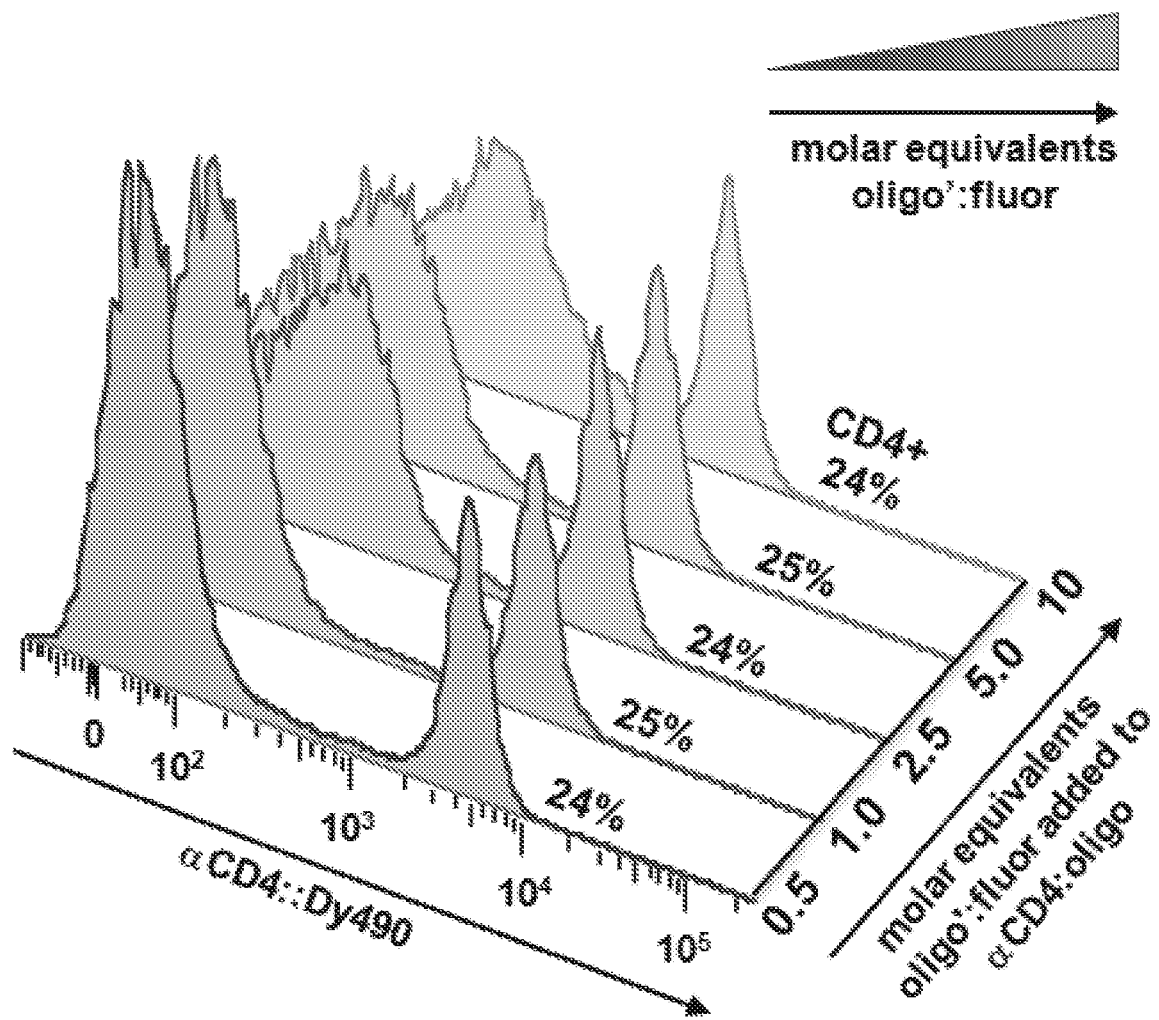
FIGS. 2A-2E Optimization of hybridization labeling conditions.

It was first investigated whether antibody:oligo targeting constructs could be hybridized to complementary oligo:fluorophore labeling constructs briefly in solution, and the resulting solution of labeled targeting hybrids then used to label cells. To this end, it was hypothesized that the ratio of oligo:fluorophore labeling construct added to antibody:oligo targeting construct would affect hybridization in solution, and subsequently alter cytometric staining distribution of labeled cells. In order to test this, a titration of increasing molar equivalents of oligo:fluorophore labeling construct was added to a fixed amount (6 pmol) of antibody:oligo targeting construct, from 0.5-10 molar equivalents (FIG. 2A). For antibody:oligo targeting construct having an MSR of ~2 oligos per Ig molecule, 0.5 molar equivalents oligo:fluor labeling construct represents the addition of 1 oligo:fluor labeling construct per Ig:oligo targeting construct. Results showed the population of CD4+ cells to be similar for all titrations; however, nonspecific background staining caused by addition of excess fluorophore increased with addition of >1 molar equivalent oligo:fluor labeling construct. A titration of 0.5 molar equivalents oligo:fluor labeling construct was used for subsequent CD4 staining, and for antibodies having varying degrees of oligo-modification, equivalents were added limiting hybridization to one oligo:fluor labeling construct per Ig:oligo targeting construct (i.e., if Ig:oligo MSR~4, then 0.25 equivalents oligo:fluor were added).

Figure 2B:
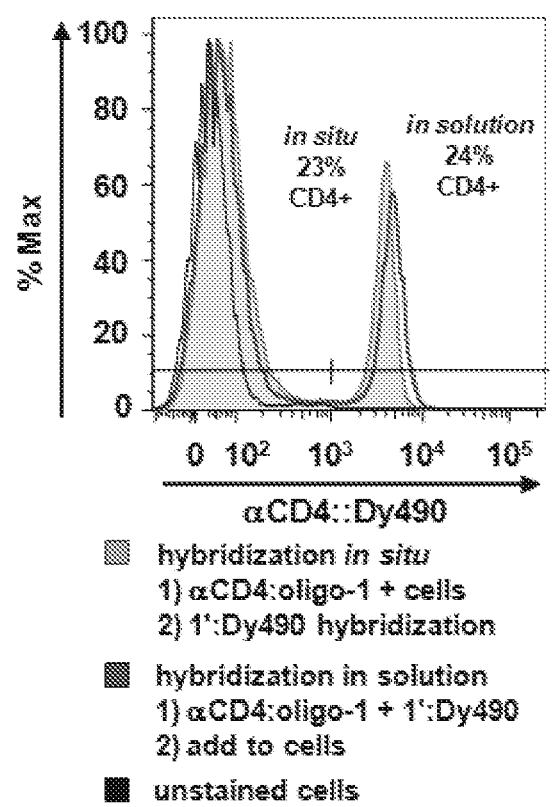

It also was investigated whether cells could be first labeled with antibody:oligo targeting construct, and then hybridized with oligo:fluor labeling construct in situ (FIG. 2B). Equal amounts of antibody and fluorophore oligo-conjugates were used for the two approaches, and cell staining and analysis conditions were identical. Results showed cell labeling via in situ hybridization to be effective, and very similar to labeling via hybridization in solution.

Figure 2C:
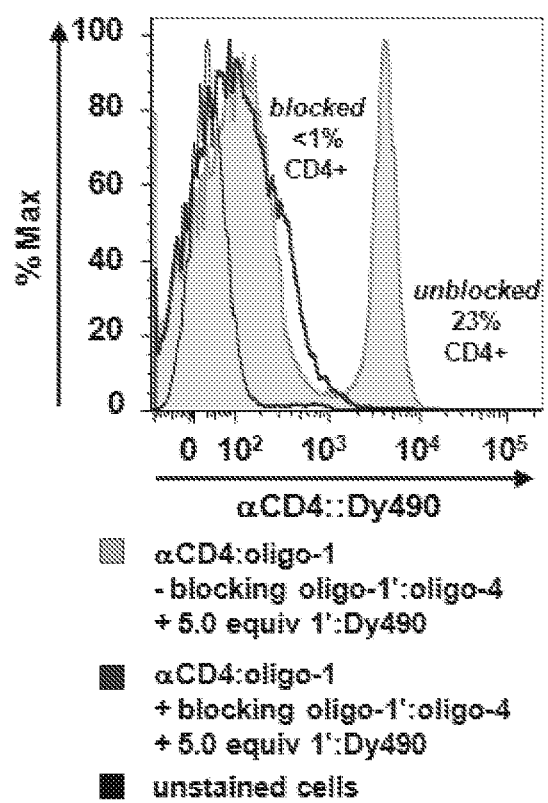

To confirm that CD4+ staining was indeed antigen-positive labeling and not an artifact of nonspecific oligo binding, hybridization of oligo:fluor labeling construct was blocked by hybridizing CD4 antibody:oligo targeting construct to a "blocking" oligo sequence complementary to the anti-CD4-oligo at the 5' end, with a sequence (oligo-4) unmatched to oligo:Dy490 at the 3' end. Following hybridization of the blocking oligo, oligo:Dy490 was applied. The blocked construct was applied to cells, and the cells were analyzed vs cells stained with unblocked, prehybridized xCD4::Dy490 labeled targeting hybrid (FIG. 2C). Results showed the blocking oligo (blue histogram) effectively prevented hybridization of the oligo:Dy490 labeling construct; no CD4+ population was evident, whereas cell labeling with the unblocked construct clearly resulted in a distinct CD4+ peak. The high background level in both samples was due to the experimental conditions, in which a 5-fold molar excess of oligo:Dy490 labeling construct was applied in order to fully test the ability of the blocking oligo at saturating conditions. The blocking oligo did not prevent nonspecific binding of the oligo:Dy490 labeling construct at this level of saturation, leading us to conclude that it is the dextran:fluor that is responsible for the nonspecific signal. However, this issue can typically be avoided by hybridizing at the optimized titration of 0.5 molar equivalents.

Figure 2D:
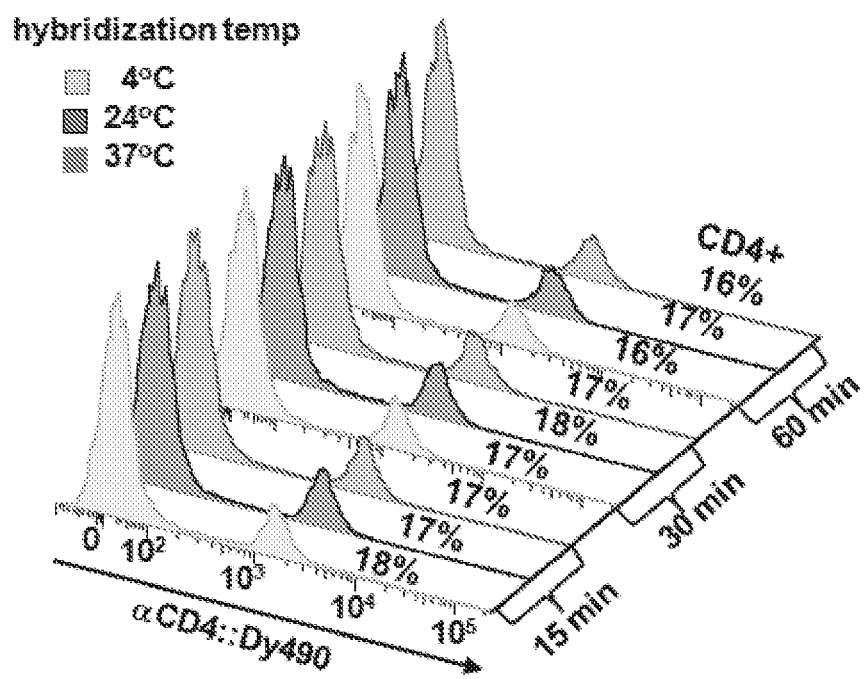

Hybridization has been well-described to be both time and temperature-dependent. A range of hybridization times from 15-60 minutes with incubation at 4° C., room temperature (24° C.), or 37° C. (FIG. 2D) were tested. Results showed a clear CD4+ signal at all time and temperature conditions tested, with negligible variance. The sequences selected for this study were designed to have high melting temperatures (Tm) and specific and stable hybridization activity, as previously reported by Feldkamp et al.

Figure 2E:
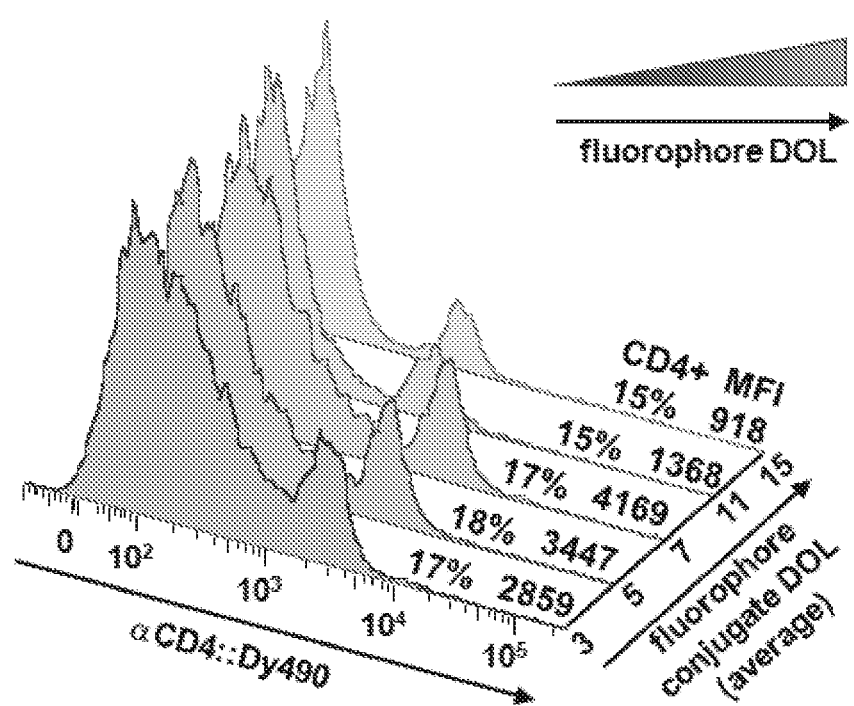

A further optimization test was designed to determine whether the number of fluorophores per dextran scaffold (Degree Of Labeling, DOL) affected signaling of labeled cells (FIG. 2E). Oligo-dextran-Dy490 conjugates having approximately 3-15 Dy490 per dextran were prepared. These conjugates were hybridized to anti-CD4:oligo targeting construct as previously described. Results showed optimal signaling distribution at DOL~7, with a decrease in positive-peak resolution at DOL<7 and a marked decrease in positive-peak median fluorescence intensity (GMFI) at DOL>7, most likely due to fluorescence self-quenching occurring as a result of spatial proximity of fluorophores added in excess to the dextran scaffold. Testing of additional fluorophores indicated that for dimmer fluors (e.g., Dy405), a higher degree of labeling is optimal (DOL~10; data not shown).

In summary, the hybridization-labeling assay is relatively robust. Molar equivalents of oligo:fluor labeling construct are preferably limited to ≤1× relative to the amount of antibody:oligo targeting construct. Oligo-conjugates can be hybridized either in solution or in situ for specific and effective labeling of cells. With these particular oligo sequences, a wide range of time and temperature conditions can be employed without significant variation in construct activity. Target DOL should be approximately 7 fluors per dextran, but a range of DOL's provide adequate labeling of antigen-positive cell populations.

4. Multiplexed Antigen Labeling

Figure 3A:
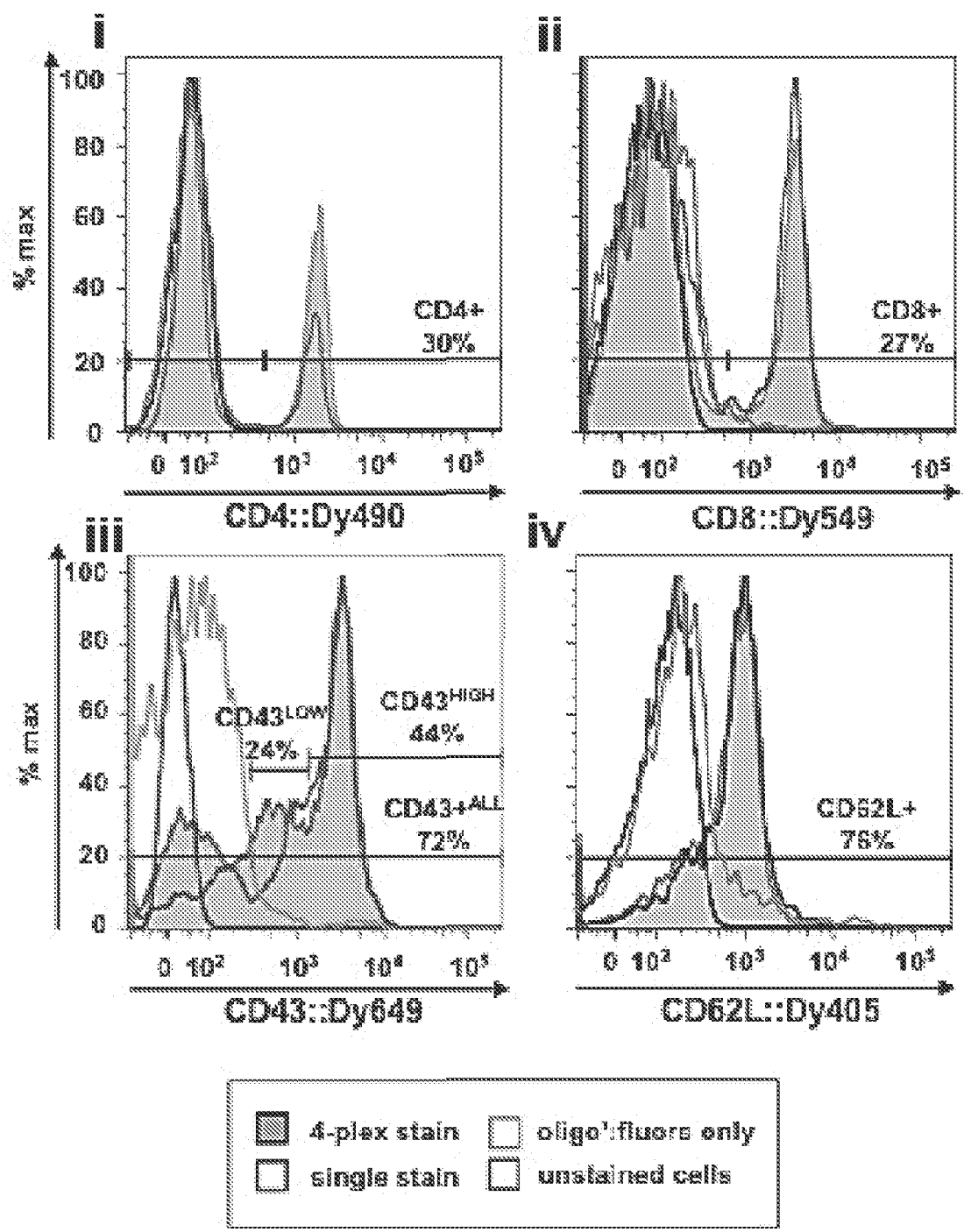
FIGS. 3A-3B (FIG. 3A) Antigen detection by antibody::fluorophore labeled targeting hybrids. Labeled targeting hybrids (i) xCD4::Dy490, (ii) xCD8::Dy549, (iii) xCD43::Dy649, and (iv) xCD62L::Dy405 were prehybridized, mixed, and used to label cells (tinted histograms). Single-construct stains (untinted histograms), oligo:fluorophore-only stains (gray histograms), and unstained cells (black histograms) were also analyzed as controls. Percentages shown are for the 4-plex stained cell sample. Results show effective antigen staining, comparable in single-stained samples to multiplexed stained cells. Antigen-positive population values were within expected ranges.

Using optimized assay conditions, four labeled targeting constructs were then prepared and used to label cells for a single antigen, or combined into a multiplexed labeling cocktail to label a single cell sample for four antigens at once (FIG. 3A). For these tests, a panel of oligo-conjugated antibodies against T-cell markers CD4 and CD8, activation-associated antigen CD43, and lymphocyte homing molecule CD62L was used. Each antibody:oligo targeting construct was hybridized to complementary oligo:fluorophore labeling construct in solution, using the Dylight fluors Dy490, Dy549, Dy649, or Dy405. The antibody::fluor labeled targeting hybrids were then used to label normal B6 murine splenocytes and the stained cells were analyzed by flow cytometry. All antibody-labeled cell samples displayed clearly evident antigen-positive populations. Positive-labeled cell populations were within expected ranges [10-14]. Multiplexed staining was comparable to single-antigen staining; cells stained with fluorophore-only exhibited varying degrees of nonspecific staining when compared to unstained controls, from negligible (Dy490) to moderately high (Dy649).

Figure 3B:
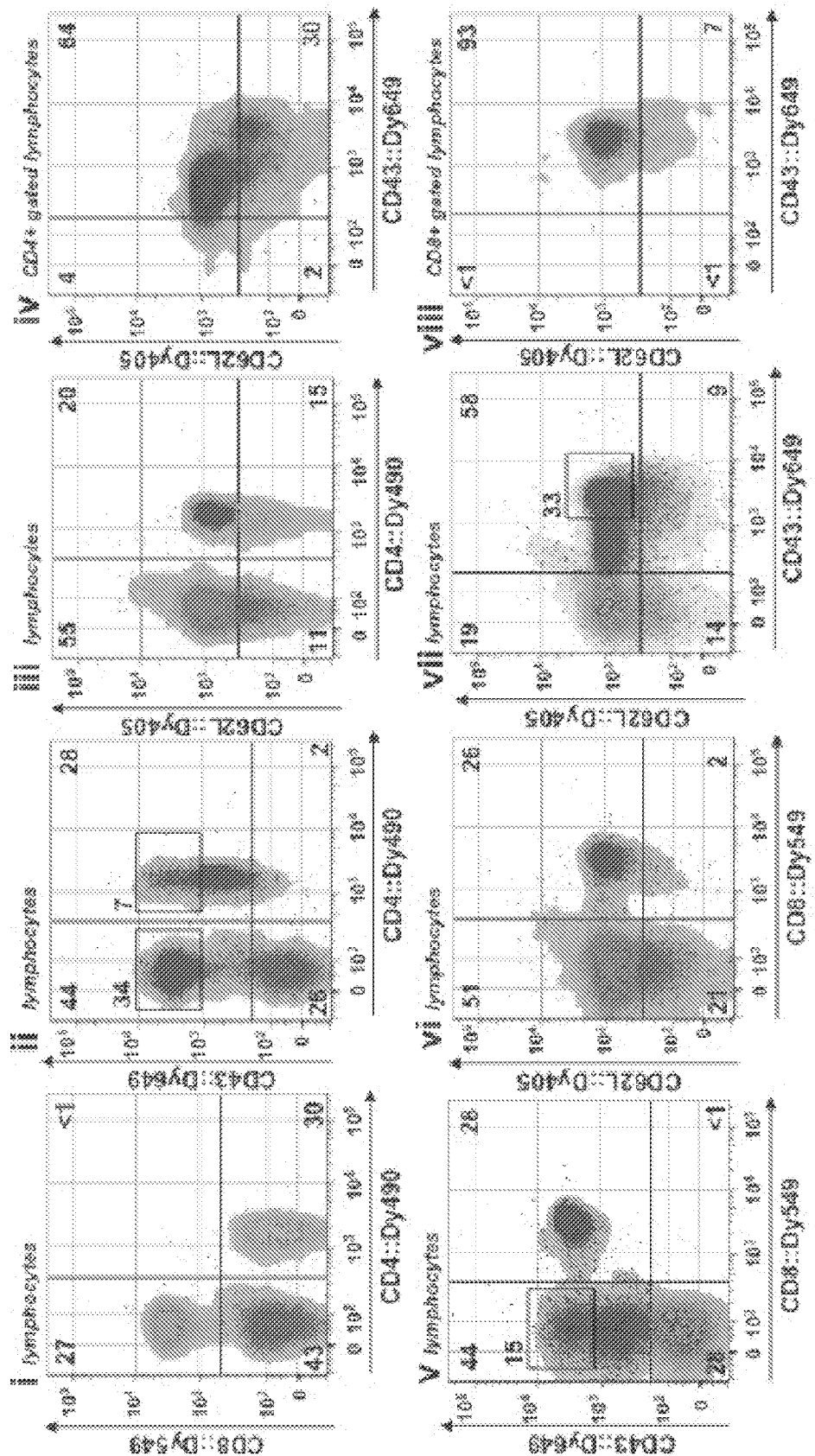

Multiplexed staining results displayed as 2-channel, 2D dot plots allowed for phenotypic delineation of the cell population (FIG. 3B). Lymphocytes are displayed as CD4 vs CD8 (panel i), CD43 (panel ii), CD62L (panel iii), or gated on the CD4+ population and displayed on a CD43 vs CD62L 2D plot (panel iv). In each panel, cellular subsets are distinctly evident; for example, CD4+ and CD8+ T-lymphocytes are clearly defined (30% and 27% respectively); populations of CD43$^{HIGH}$ lymphocytes are visible for CD4− and CD4+ cells (34%, 7%); and two distinct CD62L+ groups are evident, either CD4− (55%) or CD4+ (20%). Lymphocytes displayed as CD8 vs CD43 (panel v) or CD62L (panel vi) show clear double-stained populations in both plots. CD43 vs CD62L (panel vii) also shows double-stained cells (58%), with CD43$^{HIGH}$ CD62L+ cells representing 33% of total lymphocytes. Finally, gated CD8+ lymphocytes are almost entirely (93%) triple-positive for CD8+ CD43+ CD62L+. These results provide substantial evidence that the oligo-conjugates can be used for specific and sensitive multiparameter cellular phenotyping.

5. Interchangeable Fluorophore Hybridization Using the Universal Oligo Sequence

Figure 4A:
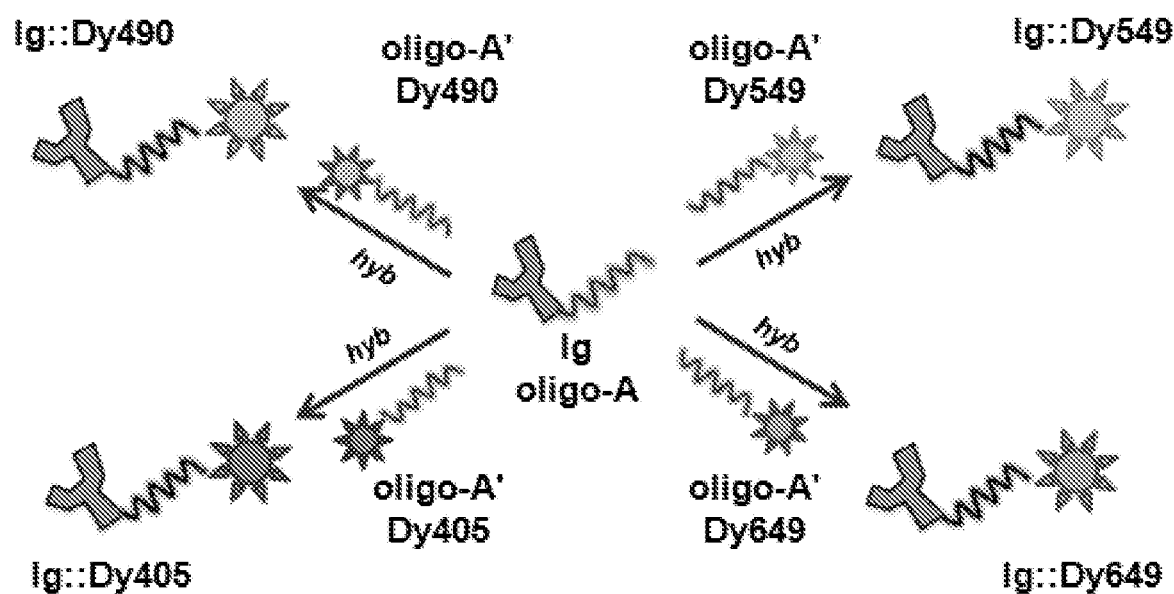
FIGS. 4A-4C. Interchangeable fluorophore hybridization using the universal oligo sequence pair.
Figure 4B:
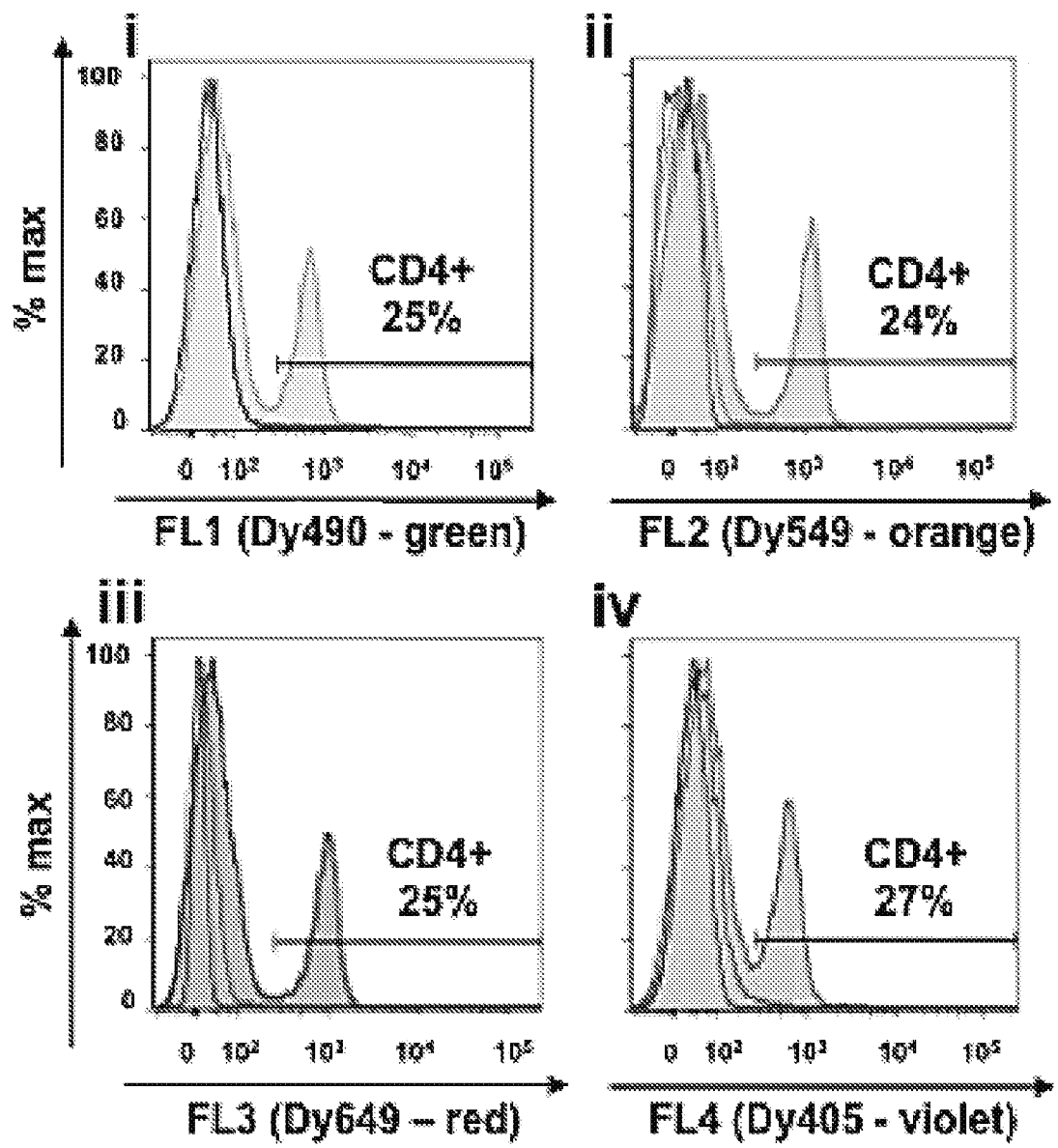

For experiments discussed thus far, the oligo sequences 1/1'-4/4' were used to hybridize antibodies with fluorophores. However, by utilizing a single oligo pair (A/A') conjugated to either antibodies (e.g., an Ig:oligo-A targeting construct) or dextran:fluors (e.g., an oligo-A':fluor labeling construct), any antibody may easily be hybridized to any fluorophore. This "mix and match" approach is illustrated in FIG. 4A. Cytometric data obtained using CD4 and CD8 antibodies hybridized to four fluorophores validated this approach, as antigen-positive staining was very similar across fluorescent channels for both antibodies (FIG. 4B).

Figure 4C:
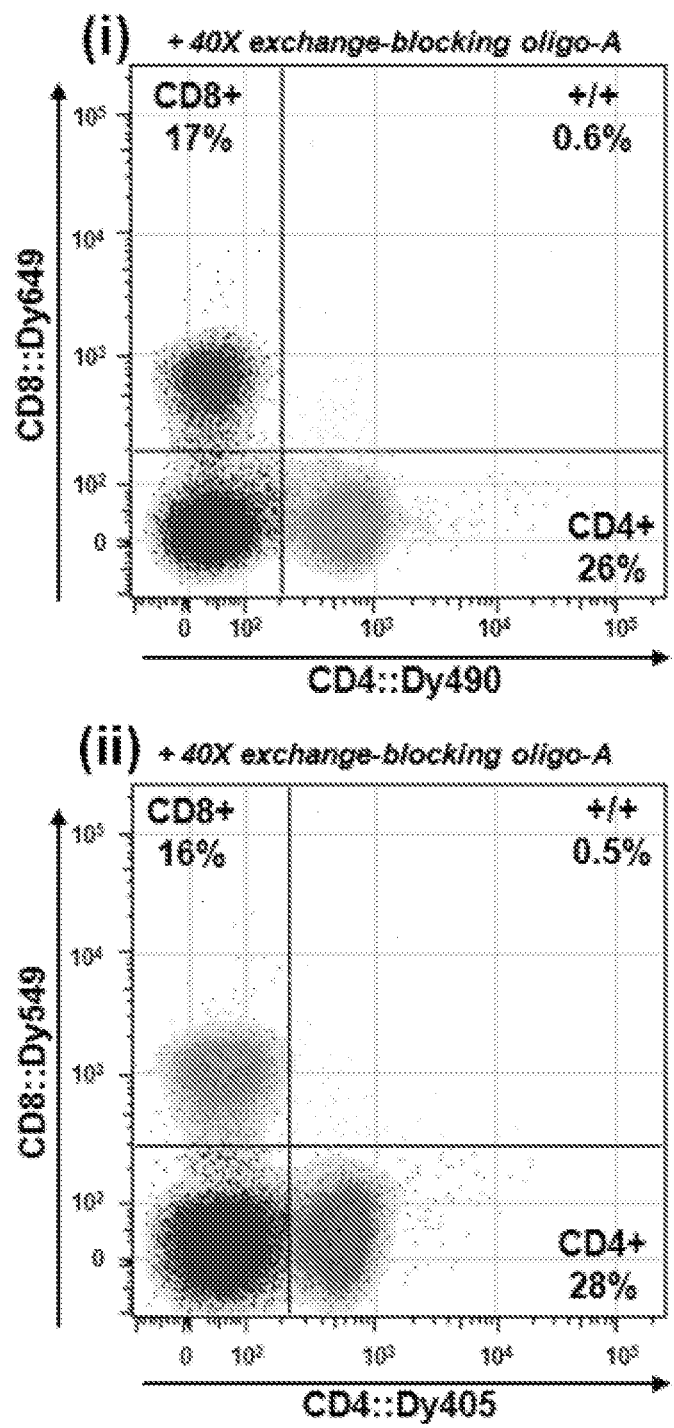

However, utilizing one oligo pair for all constructs potentially posed a problem for multiplexing, i.e when constructs are combined, free oligo:fluor labeling constructs could hybridize to any antibody:oligo targeting construct, or oligo:fluor labeling constructs could dehybridize and exchange. To test this, CD4/CD8 double staining was performed using no blocking methods to evaluate unwanted crosstalk. Indeed, crosstalk was observed at 1-5%, with the highest levels measured after the double-staining solution was left overnight at room temperature. The inventors hypothesized that a saturating amount of unmodified oligo would successfully outcompete free oligo:fluor labeling construct for binding sites, thus preventing crosstalk. To test this, the inventors added unmodified oligo-A at increasing saturations to pre-hybridized antibody::fluorophore labeled targeting hybrid from 0-100 molar equivalents blocking oligo-A. The 'blocked' constructs were then mixed and used to stain cells. Results indicated that crosstalk, which would be evident in the double-positive quadrants, was reduced to ~0.5% by the addition of 40× equivalents blocking oligo (FIG. 4C). CD4+ and CD8+ populations are clearly seen in both plots, either CD4::Dy490 (FIG. 4C(i), lower right cluster) vs CD8::Dy649 (FIG. 4C(i), upper left cluster), or CD4::Dy405 (FIG. 4C(ii), lower right cluster) vs CD8::Dy549 (FIG. 4C(ii), upper left cluster).

6. Quantitation Using Oligonucleotide-Coated Particles

Two methods of preparation of quantitative fluorophore-hybridized oligospheres are illustrated in FIG. 5A-5B: Method I, "parallel labeling" and Method II, "combined labeling".

In Method I (FIG. 5A, "parallel labeling"), linker-modified paramagnetic microspheres are conjugated with a saturating amount of linker-reactive oligonucleotide, resulting in oligo-conjugated microspheres. The oligospheres are then hybridized to complementary oligo:polyfluor labeling constructs at several levels of surface saturation, and the labeled fluorophore-hybridized oligospheres are added to cells previously stained with the same labeling probe(s) for quantitation of Antibody Binding per Cell (ABC). Thus, oligospheres and cells are labeled separately, hence the term "parallel labeling".

In Method II (FIG. 5B, "combined labeling"), linker-modified paramagnetic microspheres are conjugated with increasing titrations of linker-reactive oligonucleotide, resulting in oligo-conjugated microspheres of increasing oligo surface saturation. The oligo-surfaced microspheres are then combined with cells that have been labeled with antibody-oligo targeting construct that bears the same oligo sequence as the oligospheres. To the cell-sphere mixture is then added an amount of labeling construct sufficient to label both cells and oligospheres. Thus, oligospheres and cells are labeled together, hence the term "combined labeling". Following combined labeling, the cell-sphere mixture is analyzed for quantitation of ABC.

After preparation of fluorophore-labeled oligospheres using either Method, the number of Labeling construct Per oligosphere Event (LPE) for each saturation level must be determined by fluorimetric analysis (FIG. 5C). LPE is a critical value for determination of Antibody Binding per Cell (ABC). LPE is determined by measuring fluorescence of a populations of oligospheres in wells of a microplate vs a standard curve of labeling construct in solution in the same microplate. Then, the precise number of microspheres per sample is counted using a handheld particle analyzer. These two measurements allow determination of LPE by [(mol label per sample×(6×1023) molecules per mol)/number of oligospheres per sample]. The fluorometrically-determined LPE values of the quantitative oligospheres are recorded and later used to determine ABC following cytometric analysis (example cytometric data shown in FIG. 5D).

The ABC quantitation method was testing using four antibody-fluorophore pairs (CD4/Dy490; CD8/Dy549; CD43/Dy649; and CD62L/Dy405), with matching fluorophore-hybridized oligospheres.

For quantitation by cytometric analysis, the quantitative microspheres were added to an equal volume of viable murine splenocytes multi-stained with a panel of the same oligo:polyfluor labeling constructs (Method I, parallel labeling). The heterogeneous samples of cells and microspheres were cytometrically analyzed (FIGS. 6A-6D). Cytometric analysis of labeled cells and oligospheres results in cytometric fluorescence data for antibody-stained cells along with an internal quantitative standard curve provided by the oligospheres. The standard curve generated by the oligospheres is used to calculate quantitative ABC from arbitrary units of cytometric Geometric Mean Fluorescence Intensity (GMFI).

To create quantitative plots for each antibody/fluorophore pair, log GMFI values for each microsphere peak in each channel (see FIGS. 6A-6D) were calculated using FlowJo analysis software. As shown in graphs (FIGS. 7A-7D), log GMFIs were plotted against log LPE for each label (Dy490, Dy549, Dy649, Dy405), which had been determined by fluorimetric assay as described above. An exponential trendline was fit to microsphere data as shown.

Figure 8:
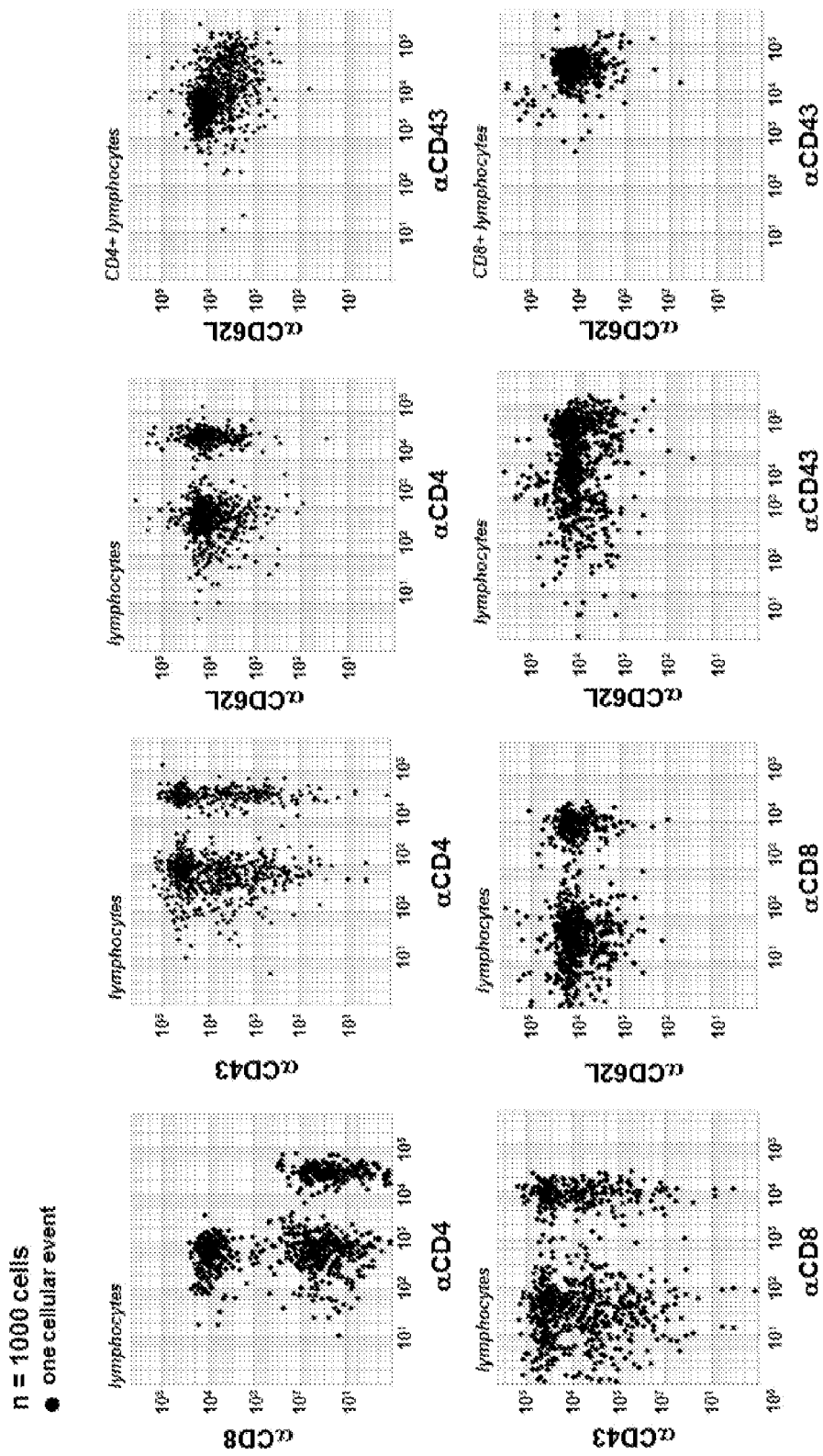
FIG. 8. Single-cell ABC. Determination of single-cell ABC for 1,000 lymphocytes was conducted as shown in FIG. 7 and results are presented in 2-channel dot plots showing distribution of cellular populations. As expected, quantitative ABC cellular distribution is similar to qualitative 2D plots shown in FIG. 3B, yet quantitative data yields improved information regarding the antigenicity of cells.

Determination of ABC in the system is based on the assumption that one oligo-polyfluor labeling construct is hybridized per antibody when a limiting amount of labeling construct is applied during antibody::fluorophore oligo-construct hybridization. In other words, a 1:1 ratio of label to antibody is assumed; therefore, the number of oligo-polyfluor Label Per Event (LPE) is equal to number of Antibodies Bound per Cell (ABC). That is, [LPE=ABC]; and so ABC for cellular events can thus be calculated using the trendline equations shown in FIG. 7. Mean ABC can be calculated using the GMFI of a population of cellular events (as noted in FIG. 7), or single-cell ABC can be calculated using fluorescence intensity signal of any single cell recorded by the cytometer (FIG. 8).

Method II (combined labeling) was also conducted using CD4 antibody:oligo targeting construct with a complementary oligo:Alexa Fluor 488 labeling construct. (FIG. 9). Oligospheres at increasing surface oligo saturation (0-100%) were combined with murine splenocytes bearing CD4 antibody:oligo targeting construct. Labeling construct was then applied at 2-fold excess to targeting construct (mol oligo/oligo) and the combined cell-oligosphere labeled sample was cytometrically analyzed. Oligospheres and lymphocytes were scatter gated (FIG. 9A) and CD4+ lymphocytes were gated using FL1 (Alexa 488) vs SSC (FIG. 9B). The gated oligospheres and CD4+ lymphocytes were displayed on a histogram showing fluorescence signal distribution of each population. Because quantitation of ABC$_{CD4}$ using these data would proceed exactly according to the methodology described above, the inventors did not recapitulate quantitation using these data.

ABC quantitation as described above was validated by head-to-head quantitation of ABC$_{CD4}$ with commercially available PE-conjugated CD4 antibody and PE quantitation microspheres (BD QuantiBrite PE, FIG. 10A). A specific monoclonal antibody was chosen for quantitation using both systems (clone GK1.5). Commercial quantitation was performed according to manufacturer protocol resulting in the graph and ABC trendline equation shown in FIG. 10B. The commercial quantitation method was very similar to that performed using the oligosphere method described above, i.e., analyzing fluorescent microspheres and stained cells, plotting log fluorescence units vs known LPE, and converting fluorescence units to ABC based on trendline using an assumption of 1:1 label:protein ratio. Results show oligosphere-based quantitation of ABC$_{CD4}$ was very similar to ABC$_{CD4}$ obtained using commercial microspheres (28.8× 103 vs 29.7×103 per cell).

Flowchart algorithms (FIGS. 11A-11B) depict a workflow for planned computer analysis software that will be used to simplify and automate the ABC quantitation methods described above. The software will utilize instrument-generated cytometer raw data (e.g., .fcs listmode files) to streamline the various ABC quantitation procedures described above, using two Algorithms.

Algorithm I (FIG. 11A) accomplishes gating of oligospheres, calculation of gate GMFIs, and plots ABC quantitation standard curve with fluorescence-to-ABC conversion trendline. Algorithm II (FIG. 11B) then analyzes user-defined cellular events using the ABC quantitation curve(s) generated by Algorithm I to convert arbitrary cellular fluorescence data to quantitative ABC data. ABC data for large cellular populations (thousands to millions of single events) can then be statistically analyzed and/or displayed graphically by the user. In early versions the software will likely be spreadsheet-based, followed by increasingly advanced, user-friendly platforms as software development progresses.

7. Spectral Compensation Using Fluorophore-Hybridized Oligospheres

Spectral compensation, a common practice in multicolor cytometric analysis, refers to the unmixing of overlapping fluorescent emission spectra in effort to separate each color during analysis, thus enabling accurate signal analysis in each antibody-specific fluorescent channel.

To validate oligospheres for use in spectral compensation (FIGS. 12A-12C), oligospheres were hybridized to fluorescent oligo labeling constructs having similar excitation and emission spectra (FL1, Alexa Fluor 488; and FL2, Alexa Fluor 532). Oligospheres were prepared as described and fluorescent oligo labeling constructs were commercially obtained (Integrated DNA Technologies). Single-fluorophore-hybridized oligospheres were analyzed separately as compensation controls, and then mixed ~1:1 into a two-colored sample to which compensation controls were applied for spectral unmixing. Nonfluorescent microspheres were included in the analysis as a negative control. A cytometer with somewhat limited spectral capabilities (BD LSRII, 488 nm blue laser with FL1 & FL2 detectors on shared laser line) was used for the analysis in order to provide maximum necessity for spectral compensation.

Compensation was accomplished using typical methodology and analysis software (TreeStar's FlowJo Compensation Wizard). Single-color oligosphere controls were recognized by software and auto-gated appropriately (FIG. 12A; shown are singlet gates, positive gates, negative gates). An algebraic compensation matrix was calculated by the software (not shown), and the matrix algebra was then applied by the software to correct the two-color sample. The uncompensated two-color sample (FIG. 12B) appeared to contain two populations both positive for FL1 and FL2, which was not the case; each sample was labeled with only one type of fluorophore, either FL1 or FL2. The compensated sample (FIG. 12C) correctly depicts the distinct single-color FL1+ and FL2+ populations, as well as the negative population. The low-level signaling (0-$10^3$) of the negative population is caused by autofluorescence of the microspheres.

8. Fluorophore-Hybridized Oligospheres for Cytometer Alignment and Calibration

Figure 13A:
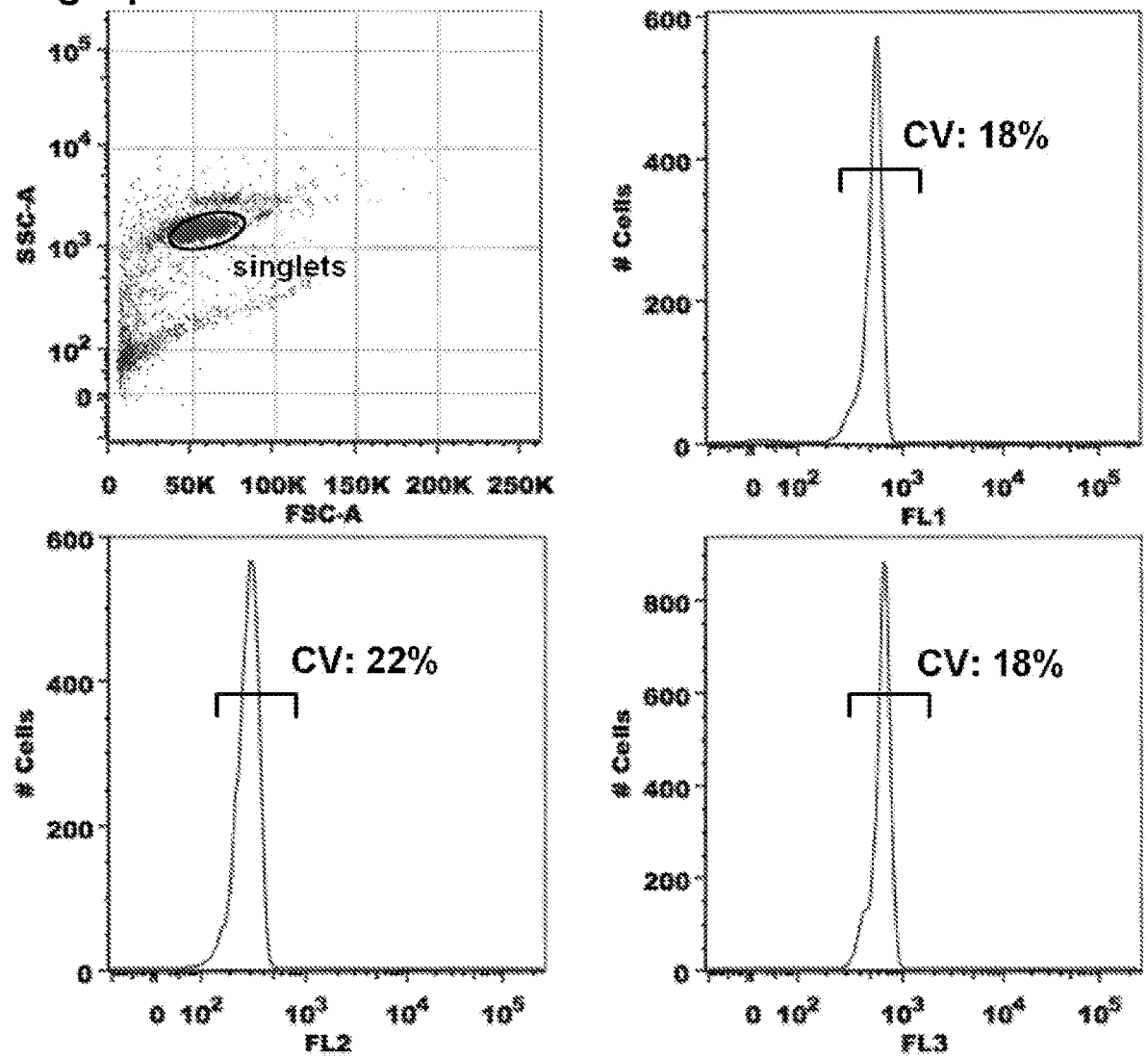
FIGS. 13A-13B. Cytometer Alignment. Fluorophore-hybridized oligospheres of a single color and intensity (FIG. 13A) were compared to commercial fluorescent microspheres (FIG. 13B) in terms of CV (%) to evaluate whether oligospheres may be used for instrument alignment. CVs were similar for oligospheres and commercialized microspheres. The inventors plan to reduce CVs for oligospheres in the future by utilizing alternative amino-functionalized microspheres as a starting point, that may enable CV reduction of resulting fluorescent signal.
Figure 13B:
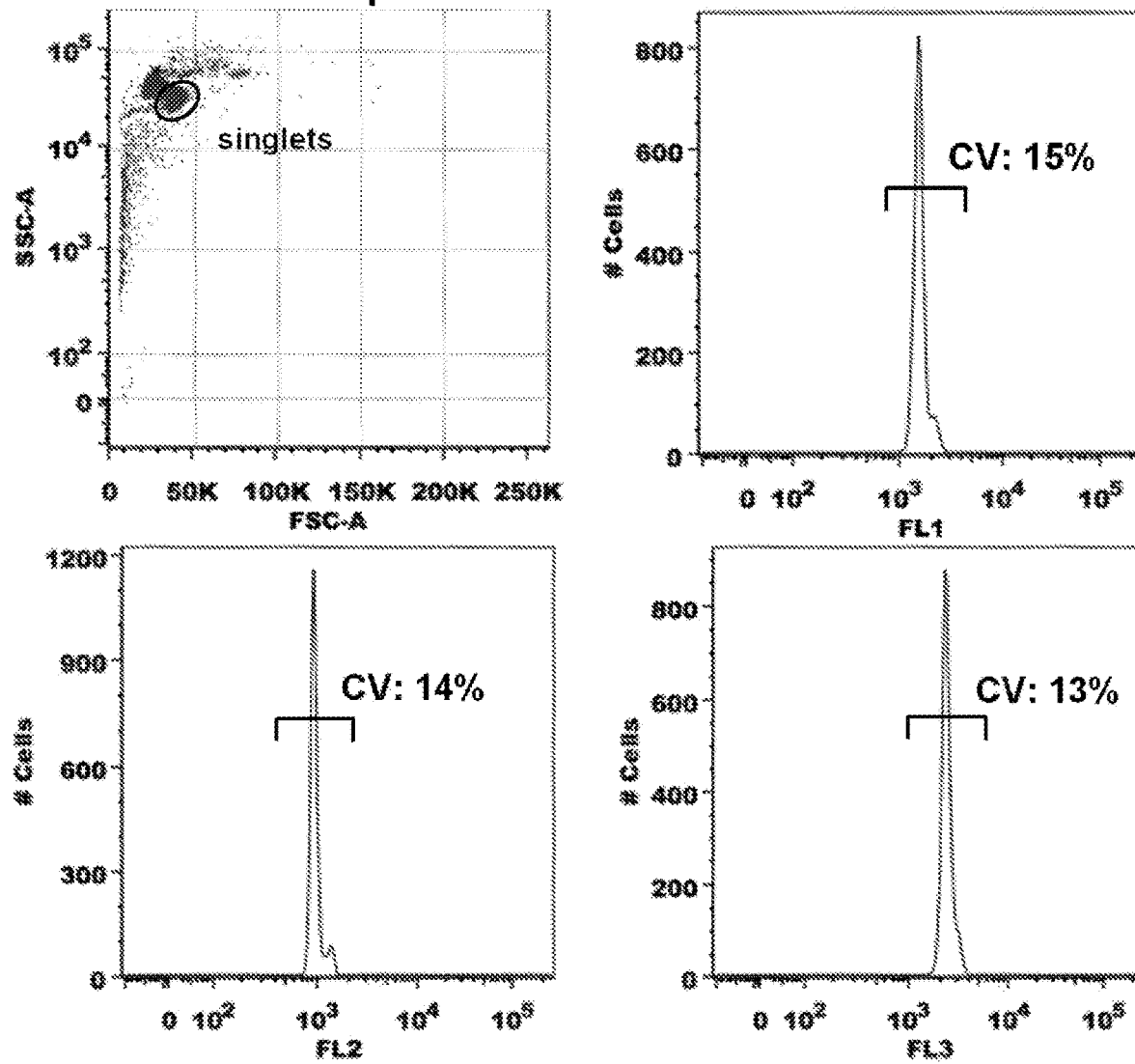

A common application for fluorescent microspheres is the routine alignment and calibration of cytometer optical components. Fluorophore-hybridized oligospheres were evaluated for alignment and calibration purposes as compared to commercially available fluorescent microspheres (FIGS. 13-14).

To evaluate whether oligospheres could potentially be used for instrument alignment (FIG. 13), fluorophore-hybridized oligospheres were prepared in a method resulting in single-fluorophore microspheres in a variety of spectral 'colors' (similar in concept to commercially prepared alignment microspheres, e.g., Spherotech Fluorescence Alignment Particles). Oligospheres were hybridized with a saturating amount of complementary oligo:fluorophore labeling constructs in distinct spectra (Alexa Fluor 488, 532, and 647). A single type of fluorophore was hybridized to each sample of oligospheres.

The oligospheres (FIG. 13A) and commercial microspheres (FIG. 13B) were then analyzed on a conventional cytometer to determine size distribution (scatter plots) and fluorescent signal (single-peak histograms). Post-acquisition, singlets were gated and CVs were determined for fluorescent signal histograms using analysis software. CVs were compared for oligospheres vs commercial microspheres in three fluorescent channels (FL1, FL2, FL3).

Lower CVs are desirable for properly evaluating instrument alignment. Commercial microspheres had slightly lower CVs. The inventors hypothesize that the higher CVs seen with oligospheres is a result of greater size and granularity (FSC and SSC) distribution of the particular microspheres used for this test (see scatter plots FIG. 13A vs 13B). A wide variety of microspheres can be used to prepare oligospheres; by adjusting the type of microsphere used, the inventors hope to reduce scatter variation, thereby reducing oligosphere CVs to a level competitive with (or better than) current state-of-the-art alignment aids.

To evaluate whether oligospheres could potentially be used for instrument calibration (FIG. 14), fluorophore-hybridized oligospheres were prepared in a method resulting in microspheres in a variety of increasing intensities (similar in concept to commercially prepared alignment microspheres, e.g., Spherotech Calibration Particles). Oligospheres were hybridized with titrated amounts of complementary oligo:fluorophore labeling construct (Alexa Fluor 488). A specific titration was hybridized to each sample of oligospheres and then the oligospheres were mixed into a single batch for analysis (FIG. 14A). The oligospheres were compared to commercially prepared microspheres (FIG. 14B). Results showed distinct peak formation with a dynamic range of signaling comparable to commercial microspheres. For future development, additional peaks can be included in the oligosphere mixture, (e.g., 6-8 peaks) and additional fluorophores can be used to test signaling across multiple fluorescent channels (e.g., FL2, FL3, etc).

9. Discussion

Microsphere-based methods for flow cytometry enable both instrument Quality Control (QC) via alignment and calibration, and cellular analysis via Quantitative Flow Cytometry (QFC).

The novel oligosphere-based method enables cost-effective, spectrally-matched QC using oligospheres and labeling probes. The inventors envision QC reagents will be provided with multiplexed antibody labeling kits, or as standalone QC products, either of which the inventors hope will encourage and improve routine QC across academic, clinical, and industrial research laboratories.

Variation in the number of antigens per cell can indicate cellular phenotype, differentiation, and activation state, which makes microsphere-enabled quantitative flow cytometry useful as a research tool and as a clinical diagnostic test (Hultin, et al., 1998; Lin, et al., 1998; Schlenke, et al., 1998). There are a variety of commercial calibrants presently available to aid in QFC, yet there remain significant challenges. (as reviewed in Gratama, et al., 1998; Maher, et al., 2005 and discussed further below).

Figure 12A:
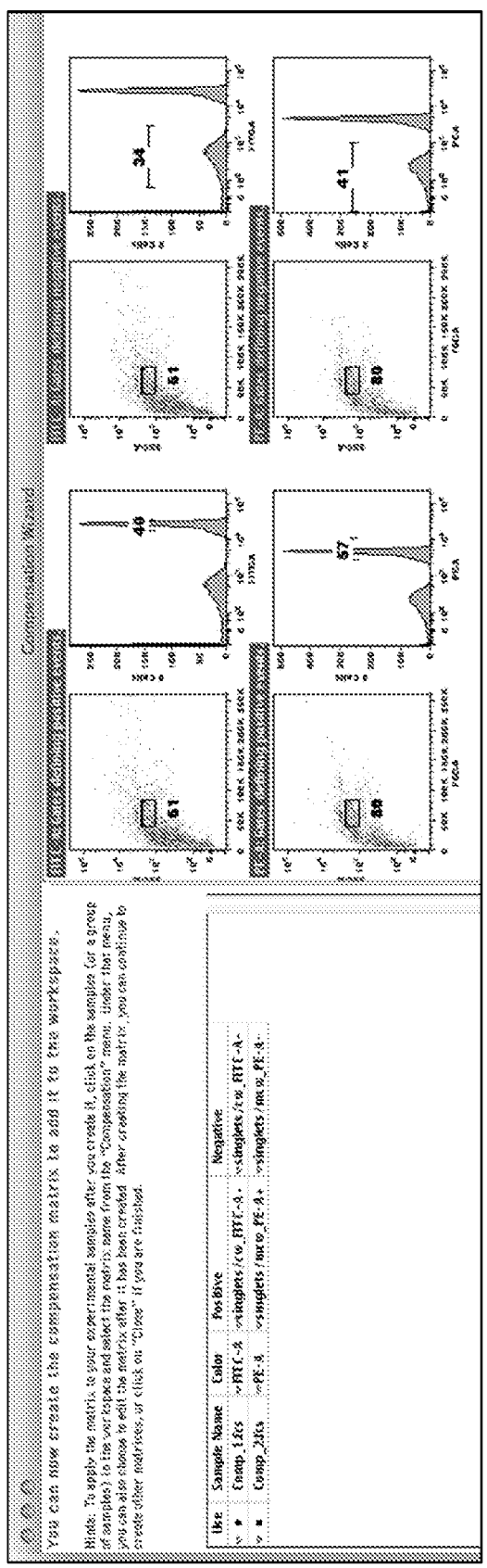

In addition to improved QC and QFC, the system offers more chromatic flexibility for day-to-day cytometry applications. The chromatically interchangeable "Mix and Match" hybridization strategy (FIGS. 4A-4C) offers a significant improvement over existing methods, and the fluorophore-hybridized oligospheres enable fast and accurate spectral compensation (FIGS. 12A-12C).

The "Mix and Match" strategy enables antibodies to quickly (minutes) be labeled with any fluorophore desired, a functionality that is extremely limited in today's laboratories which often rely entirely on prelabeled fluorescent antibodies. In contrast to existing methods, the inventors have shown that the system can be multiplexed using at least four targets, with the potential limiting factors being imposed only by the fluorophore-resolving capabilities of the cytometer being used (a limitation which similarly constrains conventional multiplexing).

Figure 11A:
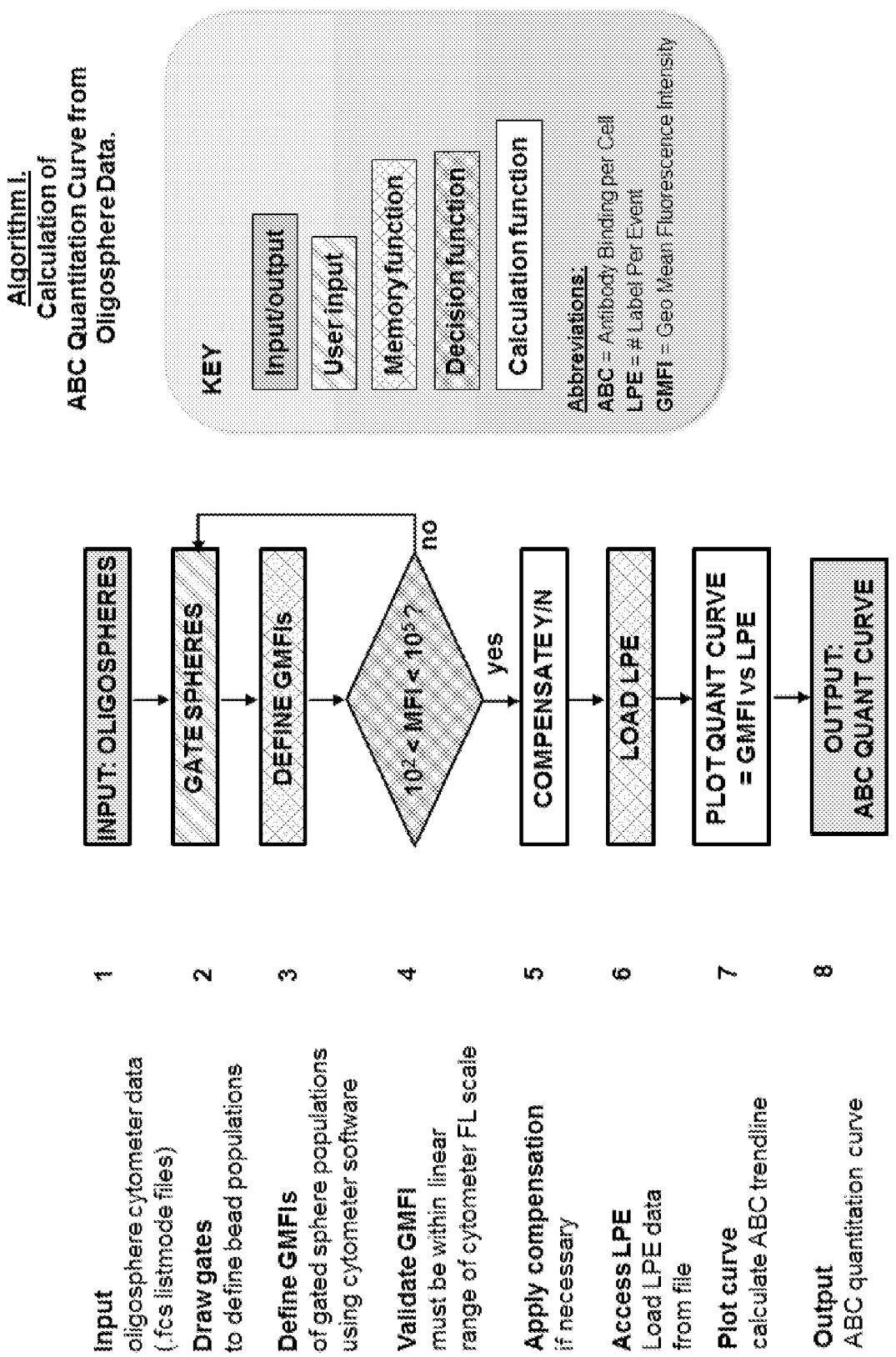
FIGS. 11A-11B. Flowcharts for Software Algorithms.
Figure 11B:
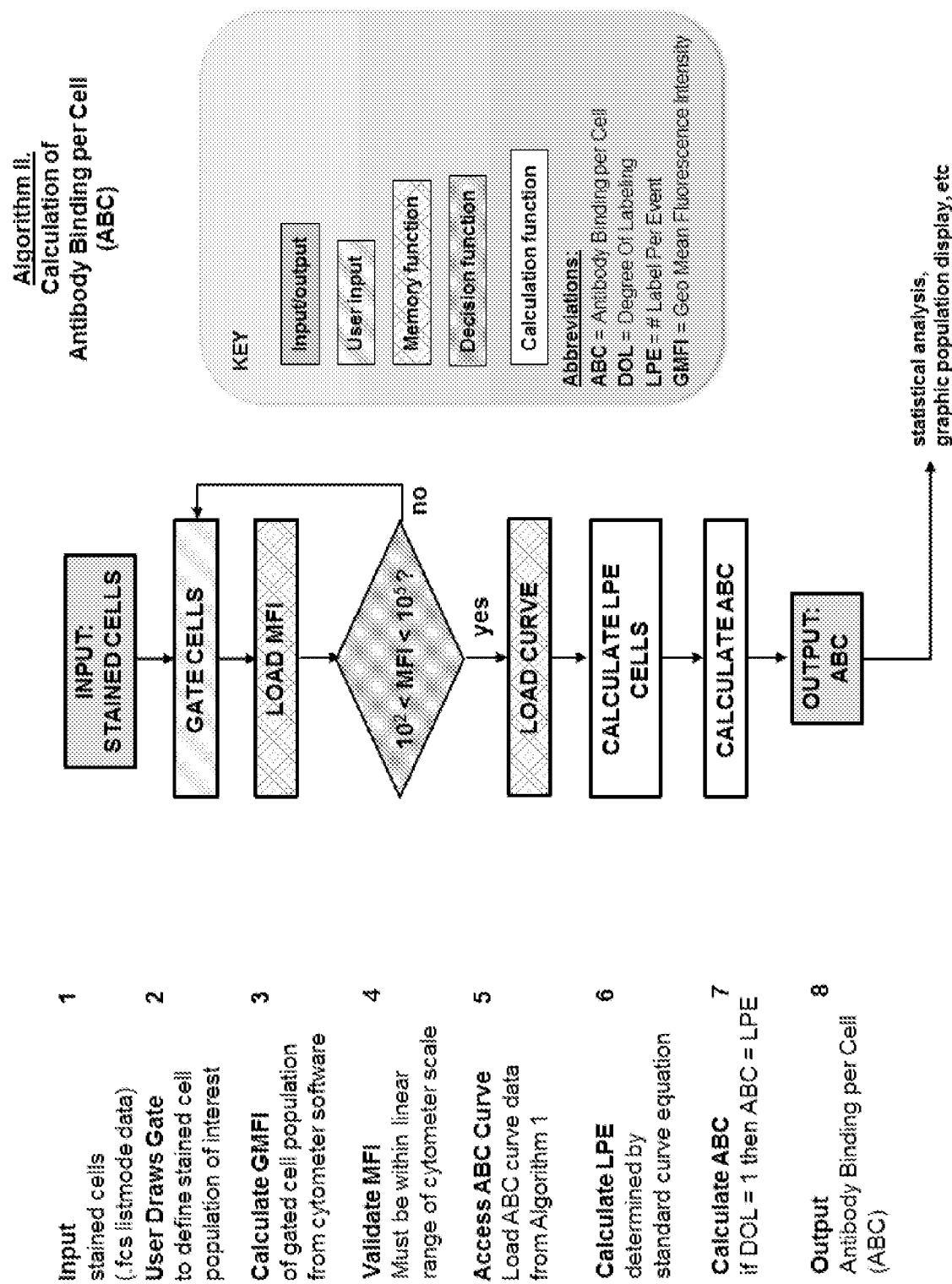

The inventors envision software to be designed for automated, rapid QC, QFC, compensation, and cellular analysis using the system. Software will be designed to incorporate techniques and on-screen tools familiar to those of ordinary skill in the art. An example of an algorithm for QFC is shown in FIGS. 11A-11B, and other algorithms are envisioned to be similarly designed. Software may be designed to be used with on-board acquisition software (e.g., BD FACSDiva), post-data analysis software (e.g., TreeStar FlowJo), or for in-depth statistical analysis of quantitative data, be spreadsheet-based.

In summary, the inventors envision the oligonucleotide-based system to be an all-in-one solution to many of the challenges presented by current flow cytometry methodologies, from day-to-day instrument maintenance to advanced, quantitative cellular analysis.

10. Methods a. Antibodies

Purified monoclonal antibodies for oligo-conjugation against murine CD4 (clone GK1.5) or CD8 (clone 2.43.1) were obtained from the Frank W. Fitch Monoclonal Antibody Bank at University of Chicago (Chicago, Ill.). Monoclonal murine anti-CD43 (clone S7) was a gift from Dr. John Kemp at University of Iowa School of Medicine (Iowa City, Iowa). Anti-CD62L (clone MEL-14) was obtained from American Type Culture Collection (ATCC; Manassas, Va.).

Commercially prepared anti-CD4 (clone GK1.5, phycoerythin conjugate) was obtained from Becton Dickinson (BD; San Jose, Calif.).

b. Fluorophores

For oligo:polyfluor labeling constructs, four NHS-ester 'DyLight' fluorophores (Dyomics, Germany) were selected for poly-conjugation to oligo-dextran scaffolds, including Dy490 (ex/em 490/516 nm; similar to Fluorescein/FITC); Dy549 (ex/em 560/575; similar to R-Phycoerythrin/PE); and Dy649 (ex/em 655/676 nm; similar to allophycocyanin/APC); and Dy405 (ex/em 400/420 nm; similar to Pacific Blue). For oligo:unifluor labeling constructs, three Alexa Fluor fluorophores (488, 532, 647) were selected and commercially conjugated (IDT, Coralville, Iowa) to oligonucleotide sequences.

c. Oligonucleotides

Four trial oligonucleotide pairs were selected from a previously validated sequence library developed by Feldkamp, et al., 2004; Feldkamp, et al, 2002. A unique "universal" oligonucleotide pair was generated using DNA sequence generation and evaluation software. Oligonucleotides used for conjugation to antibodies or dextran-fluorochrome scaffolds (polyfluors) were commercially synthesized with an amino-C6 group at the 5' end (Eurogentec, San Diego, Calif.). Oligonucleotides having single fluorophore molecules (unifluors) were commercially synthesized conjugated to fluorophores (IDT, Coralville, Iowa)

d. Microspheres

Commercialized fluorescent microspheres were used for ABC quantitation (BD, San Jose, Calif.) and for alignment and calibration examples (Spherotech, Glen Ellyn, Ill.) Microspheres used for oligo-conjugation were 4FB-functionalized 3 μm paramagnetic particles (Solulink, San Diego, Calif.).

e. Conversion of Amino-Oligonucleotides to 4FB-Oligonucleotides

5'-(C6-amino) oligonucleotides were dissolved in 500 μL Modification Buffer (MB; 100 mM sodium phosphate, 150 mM sodium chloride, pH 7.4) and transferred to 3 kDa MWCO VivaSpin 500 diafiltration devices (Sartorius Stedim Biotech, France). The oligo samples were centrifuged at 14,000×g for approximately 15 minutes until the retentate volume was reduced to 50 μL. Fresh MB (450 μL) was added to each sample and thoroughly mixed by pipet. This process was repeated a total of 4 times to completely remove amine-containing salts carried over from oligonucleotide synthesis. Finally, oligonucleotide samples were adjusted to approximately 0.5 OD260/μL in preparation for modification.

A solution of Succinimidyl 4-FormylBenzoate (S-4FB; Solulink, San Diego, Calif.) was prepared at 50 mg/mL in anhydrous DiMethylFormamide (DMF) and added to each oligo sample at a 20-fold excess (mol) to ensure complete reaction. Reactions proceeded at room temperature (~24° C.) for 2 hours before being diluted to 500 μL with Conjugation Buffer (CB; 100 mM sodium phosphate, 150 mM sodium chloride, pH 6.0). Excess S-4FB was removed via 4 rounds of diafiltration as described previously using CB. Post-modification oligo concentrations were adjusted to approximately 0.3 OD260/μL.

f. Preparation of Antibody-Oligonucleotide Targeting Constructs

Antibodies were supplied in PBS at approximately 1 mg/mL based on NanoDrop A280 readings using an E1% value of 14.0. Antibodies were gently concentrated to 3-4 mg/mL using 30 kDa MWCO VivaSpin 500 diafiltration devices. Antibodies were buffer exchanged into MB via 2 mL 'Zeba' desalting columns (Thermo Scientific, Rockford, Ill.) and protein concentration determined by A280. Proteins were subsequently modified with the chemical crosslinker Succinimidyl 6-HydraziNicotinate acetone hydrazone (S-HyNic; Solulink, San Diego, Calif.) at a 20-fold excess of linker to protein (mol). Following incubation for 2 hours at 24° C., the antibodies were liberated of unreacted linker by desalting with 2 mL Zeba columns equilibrated in CB. Molar Substitution Ratios (MSRs) of incorporated HyNic to antibody were determined via 2-SulfoBenzaldehyde (2-SB) assay using a molar extinction coefficient of 28,500 L mol-1 cm-1 for the hydrazone at λmax=350 nm. MSR values ranged from 6-8 HyNic per antibody molecule.

To the HyNic-modified antibodies in conjugation buffer were added 4 equivalents (mol) of 5'-4FB-modified oligonucleotide followed by 10% (v/v) of TurboLink catalyst (100 mM aniline, 100 mM sodium phosphate, 150 mM sodium chloride, pH 6.0; Solulink, San Diego, Calif.). The antibody-oligo conjugation reaction was allowed to proceed overnight at 4° C. Excess oligonucleotide was removed from the conjugated product by size exclusion chromatography using an HR-10/30 Superdex 200 PG column (GE Healthcare, Piscataway, N.J.). Removal of free oligonucleotide from the conjugated product was complete as evidenced by baseline resolution of the two A260 peaks. MSR values for oligos/antibody were determined by the ratio of the area under the A260 curves. Final protein concentration of the conjugates was determined by BCA protein assay (Thermo Scientific, Rockford, Ill.).

g. Preparation of Dextran-Oligonucleotide Heterodimers

A 1:1 oligo:dextran conjugate was prepared using the following procedure: 70 kDa amino-dextran containing approximately 20 amines/dextran (Invitrogen, Carlsbad, Calif.) was dissolved in modification buffer at 11.5 mg/mL and desalted into the same buffer via a 5 mL Zeba column to remove traces of amine-containing contaminants. The dextran solution was treated with 5-fold excess (mol) of HyNic which had been dissolved in anhydrous DMF at 25 mg/mL. Following a 2.5 hour incubation at 24° C., excess linker was removed via desalting/buffer exchange over a 5 mL Zeba column into CB. A 2-SB A350 assay performed as described above indicated an MSR of 3.4.

To the HyNic-dextran solution was added a stoichiometrically-limiting amount of 5'-4FB-oligonucleotide (0.5 molequivalents) to limit the average number of oligos per dextran to <1. Conjugation was allowed to proceed overnight at 4° C. before removal of free oligonucleotide by size exclusion chromatography over an HR-10/30 Superdex 200 PG column. Mobile phase for the purification was Loading Buffer (20 mM HEPES, 25 mM sodium chloride, pH 7.0) at 1 mL/minute flow rate.

Unconjugated dextran was removed from the conjugated product using Vivapure Q Mini-H ion-exchange devices (Sartorius Stedim Biotech, France). Crude conjugate was loaded onto the devices in loading buffer and washed with 2×400 μL of the same to remove free dextran. The oligonucleotide-dextran conjugates were eluted from the support with increasing salt concentrations of 90 mM, 450 mM, and 750 mM sodium chloride in loading buffer. Most of the conjugate eluted in the 450 mM and 750 mM fractions, and was pooled to afford the purified product. The aminodextran-oligo heterodimer was desalted and exchanged into modification buffer using a 5 mL Zeba column in preparation for dye labeling.

h. Dye-Labeling of Amino-Dextran-Oligo Heterodimers

To oligo-dextran-amino heterodimer at 6 mg/mL in Modification Buffer was added a 10.7-fold excess (mol) of DyLight dye NHS ester (Dyomics, Germany) with rapid mixing at pH 7.4. Dye labeling of the amino-dextran was achieved over a 3 hour incubation at 24° C., at which time the reaction was placed into dialysis vs. several changes of PBS. Degree Of Labeling (DOL) was determined by dividing the concentration of dye by the concentration of oligo (mol/mol), as determined spectrophotometrically at A260 after correcting for the UV contribution of the dyes themselves.

i. Cell Preparation and Labeling

C57BL/6 mice were bred and housed in a specific pathogen-free facility maintained by the University of Chicago Animal Resources Center (Chicago, Ill.), and used under the guidelines of the Institutional Animal Care and Use Committee (IACUC). Spleens were isolated and processed into single cell suspensions by pressing minced tissue through a fine mesh nylon filter, followed by washing with culture medium consisting of DMEM supplemented with HEPES, non-essential amino acids, penicillin/streptomycin and β-mercaptoethanol. Erythrocytes were lysed by brief incubation in a buffered ammonia chloride solution. Leukocytes were suspended in DMEM supplemented with 5% fetal calf serum and briefly stored at 4° C. until being counted for the number of live cells.

To prepare cells for antibody staining, splenic leukocytes were aliquoted at a density of $0.5$-$1.0 \times 10^6$ cells/sample in a buffer consisting of 1×PBS with 1% BSA. Non-specific binding of IgG to cellular Fc receptor was blocked by incubation in 50 µL of anti-FcR (clone 2.4G2 hybridoma supernatant) for 20 minutes at 24° C.

Antibody-fluorophore labeled targeting hybrids were prepared in solution prior to staining the cells by mixing antibody:oligo targeting constructs (0.1-1 µg) with complementary oligo:fluorophore labeling constructs in 1% BSA-PBS for 15-30 minutes at 24° C. Hybrids were then added to prepared, FcR-blocked murine splenocytes for 1 hour at 4° C. with slow rotation. Cells were washed once in 500 µL PBS to remove excess hybrid, and analyzed by flow cytometry.

j. Preparation and Analysis of Quantitative Microspheres

4FB-modified 3 µm paramagnetic particles (SoluLink Biosciences, San Diego Calif.) were conjugated to HyNic-oligonucleotide at 0-20 nmol per mg by 2 hour incubation in CB to result in oligo-surfaced microspheres (oligospheres). Oligospheres were washed in PBS to remove free oligo and stored in PBS at 4° C.

To prepare fluorophore-hybridized oligospheres, complementary oligo:polyfluor was added to 6.25-50 µg microspheres (~$50$-$400 \times 10^3$ particles) in desired titrations (0-40 pmol/µg). Hybridization proceeded in PBS for 15-30 minutes with gentle vortexing, spheres were washed to remove unbound fluorophore, and then were loaded into a black 96-well plate for fluorimeter analysis (Tecan Safire 2, Switzerland). Oligosphere fluorescence was evaluated in the microplate vs a standard curve of oligo:polyfluor labeling construct ranging from 0.0-1.0 pmol per microwell. Microspheres and labeling construct standards were each diluted in 100 µL total volume of dilution buffer (1×PBS) per microwell. Fluorimeter readings were normalized by using PBS dilution buffer as a blank for the standard curve, and unhybridized oligospheres to correct for autofluorescence of the oligospheres. Standard curves for each of four DyLight fluorophores (Dy490, 549, 649, 405) were plotted using graphing software with X=fluorimeter intensity and Y=pmol labeling construct per sample. $R^2$ values were >0.98 for all four standard curves.

Following fluorimeter analysis, the number of microspheres per microwell was enumerated using a handheld particle counter (Scepter Counting Device; Millipore, Billerica, Mass.). Labeling construct per microwell (pmol) was converted to molecules labeling construct and divided by the number of particles per microwell to determine Label Per (microsphere) Event (LPE).

k. Flow Cytometric Instrumentation and Analysis

Most analyses were performed using a 4-laser, 12-detector BD LSRII flow cytometer (Becton Dickinson, San Jose Calif.) which is routinely aligned and calibrated for PMT linearity by the University of Chicago Flow Cytometry Core Facility. Instrument layout includes one octagonal and three trigonal optical arrays, each equipped with a single laser. For analysis of oligospheres for spectral compensation, a 3-laser, 8-detector BD LSRII flow cytometer was used. For all analyses, cytometer acquisition settings were initiated prior to each experiment, and were unchanged for the duration of analysis. Single-event data were acquired using FACSDiva software (BD, San Jose Calif.). Data were saved as list-mode data files (.fcs) and analyzed using FlowJo software (TreeStar, Ashland, Oreg.).

Each leukocyte sample, consisting of a minimum of 10,000 events, was scatter-gated on the lymphocyte population according to standard methods [24] using an unstained control sample prior to interpretation of results. Microspheres were also scatter-gated to define single events (doublet exclusion).

l. Pseudocode for Quantitative Flow Software Algorithms

```
Main Program:
Ask User to input the Number of Channels: Store value
Number_of_Channels
Ask User to upload Control_LPE Lot and Intensity Numbers (*.csv):
Store in Control_LPE
CALL subroutine Zero_LPE (Number_of_Channels) return
Zero_GMFI.Channel Array
CALL subroutine Standard_Curve (Number_of_Channels,
Zero_GMFI.Channel Array)
    return Standard_Curve.Channel Array
FOR Channel equals 1 to Number_of_Channels DO
    Set Exp_ABC.Channel equal to 0 // Antibody Binding per Cell
    Set Exp_GMFI.Channel equal to 0
    Set Exp_LPE.Channel equal to 0
    Set Zero_Flag equal to FALSE
    REPEAT
        Ask User to Gate Experiment Cells
        Load Geometric Mean Fluorescence Intensity (GMFI)
        IF GMFI is between 10² and 10⁵ DO
            Set Exp_GMFI.Channel equal to GMFI
            Set Zero_Flag equal to TRUE
    UNTIL Zero_Flag equals True
    Plot Standard_Curve.Channel
    Set Exp_LPE.Channel equal to y=mx" where X equals
    Exp_GMFI.Channel
    Set Exp_ABC.Channel equal to Exp_LPE.Channel
    Output Standard_Curve.Channel Plot and Exp_ABC.Channel to
    User
Zero_FPE subroutine:
FOR Channel equals 1 to Number_of_Channels DO
    Set Zero_GMFI.Channel equal to 0
    Set Zero_Flag equal to FALSE
    REPEAT
        Ask User to Gate Unstained Cells (Zero reading)
        Load Median Fluorescence Intensity (GMFI)
        IF GMFI is between 0 and 10² DO
            Set Zero_GMFI.Channel equal to GMFI
            Set Zero_Flag equal to TRUE
    UNTIL Zero_Flag equals True
Standard_Curve subroutine:
FOR Channel equals 1 to Number_of_Channels DO
    Set Cell_GMFI.Channel equal to 0
    Set Zero_Flag equal to FALSE
```

-continued

```
REPEAT
    Ask User to Gate Control Cells
    Load Geometric Mean Fluorescence Intensity (GMFI)
    IF GMFI is between 10² and 10⁵ DO
        Set Control_GMFI.Channel equal to GMFI
        Set Zero_Flag equal to TRUE
UNTIL Zero_Flag equals True
Ask User if they want to Compensate? (Yes/No)
    IF Yes DO
        Have FlowJo software Discard Peak Option
Plot GMFI versus LPE
Set Standard_Curve.Channel equal to y=mxⁿ where X equals
Cell_GMFI.Channel
```

REFERENCES

The following references, to the extent that they provide exemplary procedural or other details supplementary to those set forth herein, are specifically incorporated herein by reference.

Autissier, et al., *Cytometry Part A*. 77A(5): 410-419, 2010.
Baumgarth & Roederer. *Journal of Immunological Methods*. 243(12): 77-97, 2000.
Bendall, et al., *Science*. 332:687-696, 2011
Buller, et al., *Nature*. 328(6125): 77-79, 1987.
Chattopadhyay, et al., *Immunology*. 125(4): 441-449, 2008.
Davis, et al., *Cytometry*. 33(2): 197-205, 1998.
De Rosa, et al., *Nature Medicine*. 7(2): 245-248, 2001.
Dialynas, et al., *Journal of Immunology*. 131(5): 2445-2451, 1983.
Egholm et al., *Nature*. 365(6446): 566-8, 1993
EP 266,032
Feldkamp, et al., *ChemPhysChem*. 5(3): 367-372, 2004.
Feldkamp, et al., *DNA Computing*. 2340: 23-32, 2002.
Feldkamp, *Journal of Computational Chemistry*. 31(3): 660-663, 2010.
Fu, et al., *American Journal of Transplantation*. 4(1): 65-78, 2004.
Givan, *Flow Cytometry: First Principles*. First ed: John Wiley and Sons. 273, 2001.
Gratama, et al., Cytometry. 33(2): 166-178, 1998.
Gulley, et al., *The Journal of Immunology*. 140(11): 3751-3757, 1988.
Hultin, et al., Cytometry. 33(2): 123-132, 1998.
Lee, et al., *The Journal of Experimental Medicine*. 175(4): 1013-1025, 1992.
Lin, et al., *Pediatr Res*. 43(S4): 151-151, 1998.
Maher & Fletcher, *Clinical and Applied Immunology Reviews*. 5(6): 353-372, 2005.
McLaughlin, et al., *Cytometry Part A*. 73A(5): 400-410, 2008.
Roederer, et al., *Cytometry*. 29(4): 328-339, 1997.
Schlenke, et al., *Cytometry*. 33(3): 310-317, 1998.
Schwartz, et al., *Cytometry Part B: Clinical Cytometry*. 57B(1): 1-6, 2004.
Schwartz, et al., Cytometry. 33(2): 106-114, 1998.
U.S. Pat. No. 4,196,265
U.S. Pat. No. 4,659,774
U.S. Pat. No. 4,682,195
U.S. Pat. No. 4,683,202
U.S. Pat. No. 4,816,571
U.S. Pat. No. 4,959,463
U.S. Pat. No. 5,141,813
U.S. Pat. No. 5,264,566
U.S. Pat. No. 5,428,148
U.S. Pat. No. 5,539,082
U.S. Pat. No. 5,554,744
U.S. Pat. No. 5,574,146
U.S. Pat. No. 5,602,244
U.S. Pat. No. 5,645,897
U.S. Pat. No. 5,654,413
U.S. Pat. No. 5,705,629
U.S. Pat. No. 5,714,331
U.S. Pat. No. 5,719,262
U.S. Pat. No. 5,736,330
U.S. Pat. No. 5,736,336
U.S. Pat. No. 5,766,855
U.S. Pat. No. 5,773,571
U.S. Pat. No. 5,786,461
U.S. Pat. No. 5,891,625
U.S. Pat. No. 5,908,845
U.S. Pat. No. 6,057,107
U.S. Pat. No. 7,226,737
U.S. Pat. No. 7,645,868
Wang, et al., *Cytometry Part A*. 73A(4): 279-288, 2008.
WO 92/20702

The invention claimed is:

1. A method of quantitative flow cytometry comprising:
   (a) providing a labeled sample by contacting a sample comprising one or more cells with a labeled targeting construct under conditions suitable for binding of the labeled targeting construct to an antigen on the cells; wherein the labeled targeting construct comprises a targeting moiety:ligand complex and a bioconjugate; wherein the bioconjugate comprises a biomolecule attached to a labeling moiety; and wherein the biomolecule of the bioconjugate binds to the ligand of the targeting moiety:ligand complex;
   (b) contacting the labeled sample with a population of quantitative labeled ligand-surfaced microspheres, wherein the population of quantitative labeled ligand-surfaced microspheres is labeled with the same bioconjugate as the labeled targeting construct;
   (c) analyzing the population of quantitative labeled ligand-surfaced microspheres and the cells that bind the labeled targeting construct in the sample using a flow cytometer;
   (d) determining a Geometric Mean Fluorescent Intensity (GMFI) versus Label Per Event (LPE) trendline from the GMFIs of the population of quantitative labeled ligand-surfaced microspheres;
   (e) determining the LPE for one or more cell populations that bind the labeled targeting construct from the GMFI versus LPE trendline; and
   (f) quantifying the amount of labeled targeting construct binding per cell,
wherein the biomolecule of the bioconjugate binds to the ligand of the ligand-surfaced microsphere; wherein the target is a cellular target on or within cells; and wherein the ligands of the ligand-surfaced microsphere and targeting moiety:ligand complex are peptides or haptens.

2. The method of claim 1 further comprising:
   (a) providing a labeled sample by contacting the sample with at least a first and a second labeled targeting construct, wherein the first labeled targeting construct comprises a targeting moiety:ligand complex and a bioconjugate that differs from the targeting moiety:ligand complex and bioconjugate of the second labeled targeting construct, under conditions suitable for binding of the first and the second labeled targeting constructs to their respective targets on the cells; and
   (b) contacting the labeled sample with at least a first and a second population of quantitative labeled ligand-surfaced microspheres, wherein the bioconjugates of the first and the second populations of quantitative labeled ligand-surfaced microspheres differ from each other, but are the same as the bioconjugates utilized in the labeled targeting construct of either the first or the second labeled targeting constructs;
   (c) analyzing the populations of quantitative labeled ligand-surfaced microspheres and the cells that bind the labeled targeting construct in the sample using a flow cytometer;
   (d) determining the GMFI versus LPE trendline from the GMFIs of at least two different populations of quantitative labeled ligand-surfaced microspheres;
   (e) determining the LPE for the one or more cell populations that bind the first and/or second labeled targeting construct from the GMFI versus LPE trendlines; and
   (f) quantifying the amount of labeled targeting construct binding per cell.

3. The method of claim 2, wherein the first labeled targeting construct comprises an antibody that binds to CD4 and the second labeled targeting construct comprises an antibody that binds to CD8.

4. The method of claim 2, further comprising contacting the sample with at least a third and a fourth different labeled targeting construct under conditions suitable for binding of the third and the fourth labeled targeting constructs to their respective targets on the cells.

5. The method of claim 4, wherein the first labeled targeting construct comprises an antibody that binds to CD4, the second labeled targeting construct comprises an antibody that binds to CD8, the third labeled targeting construct comprises an antibody that binds to CD43, and the fourth labeled targeting construct comprises an antibody that binds to CD62L.

6. The method of claim 2, wherein the sample is a whole blood sample or a buffy coat sample.

7. The method of claim 1, wherein the sample is a cultured preparation of mammalian cells, a biopsy cell aspirate, a tissue sample, or an environmental sample.

8. The method of claim 1, wherein the cells are immune cells.

9. The method of claim 8, wherein the immune cells are T cells, B cells, NK cells, granulocytes, or monocytes.

10. The method of claim 1, wherein the cells are tumor cells, stem cells or immortalized cells.

11. The method of claim 1, wherein the cells are rodent, plant, bacterial, fungi, protozoan, or metazoan cells.

12. The method of claim 1, wherein the labeled targeting construct comprises an antibody that specifically binds to CD4, CD8, CD43, or CD62L.

13. The method of claim 1, wherein the targeting moiety is an antibody and wherein the antibody is a monoclonal antibody, an antibody fragment, a polyclonal antibody, a recombinant antibody, a synthetic antibody, or a chimeric antibody.

14. The method of claim 1, wherein the labeling moiety comprises a fluorescent label and wherein the fluorescent label is Dy490, Dy549, Dy649, or Dy405.

15. The method of claim 1, wherein the population of quantitative labeled ligand-surfaced microspheres comprises at least four subpopulations of different ligand-surfaced microspheres bound with at least four different concentrations of bioconjugates.

16. The method of claim 15, wherein the labeling moiety comprises a fluorescent label and wherein the fluorescent label is Dy490, Dy549, Dy649, or Dy405.

17. The method of claim 1, wherein the labeled targeting construct is contacted with the sample before or after the population of quantitative labeled ligand-surfaced microspheres is contacted with the sample.

18. The method of claim 1, wherein the biomolecule is an antibody.

* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
cctgcgtcgt ttaaggaagt ac                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
```

```
gtacttcctt aaacgacgca gg                                                    22

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
ggtccggtca taaagcgata ag                                                    22

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
cttatcgctt tatgaccgga cc                                                    22

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
gctgacatag agtgcgatac                                                       20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtatcgcact ctatgtcagc                                                       20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
tgtgctcgtc tctgcatact                                                       20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
agtatgcaga gacgagcaca                                                       20

<210> SEQ ID NO 9
<211> LENGTH: 20
<212> TYPE: DNA
<213> ORGANISM: Artificial Sequence
```

-continued

```
<220> FEATURE:
<223> OTHER INFORMATION: Synthetic Primer

<400> SEQUENCE: 9
ggaagcggtg ctatccatct                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
agatggatag caccgcttcc                                                    20
```